(12) United States Patent
Hunziker et al.

(10) Patent No.: US 11,820,981 B2
(45) Date of Patent: Nov. 21, 2023

(54) MODULATION OF TJP1 EXPRESSION TO REGULATE REGENERATION OF HEART CELLS

(71) Applicants: AGENCY FOR SCIENCE, TECHNOLOGY AND RESEARCH, Singapore (SG); NATIONAL UNIVERSITY OF SINGAPORE, Singapore (SG)

(72) Inventors: Walter Hunziker, Singapore (SG); Jianliang Xu, Singapore (SG); Jiong-Wei Wang, Singapore (SG); P. Jaya Kausalya, Singapore (SG)

(73) Assignees: AGENCY FOR SCIENCE, TECHNOLOGY AND RESEARCH, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 1075 days.

(21) Appl. No.: 16/333,586

(22) PCT Filed: Sep. 14, 2017

(86) PCT No.: PCT/SG2017/050462
§ 371 (c)(1),
(2) Date: Mar. 14, 2019

(87) PCT Pub. No.: WO2018/052374
PCT Pub. Date: Mar. 22, 2018

(65) Prior Publication Data
US 2019/0256846 A1 Aug. 22, 2019

(30) Foreign Application Priority Data
Sep. 14, 2016 (SG) .......................... 10201607673U

(51) Int. Cl.
| | |
|---|---|
| C07H 21/02 | (2006.01) |
| C07H 21/04 | (2006.01) |
| C12N 15/113 | (2010.01) |
| A61K 35/761 | (2015.01) |
| A61K 38/17 | (2006.01) |
| A61K 38/18 | (2006.01) |
| A61P 9/10 | (2006.01) |
| A61K 31/713 | (2006.01) |
| A61K 31/7088 | (2006.01) |

(52) U.S. Cl.
CPC .......... *C12N 15/113* (2013.01); *A61K 31/713* (2013.01); *A61K 35/761* (2013.01); *A61K 38/1709* (2013.01); *A61K 38/1825* (2013.01); *A61K 38/1866* (2013.01); *A61K 38/1883* (2013.01); *A61P 9/10* (2018.01); *A61K 31/7088* (2013.01); *A61K 38/1808* (2013.01); *A61K 38/1841* (2013.01); *C12N 15/1138* (2013.01); *C12N 2310/11* (2013.01); *C12N 2310/122* (2013.01); *C12N 2310/14* (2013.01); *C12N 2310/341* (2013.01); *C12N 2310/531* (2013.01)

(58) Field of Classification Search
CPC ........................ C12N 15/113; C12N 2310/531
See application file for complete search history.

(56) References Cited

FOREIGN PATENT DOCUMENTS

| | | |
|---|---|---|
| CN | 1333231 A | 1/2002 |
| WO | 2005000403 A2 | 1/2005 |
| WO | 2011011388 A2 | 1/2011 |
| WO | 2013148736 A1 | 10/2013 |
| WO | 2016029191 A2 | 2/2016 |

OTHER PUBLICATIONS

Extended European Search Report of the European Patent Office dated Apr. 9, 2020 for related European Patent Application No. 17851187.9.
Xue et al., "Decreased mRNA levels of cardiac Cx43 and ZO1 in sudden cardiac death related to coronary atherosclerosis: a pilot study" International Journal of Legal Medicine, Mar. 14, 2016, vol. 130 No. 4, pp. 915-922.
Qian, et al., "In vivo reprogramming of murine cardiac fibroblasts into induced cardiomyocytes," Nature, May 31, 2012, 8 pgs., vol. 485, Macmillan Publishers Limited.
Rhett, et al., "Regulation of Cx43 GJ Aggregation by ZO-1 Potentially Modulates Differential Adhesion Between Cardiac Myocytes and Fibroblasts," Circulation, Mar. 22, 2018, 4 pgs. American Heart Association, Abstract Only.
Sepulveda, et al., "Combinatorial Expression of GATA4, Nkx2-5, and Serum Response Factor Directs Early Cardiac Gene Activity," The Journal of Biological Chemistry, Jul. 12, 2002, pp. 25775-25782, vol. 277, No. 28, The American Society for Biochemistry and Molecular Biology, Inc., USA.
Shapiro, et al., "Cyclin A2 Induces Cardiac Regeneration After Myocardial Infarction Through Cytokinesis of Adult Cardiomyocytes," Science Translational Medicine, Feb. 19, 2014, 12 pgs., vol. 6, No. 224, American Association for the Advancement of Science, USA.

(Continued)

Primary Examiner — Amy H Bowman
(74) Attorney, Agent, or Firm — Womble Bond Dickinson (US) LLP

(57) ABSTRACT

The invention is a method for treating a heart disease, in particular acute myocardial infarction (AMI) in a subject comprising the step of administering to the subject a Tjp1 inhibitor, wherein administration of said Tjp1 inhibitor promotes cardiomyocyte proliferation. The invention further includes use of Tjp1 inhibitor in the manufacture of a medicament for a heart disease, a patch, and a nucleic acid encoding a Tjp1 inhibitor. In a particular embodiment, the Tjp1 inhibitor is a nucleic acid, i.e. an siRNA or shRNA of Tjp1. The invention also includes administration of said Tjp1 inhibitor in combination with Neuregulin-1 (NRG1), Fibroblast growth factor (FGF), Vascular endothelial growth factor (VEGF) or Follistatin-like 1 (Fst1) and wherein said inhibitor is delivered in an adeno-associated virus of serotype 9 (AAV 9).

18 Claims, 23 Drawing Sheets
Specification includes a Sequence Listing.

(56) References Cited

OTHER PUBLICATIONS

Siddiquee, et al., "Selective chemical probe inhibitor of Stat3, identified through structure-based virtual screening, induces antitumor activity," PNAS, May 1, 2007, pp. 7391-7396, vol. 104, No. 18.
Sohal, et al., "Temporally Regulated and Tissue-Specific Gene Manipulations in the Adult and Embryonic Heart Using a Tamoxifen-Inducible Cre Protein," Circulation Research, Jul. 6, 2001, pp. 20-25, American Heart Association.
Song, et al., "Heart repair by reprogramming non-myocytes with cardiac transcription factors," Nature, May 31, 2012, pp. 599-606, vol. 485, Macmillan Publishers Limited.
Soriano, et al., "Generalized lacZ expression with the ROSA26 Cre reporter strain," Nature Genetics, Jan. 1999, pp. 70-71, vol. 21, Nature America Inc.
Sy, et al., "Sustained release of a p38-inhibitor from non-inflammatory microspheres inhibits cardiac dysfunction," Nature Materials, Nov. 2008, pp. 863-868, vol. 7, No. 11, National Institutes of Health.
The International Preliminary Report on Patentability for PCT Application No. PCT/SG2017/050462 dated Jan. 7, 2018, 15 pgs.
The International Search Report for PCT Application No. PCT/SG2017/050462 dated Nov. 23, 2017, 7 pgs.
The Written Opinion of the International Searching Authority for PCT Application No. PCT/SG2017/050462 dated Nov. 23, 2017, 5 pgs.
Timmers, et al., "Toll-Like Receptor 4 Mediates Maladaptive Left Ventricular Remodeling and Impairs Cardiac Function After Myocardial Infarction," Circulation Research, Feb. 1, 2008, pp. 257-264, vol. 102.
Toyofuku, et al., "Direct Association of the Gap Junction Protein Connexin-43 with ZO-1 in Cardiac Myocytes," The Journal of Biological Chemistry, May 22, 1998, pp. 12725-12731, vol. 273, No. 21, The American Society for Biochemistry and Molecular Biology, Inc., USA.
Uygur, et al., "Mechanisms of Cardiac Regeneration," Developmental Cell Review, Feb. 22, 2016, pp. 362-374, vol. 36, Elsevier Inc.
Wada, et al., "Induction of human cardiomyocyte-like cells from fibroblasts by defined factors," PNAS, Jul. 30, 2013, pp. 12667-12672, vol. 110, No. 31.
Wang, et al., "Mitogen-Activated Protein Kinases in Heart Development and Diseases," Circulation, Sep. 18, 2007, pp. 1413-1423, vol. 116.
Wang, et al., "Small Molecules Enable Cardiac Reprogramming of Mouse Fibroblasts with a Single Factor, Oct4," Cell Reports, Mar. 13, 2014, pp. 951-960, vol. 6, The Authors.
Wei, et al., "Epicaridal FSTL1 reconstitution regenerates the adult mammalian heart," Nature, Sep. 24, 2015, pp. 479-501, vol. 525, Macmillan Publishers Limited.
Woulfe, et al., "Glycogen Synthase Kinase-3β Regulates Post-Myocardial Infarction Remodeling and Stress-Induced Cardiomyocyte Proliferation In Vivo," Circulation Research, May 28, 2010, pp. 1635-1645, vol. 106.
Wu, et al., "Preclinical Testing of PI3K/AKT/mTOR Signaling Inhibitors in a Mouse Model of Ovarian Endometrioid Adenocarcinoma," Clinical Cancer Research, Sep. 8, 2011, pp. 7359-7372, vol. 17, No. 23, American Association for Cancer Research.
Xie, et al., "AST1306, A Novel, Irreversible Inhibitor of the Epidermal Growth Factor Receptor 1 and 2, Exhibits Antitumor Activity Both In Vitro and In Vivo," PLoS ONE, Jul. 18, 2011, 10 pgs., vol. 6, No. 7.
Xin, et al., "Mending broken hearts: cardiac development as a basis for adult heart regeneration and repair," Molecular Cell Biology, Aug. 2013, pp. 529-541, vol. 14, Macmillan Publishers Limited.
Xu, et al., "Early Embryonic Lethality of Mice Lacking ZO-2, but Not ZO-3, Reveals Critical and Nonredundant Roles for Individual Zonula Occludens, Proteins in Mammalian Development," Molecular and Cellular Biology, Mar. 2008, pp. 1669-1678, vol. 28, No. 5, American Society for Microbiology.
Xu, et al., "ZO-1 Regulates Erk, Smad1/5/8, Smad2, and RhoA Activities to Modulate Self-Renewal and Differentiation of Mouse Embryonic Stem Cells," Stem Cells, Jul. 10, 2012, pp. 1885-1900, vol. 30.
Yahalom-Ronen, et al., "Reduced matrix rigidity promotes neonatal cardiomyocyte dedifferentiation, proliferation, and clonal expansion," eLife, Aug. 12, 2015, 18 pgs., vol. 4.
Yamakawa, et al., "Fibroblast Growth Factors and Vascular Endothelial Growth Factor Promote Cardiac Reprogramming under Defined Conditions," Stem Cell Reports, Dec. 8, 2015, pp. 1128-1142, vol. 5, The Authors.
Yoshioka, et al., "Cardiomyocyte hypertrophy and degradation of connexin43 through spatially restricted autocrine/paracrine heparin-binding EGF," PNAS, Jul. 26, 2005, pp. 10622-10627, vol. 102, No. 30.
Zeisberg, et al., "Morphogenesis of the right ventricle requires myocardial expression of Gata4," The Journal of Clinical Investigation, Jun. 2005, pp. 1522-1531, vol. 115, No. 6.
Zhang, et al., "Tight Junction Protein 1 Modulates Proteasome Capacity and Proteasome Inhibitor Sensitivity in Multiple Myeloma via EGFR/JAK1/STAT3 Signaling," Cancer Cell, May 9, 2016, pp. 639-652, vol. 29, Elsevier Inc.
Zhao, et al., "High-efficiency reprogramming of fibroblasts into cardiomyocytes requires suppression of pro-fibrotic signalling," Nature Communications, Sep. 10, 2015, 15 pgs., vol. 6.
Zhong, et al., "Stat3: A STAT Family Member Activated by Tyrosine Phosphorylation in Response to Epidermal Growth Factor and Interleukin-6," Science, Apr. 1, 1994, pp. 95-98, vol. 264, No. 5155.
Zhou, H., et al., "Akt1/protein kinase B enhances transcriptional reprogramming of fibroblasts to functional cardiomyocytes," PNAS, Sep. 22, 2015, pp. 11864-11869, vol. 12, No. 38.
Zhou, Q., et al., "The Hippo Pathway in Heart Development, Regeneration, and Diseases," Circulation Research, Apr. 10, 2015, pp. 1431-1447, vol. 116.
Zhou, Y., et al., "Bmi1 Is a Key Epigenetic Barrier to Direct Cardiac Reprogramming," Cell Stem Cell, Mar. 3, 2016, pp. 382-395, vol. 18, Elsevier Inc.
Arslan, et al., "Innate immune signaling in cardiac ischemia," Nature Reviews Cardiology, Mar. 29, 2011, pp. 292-300, vol. 8, Macmillan Publishers Limited.
Arslan, et al., "Treatment With OPN-305, a Humanized Anti-Toll-Like Receptor-2 Antibody, Reduces Myocardial Ischemia/Reperfusion Injury in Pigs," Circulation: Cardiovascular Interventions, Apr. 2012, pp. 279-287.
Barker, et al., "Increased Association of ZO-1 With Connexin43 During Remodeling of Cardiac Gap Junctions," Circulation Research, Feb. 22, 2002, pp. 317-324.
Barrott, et al., "Deletion of mouse Porcn blocks Wnt ligand secretion and reveals an ectodermal etiology of human focal dermal hypoplasia/Goltz syndrome," PNAS, Aug. 2, 2011, pp. 12752-12757, vol. 108, No. 31.
Bersell, et al., "Neuregulin1/ErbB4 Signaling Induces Cardiomyocyte Proliferation and Repair of Heart Injury," Cell, Jul. 24, 2009, pp. 257-270, vol. 138, Elsevier Inc.
Bisping, et al., "Gata4 is required for maintenance of postnatal cardiac function and protection from pressure overload-induced heart failure," PNAS, Sep. 26, 2006, pp. 14471-14476, vol. 103, No. 39.
Bruce, et al., "Gap junction remodelling in human heart failure is associated with increased interaction of connexin43 with ZO-1," Cardiovascular Research, 2008, pp. 757-765, vol. 77, European Society of Cardiology.

(56) References Cited

OTHER PUBLICATIONS

Cheng, et al., "Cyclin A2 Induces Cardiac Regeneration After Myocardial Infraction and Prevents Heart Failure," Circulation Research, Jun. 22, 2007, pp. 1741-1748, vol. 100.
Chidiac, et al., "Comparitive Phosphoproteomics Analysis of VEGF and Angiopoietin-1 Signaling Reveals ZO-1 as a Critical Regulator of Endothelial Cell Proliferation," Molecular & Cellular Proteomics, Feb. 4, 2016, pp. 1511-1525, The American Society for Biochemistry and Molecular Biology.
DeBosch, et al., "Akt1 Is Required for Physiological Cardiac Growth," Circulation, May 2, 2006, pp. 2097-2104, vol. 113.
Duva, et al., "ERBB2 triggers mammalian heart regeneration by promoting cardiomyocyte dedifferentiation and proliferation," Nature Cell Biology, Apr. 6, 2015, pp. 627-650, vol. 17, No. 5, Macmillan Publishers Limited.
Eulalio, et al., "Functional screening identifies miRNAs inducing cardiac regeneration," Nature, Dec. 27, 2012, 9 pgs., vol. 492, Macmillan Publishers Limited.
Fang, et al., "Translational profiling of cardiomyocytes identifies an early Jak1/Stat3 injury response required for zebrafish heart regeneration," PNAS, Aug. 13, 2013, pp. 13416-13421, vol. 110, No. 33.
Fu, et al., "Direct reprogramming of mouse fibroblasts into cardiomyocytes with chemical cocktails," Cell Research, Sep. 2015, pp. 1013-1024, vol. 25, No. 9.
Gemberling, et al., "Nrg1 is an injury-induced cardiomyocyte mitogen for the endogenous heart regeneration program in zebrafish," eLIFE, Apr. 1, 2015, 17 pgs.
Giepmans, et al., "The gap junction protein connexin43 interacts with the second PDZ domain of the zona occludens-1 protein," Current Biology, Jul. 27, 1998, pp. 931-934, vol. 8, Current Biology Publications.
Heallen, et al., "Hippo Pathway Inhibits Wnt Signaling to Restrain Cardiomyocyte Proliferation and Heart Size," Science, Apr. 22, 2011, 5 pgs., vol. 332.
Hsieh, et al., "Evidence from a genetic fate-mapping study that stem cells refresh adult mammalian cardiomyocytes after injury," Nature Medicine, Aug. 2007, pp. 970-974, vol. 13, No. 8.
Hu, et al. "Convergence between Wnt-β-catenin and EGFR signaling in cancer," Molecular Cancer, 2010, 7 pgs.
Hunter, et al., "Zonula Occludens-1 Alters Connexin43 Gap Junction Size and Organization by Influencing Channel Accretion," Molecular Biology of the Cell, Dec. 2005, pp. 5686-5698, vol. 16.
Ieda, et al., "Direct Reprogramming of Fibroblasts into Functional Cardiomyocytes by Defined Factors," Cell, Aug. 6, 2010, pp. 375-386, vol. 142, Elsevier Inc.
Ikenishi, et al., "Cell cycle regulation in mouse heart during embryonic and postnatal stages," Development, Growth & Differentiation, 2012, pp. 731-738, vol. 54, Japanese Society of Developmental Biologists, Japan.
"In-hospital mortality following acute myocardial infarction," Health at a Glance, 2011, pp. 108-109, OECD Indicators.
Inagaki, et al., "Robust Systematic Transduction with AAv9 Vectors in Mice: Efficient Global Cardiac Gene Transfer Superior to That of AAV8," Molecular Therapy, Jul. 2006, pp. 45-53, vol. 14, No. 1.
Inagawa, et al., "Induction of Cardiomyocyte-Like Cells in Infarct Hearts by Gene Transfer of Gata4, Mef2c, and Tbx5," Circulation Research, Oct. 12, 2012, pp. 1147-1156, vol. 111.
Itoh, et al., "The Structural and Functional Organization of the Podocyte Filtration Slits Is Regulated by Tjp1/ZO-1," PLOS ONE, Sep. 2014, 11 pgs. vol. 9, No. 9.
Jayawardena, et al., "MicroRNA-Mediated In Vitro and In Vivo Direct Reprogramming of Cardiac Fibroblasts to Cardiomyocytes," Circulation Research, May 25, 2012, pp. 1465-1473.
Jopling, et al., "Zebrafish heart regeneration occurs by cardiomyocyte dedifferentiation and proliferation," Nature, Mar. 25, 2010, pp. 606-611, vol. 464, Macmillan Publishers Limited.
Katsuno, et al., "Deficiency of Zonula Occludens-1 Causes Embryonic Lethal Phenotype Associated with Defected Yolk Sac Angiogenesis and Apoptosis of Embryonic Cells," Molecular Biology of the Cell, Jun. 2008, pp. 2465-2475, vol. 19, The American Society for Cell Biology.
Kerkela, et al., "Deletion of GSK-3β in mice leads to hypertrophic cardiomyopathy secondary to cardiomyoblast hyperproliferation," The Journal of Clinical Investigation, Nov. 2008, pp. 3609-3618, vol. 118, No. 11.
Kieken, et al., "Structural and Molecular Mechanisms of Gap Junction Remodeling in Epicardial Border Zone Myocytes following Myocardial Infarction," Circulation Research, May 8, 2009, pp. 1103-1112, vol. 104, No. 9, National Institutes of Health.
Kostin, S., "Zonula occludens-1 and connexin 43 expression in the failing human heart," Journal of Cellular and Molecular Medicine, May 23, 2007, pp. 892-895, vol. 11, No. 4, Foundation for Cellular and Molecular Medicine/Blackwell Publishing Ltd.
Kubin, et al., "Oncostatin M Is a Major Mediator of Cardiomyocyte Dedifferentiation and Remodeling," Cell Stem Cell Article, Nov. 4, 2011, pp. 420-432, vol. 9, Elsevier Inc.
Lee, et al., "ERK activation drives intestinal tumorigenesis in APCmin/+ mice," Nature Medicine, Jun. 2010, pp. 665-671, vol. 16, No. 6.
Liang, et al., "The Transcription Factors GATA4 and GATA6 Regulate Cardiomyocyte Hypertrophy in Vitro and in Vivo," The Journal of Biological Chemistry, Aug. 10, 2001, pp. 30245-30253, vol. 276, No. 32, The American Society for Biochemistry and Molecular Biology, Inc.
Liang, et al., "Redefining the roles of p38 and JNK signaling in cardiac hypertrophy: dichotomy between cultured myocytes and animal models," Journal of Molecular and Cellular Cardiology, Oct. 2003, pp. 1385-1394, vol. 35, Elsevier.
Liebmann, C., "Regulation of MAP kinase activity by peptide receptor signalling pathway: Paradigms of multiplicity," Cellular Signalling, Apr. 2, 2001, pp. 777-785, vol. 13, Elsevier.
Liu, et al., "Targeting Wnt-driven cancer through the inhibition of Porcupine by LGK974," PNAS, Dec. 10, 2013, pp. 20224-20229, vol. 110, No. 50.
Lopez-Malpartida, et al., "Differential ErbB receptor expression and intracellular signaling activity in lung adenocarcinomas and squamous cell carcinomas," Lung Cancer, 2009, pp. 25-33, vol. 65, Elsevier.
Maiers, et al., "ZO-1 recruitment to α-catenin—a novel mechanism for coupling the assembly of tight junctions to adherens junctions," Journal of Cell Science, Jun. 4, 2013, pp. 3904-3915, vol. 126, No. 17, The Company of Biologists.
Mattoon, et al., "The docking protein Gab I is the primary mediator of EGF-stimulated activation of the PI-3K/Akt cell survival pathway," BMC Biology, Nov. 18, 2004, 12 pgs., vol. 2, No. 24, BioMed Central Ltd.
Muraoka, et al., "MiR-133 promotes cardiac reprogramming by directly repressing Snai1 and silencing fibroblast signatures," The EMBO Journal, Jun. 11, 2014, pp. 1565-1581, vol. 33, No. 14, The Authors.
Murphy, et al., "Mortality in the United States, 2014," NCHS Data Brief, Dec. 2015, 8 pgs., No. 229, U.S. Department of Health and Human Services.
Oka, et al., "Cardiac-Specific Deletion of Gata4 Reveals Its Requirement for Hypertrophy, Compensation, and Myocyte Viability," Circulation Research, Mar. 31, 2006, pp. 837-845, vol. 98.
Palatinus, et al., "ZO-1 determines adherens and gap junction localization at intercalated disks," American Journal of Physiology-Heart and Circulatory Physiology, 2011, pp. H583-H594, vol. 300, The American Physiological Society.
Pashmforoush, et at, "Nkx2-5 Pathways and Congenital Heart Disease: Loss of Ventricular Myocyte Lineage Specification Leads to Progressive Cardiomyopathy and Complete Heart Block," Cell, Apr. 30, 2004, pp. 373-386, vol. 117, Cell Press.
Polakis, P., "Wnt Signaling in Cancer," Cold Spring Harbor Perspective in Biology, Mar. 20, 2012, 14 pgs., Cold Spring Harbor Laboratory Press.
Porrello, et al., "Transient Regenerative Potential of the Neonatal Mouse Heart," Science, Feb. 25, 2011, pp. 1078-1080, vol. 331, American Association for the Advancement of Science.
Poss, et al., "Heart Regeneration in Zebrafish," Science, Dec. 13, 2002, pp. 2188-2190, vol. 298.

(56) References Cited

OTHER PUBLICATIONS

Alexandra F. Bruce, Stephen Rothery, Emmanual Dupont & Nicholas J. Severs, "Gap junction remodelling in human heart failure is associated with increased interaction of connexin43 with ZO-1," Cardiovascular Research, 2008, pp. 757-765, vol. 77, European Society of Cardiology.

Xun Ai, et al., "Connexin 43 Downregulation and Dephosphorylation in Nonischemic Heart Failure Is Associated With Enhanced Colocalized Protein Phosphatase Type 2A," Circulation Research, pp. 54-63 (2005).

Emmanuel Dupont, et al., "Altered Connexin Expression in Human Congestive Heart Failure," J Mol Cell Cardiol 33, 359-371 (2001).

Laing, et al., "Diminished zonula occludens-1 expression in the failing human heart," Cardiovascular Pathology, Jan. 8, 2007, pp. 159-164, vol. 16, Elsevier Inc.

Arrow: Edu    Arrowhead: DAPI

Arrow: Edu   Arrowhead: DAPI   Asterisk: MHC

Arrow: Edu   Arrowhead: DAPI

```
ErbB2:   ----DQDPPERGAPPSTFKGTPTAENPEYLGLDVPV   --- SEQ ID NO: 7
ErbB3:   --- TLRSLEATD SAFDNPDYWHSRLFPKANAQRT    --- SEQ ID NO: 8
ErbB4:   ----PIVAENPEYLSEFSLKPGTVLPPPPYRHRNTVV   --- SEQ ID NO: 9
```

C

Arrow: Edu   Arrowhead: DAPI

D

E

Arrow: Edu   Arrowhead: DAPI

B mTJP1 shRNA#1 --- SEQ ID NO: 3
CCGGCGTGGATTGAACTTACTAAATCTCGAGATTTAGTAAGTTCAATCCACGTTTTTG mTJP1 shRNA#2 --- SEQ ID NO: 4
CCGGCCGCGAAGTTATGAGCAAGTTCTCGAGAACTTGCTCATAACTTCGCGGTTTTTG

SEQUENCE LISTING

<160> NUMBER OF SEQ ID NOS: 9

<210> SEQ ID NO 1
<211> LENGTH: 58
<212> TYPE: DNA
<213> ORGANISM: Artificial Sequence
<220> FEATURE:
<223> OTHER INFORMATION: mTJP1 shRNA

<400> SEQUENCE: 1
ccgggcctgc atacaataaa gcaaactcga gtttgcttta ttgtatgcag gctttttg            58

<210> SEQ ID NO 2
<211> LENGTH: 58
<212> TYPE: DNA
<213> ORGANISM: Artificial Sequence

```
<220> FEATURE:
<223> OTHER INFORMATION: mTJP1 shRNA

<400> SEQUENCE: 2
ccggggaacc actctatcaa gtattctcga gaatacttga tagagtggtt ccttttttg      58

<210> SEQ ID NO 3
<211> LENGTH: 58
<212> TYPE: DNA
<213> ORGANISM: Artificial Sequence
<220> FEATURE:
<223> OTHER INFORMATION: mTJP1 shRNA

<400> SEQUENCE: 3
ccggcgtgga ttgaacttac taaatctcga gatttagtaa gttcaatcca cgttttttg      58

<210> SEQ ID NO 4
<211> LENGTH: 58
<212> TYPE: DNA
<213> ORGANISM: Artificial Sequence
<220> FEATURE:
<223> OTHER INFORMATION: mTJP1 shRNA

<400> SEQUENCE: 4
ccggccgcga agttatgagc aagttctcga gaacttgctc ataacttcgc ggttttttg      58

<210> SEQ ID NO 5
<211> LENGTH: 24
<212> TYPE: DNA
<213> ORGANISM: Artificial Sequence
<220> FEATURE:
<223> OTHER INFORMATION: Primer 1

<400> SEQUENCE: 5
cttctctgac cctacacagc tacc                                           24

<210> SEQ ID NO 6
<211> LENGTH: 20
<212> TYPE: DNA
<213> ORGANISM: Artificial Sequence
<220> FEATURE:
<223> OTHER INFORMATION: Primer 2

<400> SEQUENCE: 6
atcgtgtggg aaagacaagc                                                20

<210> SEQ ID NO 7
<211> LENGTH: 32
<212> TYPE: PRT
<213> ORGANISM: Homo sapiens

<400> SEQUENCE: 7

Asp Gln Asp Pro Pro Glu Arg Gly Ala Pro Pro Ser Thr Phe Lys Gly
1               5                   10                  15

Thr Pro Thr Ala Glu Asn Pro Glu Tyr Leu Gly Leu Asp Val Pro Val
            20                  25                  30

<210> SEQ ID NO 8
<211> LENGTH: 31
<212> TYPE: PRT
<213> ORGANISM: Homo sapiens
```

```
<400> SEQUENCE: 8

Thr Leu Arg Ser Leu Glu Ala Thr Asp Ser Ala Phe Asp Asn Pro Asp
1               5                   10                  15

Tyr Trp His Ser Arg Leu Phe Pro Lys Ala Asn Ala Gln Arg Thr
            20                  25                  30

<210> SEQ ID NO 9
<211> LENGTH: 33
<212> TYPE: PRT
<213> ORGANISM: Homo sapiens

<400> SEQUENCE: 9

Pro Ile Val Ala Glu Asn Pro Glu Tyr Leu Ser Glu Phe Ser Leu Lys
1               5                   10                  15

Pro Gly Thr Val Leu Pro Pro Pro Tyr Arg His Arg Asn Thr Val
            20                  25                  30

Val
```

MODULATION OF TJP1 EXPRESSION TO REGULATE REGENERATION OF HEART CELLS

CROSS-REFERENCE TO RELATED APPLICATIONS

This patent application is a U.S. National Phase Application Under 35 U.S.C. § 371 of International Application No. PCT/SG2017/050462, filed 14 Sep. 2017, entitled MODULATION OF TJP1 EXPRESSION TO REGULATE REGENERATION OF HEART CELLS, which claims the benefit of priority of Singapore provisional application No. 10201607673U, filed on 14 Sep. 2016, the contents of which were incorporated by reference in the entirety for all purposes.

FIELD OF THE INVENTION

The present invention generally relates to biochemistry. In particular, the present invention relates to the method of treating heart diseases by targeting Tjp1.

BACKGROUND OF THE INVENTION

Modern sedentary life style, diet, increasing life expectancy and the raise of diseases like diabetes have resulted in an explosion of patients suffering from cardiovascular diseases including acute myocardial infarction (AMI). Contemporary treatment, including angioplasty, stenting and adjunctive drug therapy, has reduced early mortality from AMI. However, local 28-day AMI case-fatality in 2010 markedly exceeded the 2009 OECD average (12.7 vs 7.9%) despite exceptional adherence to guidelines-recommended treatment. One reason for these comparatively poorer outcomes may be heart failure (HF) after AMI. During AMI, billions of heart muscle cells or cardiomyocytes (CM) are lost and replaced with fibroblasts to form a collagen-rich scar tissue. This scar is not contractile and will further weaken the heart through compensatory mechanisms and additional CM loss, eventually leading to HF and death. The inability of the adult heart to adequately regenerate after injury leaves worldwide millions suffering from the results of AMI, with the associated mortality being a particular concern. Therapeutic approaches allowing survival or replacement of lost CMs after MI would thus be of tremendous economic and social impact. In view of the above problems, there is a need to provide an alternative method for treating a heart disease in a subject.

SUMMARY OF THE INVENTION

In one aspect, there is provided a method for treating a heart disease in a subject comprising the step of administering to the subject a therapeutically effective amount of Tjp1 inhibitor. In one embodiment, the Tjp1 inhibitor is a nucleic acid. In one embodiment, the nucleic acid is selected from the group consisting of an siRNA, an shRNA, an antisense oligonucleotide, a gapmers, and a short hairpin Antisense Oligonucleotide (shAON). In one embodiment, the nucleic acid binds to mRNA which encodes Tjp1 and forms a nucleic acid-mRNA complex. In one embodiment, the mRNA in the nucleic acid-mRNA complex is cleaved and/or is not translated. In one embodiment, the nucleic acid encoding the inhibitor has at least 90% identity to a sequence selected from the group consisting of SEQ ID NO:1 (CCGGGCCTGCATACAATAAAGCAAACTCGAGTTT-GCTTTATTGTATGCAGGCTTT TTG), SEQ ID NO:2 (CCGGGGAACCACTCTATCAAGTATTCTCGAGAATA-CTTGATAGAGTGGTTCCTTT TTG), SEQ ID NO: 3 (CCGGCGTGGATTGAACTTACTAAATCTCGAGATTT-AGTAAGTTCAATCCACGTTT TTG), and SEQ ID NO: 4 (CCGGCCGCGAAGTTATGAGCAAGTTCTCGAGAAC-TTGCTCATAACTTCGCGGTT TTTG).

In one embodiment, the method further comprises administering an additional factor selected from the group consisting of a polypeptide and a nucleic acid together or separately with the Tjp1 inhibitor. In one embodiment, the nucleic acid is encoding Cyclin A2. In one embodiment, the polypeptide binds to ErbB4 receptors. In one embodiment, the polypeptide binding ErbB4 receptors is selected from the group consisting of Neuregulin-1, Neuregulin-2 (NRG2), Neuregulin-3 (NRG3), Betacellulin (BTC), Epiregulin (EPR), Heparin Binding EGF-like Growth Factor (HB-EGF), Epidermal Growth Factor (EGF), β-Cellulin, Transforming Growth Factor Alpha (TGFα), and Amphiregulin (AR). In one embodiment, the polypeptide binding ErbB4 receptors is Neuregulin-1 (NRG1). In one embodiment, the polypeptide activates Wnt signaling. In one embodiment, the polypeptide activating Wnt signaling is selected from the group consisting of Wnts, Norrin, and R-spondin. In one embodiment, the polypeptide is a growth factor or a secreted factor. In one embodiment, the growth factor is Fibroblast Growth Factor (FGF) or Vascular Endothelial Growth Factor (VEGF). In one embodiment, the secreted factor is Follistatin-like 1 (Fstl1).

In one embodiment, wherein when the inhibitor is a nucleic acid inhibitor, the method comprises a virus-mediated delivery system. In one embodiment, the virus is selected from the group consisting of a retrovirus, an adenovirus, an adeno-associated virus, and a herpes simplex virus. In one embodiment, the virus is an adeno-associated virus. In one embodiment, the adeno-associated virus is AAV serotype 9.

In another aspect, there is provided use of a Tjp1 inhibitor in the manufacture of a medicament for treating a heart disease. In one embodiment, the heart disease is selected from the group consisting of myocardial infarct, acute myocardial infarction (AMI), heart failure, cardiomyopathy, congenital heart disease, acquired cardiovascular disease, cardiomyocytes deficiency, cardiac ischemic reperfusion injury, cardiac trauma, and other cardiac injury in a patient where heart cells regeneration is beneficial.

In yet another aspect, there is provided a patch, wherein the patch comprises the Tjp1 inhibitor as defined herein.

In yet another aspect, there is provided a nucleic acid encoding a Tjp1 inhibitor, wherein the nucleic acid has at least 90% identity to a sequence selected from the group consisting of SEQ ID NO:1 (CCGGGCCTGCATA-CAATAAAGCAAACTCGAGTTTGCTTTATTGTATGC-AGGCTTT TTG), SEQ ID NO:2 (CCGGGGAACCACTC-TATCAAGTATTCTCGAGAATACTTGATAGAGTGGTT-CCTTT TTG), SEQ ID NO: 3 (CCGGCGTGGATT-GAACTTACTAAATCTCGAGATTTAGTAAGTTCAAT-CCACGTTT TTG), and SEQ ID NO: 4 (CCGGCCGC-GAAGTTATGAGCAAGTTCTCGAGAACTTGCTCATA-ACTTCGCGGTT TTTG).

BRIEF DESCRIPTION OF THE DRAWINGS

The invention will be better understood with reference to the detailed description when considered in conjunction with the non-limiting examples and the accompanying drawings, in which:

FIG. 1A shows a Western blot analysis for expression of Tjp1 on lysates of control (Ctrl; Tjp1$^{F/F}$ Myh6-Cre$^{ERT2}$) and two independent Tjp1 cKO hearts from tamoxifen induced mice; GAPDH was used as loading control. Three control and six Tjp1 cKO mice were analyzed and blots from a representative experiment are shown. FIG. 1B shows a pair of photographs depicting immunohistochemistry results of control and Tjp1cKO hearts. Sections of control and Tjp1 cKO hearts were stained with antibodies to Tjp1 (as indicated by arrows) and DAPI (as indicated by arrowheads). Localization of Tjp1 to the intercalated disc in the control heart and its efficient loss from the Tjp1 cKO heart were observed. Three control and 3 Tjp1 cKO mice were analyzed and a representative experiment is shown. FIG. 1C shows a photograph depicting histochemical result for the detection of LacZ expression. Tjp1 cKO (Tjp1$^{F/F}$ Myh6-Cre$^{ERT2}$)mice were crossed with a lacZ reporter line and given daily intraperitoneal tamoxifen (tamoxifen) injections for 5 days to induce Cre expression. LacZ expression detected as indirect evidence for activation of Cre expression. A representative experiment for one of three analyzed Tjp1 cKO mice is shown. FIG. 1D shows a photograph depicting the result of hematoxylin and eosin (H&E) staining. Control and Tjp1 cKO hearts were harvested 1 or 7 days post tamoxifen induction, sectioned and stained with H&E. Loss of Tjp1 did not lead to gross histological changes. Three control and Tjp1 cKO mice each were examined for each time point and images from a representative experiment are shown. FIG. 1E shows a pair of photographs depicting histochemical result of apoptotic cells detection. Control and Tjp1 cKO hearts were harvested 1, 3, 7 and 30 days post tamoxifen induction, sectioned and processed for Tunel staining to detect apoptotic cells. Nuclei were stained with DAPI. No apoptosis was detected at 1 day post tamoxifen induction and similar results were obtained in hearts collected 3, 7 and 30 days post tamoxifen induction (data not shown). Three control and three Tjp1 cKO mice were examined for each time point. Images from a representative experiment are shown. FIG. 1F shows a pair of photographs comparing the heart sizes of Control and Tjp1 cKO mice. Control and Tjp1 cKO mice were induced with tamoxifen for 5 days. The hearts were dissected and photographed 7 days post tamoxifen induction. FIG. 1G shows a bar graph depicting heart to body weight ratio of the control and Tjp1 cKO mice. Body weight (in gram) and heart weight (in gram) were determined and the ratio calculated and plotted. Thus, FIG. 1 illustrates that after inactivation of Tjp1 in CMs, the Tjp1 cKO hearts do not show gross abnormalities or apoptosis. However heart size and the heart to body weight ratio of Tjp1 cKO hearts are slightly higher when compared to control.

FIG. 2A shows a pair of photographs depicting histochemical result of Edu incorporation. Control and Tjp1 cKO mice were induced for 5 days with tamoxifen and 1 hour before sacrificing they were injected with Edu intraperitoneally. Hearts were harvested and sections stained to reveal nuclei with Edu incorporation (as indicated by arrows), indicative of proliferating cells. Nuclei were stained with DAPI (as indicated by arrowheads). FIG. 2B shows a bar graph depicting quantification of Edu- and DAPI-positive nuclei in sections of heart. Edu- and DAPI-positive nuclei were counted and the percentage of Edu-positive nuclei was calculated and plotted. Six control and six Tjp1 cKO mice were used. Ten views were taken from each heart. FIG. 2C shows a set of Western blots depicting expression of proliferation and cell cycle markers. Lysates of control and two Tjp1 cKO hearts were collected 1 day after the last tamoxifen induction and analyzed by Western blot for expression of the indicated cell cycle regulatory proteins. GAPDH was used as a loading control. Two control and four Tjp1 cKO mice were analysed and blots from a representative experiment are shown. FIG. 2D shows a pair of photographs depicting histochemical result of fibrosis detection. Control and Tjp1 cKO hearts were harvested 3, 7 and 30 days post tamoxifen induction, sectioned and processed for Masson's Trichrome staining to detect fibrosis. Despite massive cell proliferation, no fibrosis was detected and similar results were obtained in hearts collected 7 and 30 days post induction (data not shown). Three control and Tjp1 cKO mice each were examined and data from a representative experiment is shown. FIG. 2E shows a pair of photographs depicting immunohistochemistry result of detection of Edu- and MHC-positive cardiomyocytes (CMs). Control and Tjp1 cKO mice were induced for 5 days with tamoxifen. Edu was injected via intra peritoneal for 3 days after tamoxifen induction. Hearts were harvested and sections co-labeled to detect Edu incorporation and the CM maker MHC. Arrows point to MHC-positive CMs clearly associated with Edu-positive nuclei, consistent with proliferation. Nuclei were stained with DAPI. FIG. 2F shows a bar graph depicting quantification of Edu-positive MHC-positive cells. Edupositive nuclei associated with MHC-positive myocardial cells and total Edu-positive nuclei were counted and the percentage of Edu-positive MHC-positive cells was calculated and plotted. Five control and five Tjp1 cKO mice were used. Ten views were taken from each heart. Only Edu-positive nuclei that could unequivocally be associated with an MHC-positive cell were scored, thus the extent of CM proliferation is most likely underestimated. FIG. 2G shows a photograph depicting the dissociation of adult cardiomyocytes (CMs). Control and Tjp1 cKO mice were induced for 5 days with tamoxifen and then sacrificed 1 day later. Heart cells were dissociated and imaged by phase contrast microscopy. FIG. 2H shows a set of photographs depicting histochemical result of detection of mono- and multinucleated Edu-positive cardiomyocytes (CMs). Control and Tjp1 cKO mice were induced for 5 days with tamoxifen followed by 3 daily Edu injections and sacrificed one day later. Heart cells were dissociated and labeled for incorporated Edu (as indicated by arrows) and MHC (as indicated by asterisks). An example of a mono- and a di-nucleated MHC-positive CM is shown. Nuclei were labeled with DAPI (as indicated by arrowheads). FIG. 2I shows a bar graph depicting quantification of mono or multinucleated Edu-positive MHC-positive cells. Mono or multinucleated Edu-positive MHC-positive cells and total MHC-positive cells were counted and the fraction of mono- or di-nucleated Edu-positive CMs determined and plotted. FIG. 2J shows a bar graph depicting quantification of Edu-positive cardiomyocytes (CMs) at multiple time points. It was found that the fraction of Edu-positive CMs does not change over time. Control and Tjp1 cKO mice were induced for 5 days with tamoxifen followed by 3 daily Edu injections. Mice were sacrificed 30 days later. Heart cells were dissociated and labeled for incorporated Edu and MHC. Mono or multinucleated Edu-positive MHC-positive cells and total MHC-positive cells were counted and the fraction of mono or di-nucleated Edu-positive CMs determined and plotted. FIG. 2K shows a bar graph depicting quantification of total Edu-positive heart cells at multiple time points. It was found that the fraction of total Edu-positive heart cells decreases over time. Control and Tjp1 cKO mice were induced with tamoxifen for 5 days and then injected intraperitoneally with Edu for 3 days. One, 25, and 137 days after the 3 day Edu pulse, hearts were collected and processed to detect incorporated Edu. Gradual decline of Edu-positive cells was observed. FIG. 2L shows a bar graph depicting the heart to body weight ratio measured after 137 days. It was found that heart to body weight ratio normalizes over time. Body weight (in gram) and heart weight (in gram) were determined and the ratio calculated and plotted. Thus, FIG. 2 illustrates that Tjp1 deletion induced cell proliferation because Edu-positive nuclei were abundant in the Tjp1cKO heart, higher level of markers for mitosis and enhanced cell proliferation were observed, and fibrosis was not observed.

FIG. 3A shows a set of photographs depicting histochemical result of the observation of sarcomere structure. Control and Tjp1 cKO mice were induced with tamoxifen for 5 days and hearts were harvested 1 or 7 days later. Hearts were sectioned, stained for MHC and imaged at 640× or 1600× magnification. The disorganized sarcomere structure at 1-day post induction and the recovery at day 7 was observed. Nuclei were labeled with DAPI. Three control and three Tjp1 cKO mice were analyzed for each time point and data from a representative experiment is shown. FIGS. 3B and 3C show a set of photographs depicting immunohistochemistry results that indicate that some Edu-positive cells express the cardiomyocyte (CM) progenitor marker, Gata-4. Control and Tjp1 cKO mice were induced for 5 days with tamoxifen. Edu was pulsed for 1 hour before sacrifice 1 day after tamoxifen induction. Control and Tjp1 cKO hearts were sectioned and stained to detect incorporated Edu and Gata-4 (FIG. 3B) or Nkx2.5 (FIG. 3C). Arrows point to Edu-positive and Gata-4- or Nkx2.5-positive nuclei. Nuclei were labeled with DAPI. FIGS. 3D and 3E show a pair of bar graph depicting quantification of Edu-positive Gata-4- or Nkx2.5-positive nuclei. Edu-positive Gata-4- or Nkx2.5-positive nuclei and Edu-positive nuclei were counted and the percentage of Edu-positive Gata-4-positive (FIG. 3D) or Edu-positive Nkx2.5-positive (FIG. 3E) cells was calculated and plotted. Three control and three Tjp1 cKO mice were used. FIG. 3F shows a set of Western blots depicting expression of early cardiac progenitor and de-differentiation markers. Control and two Tjp1 cKO hearts collected 1 day after tamoxifen induction were lysed and analyzed by Western blot for expression of different markers for dedifferentiation. GAPDH was used as a loading control. Two control and four Tjp1 cKO mice were analyzed and blots from a representative experiment are shown. Despite the enhanced nuclear expression of Gata-4 observed by immunohistochemistry (see FIG. 3C), it was observed that protein levels were not increased, suggesting enhanced nuclear relocalization from the cytosol. Thus, FIG. 3 illustrates increase of the levels of proteins related to heart development signifying that CMs undergo partial dedifferentiation after Tjp1 deletion.

FIG. 4A shows a set of Western blots depicting expression of various markers that indicate activation of different signaling pathways. Lysates of control and two Tjp1 cKO hearts from tamoxifen induced mice were collected one day after the last tamoxifen injection and processed to analyze expression of the indicated markers for activation of different signaling pathways. GAPDH was used as a loading control. Two control and four Tjp1 cKO mice were analyzed and data from a representative experiment is presented. FIG. 4B shows a set of Western blots depicting the effect of the Mek inhibitor PD0325901 on signaling. Control and Tjp1 cKO mice were induced with tamoxifen, with or without co-injection of PD0325901, daily for 5 days and hearts collected one day after the last injection and processed for Western blot analysis. Three pairs of control and Tjp1 cKO animals were analyzed. Panels form a representative experiment is shown. FIG. 4C shows a set of photographs depicting the immunohistochemistry result that illustrate the effect of the Mek inhibitor PD0325901 on nuclear pErk and pStat3. Hearts were obtained as described on FIG. 4B and were processed for immunohistochemistry to detect pErk or pStat3. FIG. 4D shows a set of photographs depicting immunohistochemistry result illustrating that inhibition of the Mek-Erk pathway blocks cell proliferation. Control and Tjp1 cKO mice were induced with tamoxifen daily for 5 days, with or without co-injection of PD0325901. One day after the last induction, Edu was injected one hour before sacrificing mice. Hearts were labeled to detect incorporated Edu (as indicated by arrows) and nuclei (DAPI, as indicated by arrowheads). FIG. 4E shows a bar graph depicting quantification of Edu-positive nuclei in hearts with or without exposure to PD0325901. Percentage of Edu-positive nuclei in hearts with or without exposure to PD0325901 were determined and plotted. Six Tjp1 cKO mice that were treated or not treated with the Mek were used. Ten views were taken from each heart. FIGS. 4F, 4G, and 4H shows a set of bar graphs depicting quantification of the effect of the Stat3 inhibitor S31-301, Akt inhibitor API-2, and Wnt inhibitor LGK974 on cell proliferation in the Tjp1 cKO heart. Percentage of Edu-positive nuclei in hearts with or without exposure to S31-301 (FIG. 4F), API-2 (FIG. 4G), or LGK974 (FIG. 4H) were determined (see FIG. 7) and plotted. Five (API-2) or six (S31-201, LGK974) Tjp1 cKO mice, which were treated or not treated with the different inhibitors, were used. Ten views were taken from each heart. Thus, FIG. 4 illustrates that inhibition of components involved in various signaling pathways confirms that activation of those signaling pathways drives cell proliferation upon Tjp1 deletion.

FIG. 5A shows a set of Western blots that illustrate the effect of the EGF/ErbB receptor inhibitor Ast1306 on signaling. Control and Tjp1 cKO mice were induced with tamoxifen, with or without co-injection of Ast1306, daily for five days. The hearts were collected one day after the last injection and processed for Western blot analysis. Three pairs of control and Tjp1 cKO mice were injected with the Mek inhibitor and were examined. Blots from a representative experiment are shown. FIG. 5B shows a pair of photographs depicting immunohistochemistry result illustrating that inhibition of the EGF/ErbB receptor blocks cell proliferation. Control and Tjp1 cKO mice were induced with tamoxifen daily for five days, with or without co-injection of Ast1306. One day after the last induction, Edu was injected one hour before sacrificing mice. Hearts were labeled to detect incorporated Edu (as indicated by arrows) and nuclei (DAPI, as indicated by arrowheads). FIG. 5C shows a bar graph depicting quantification of Edu-positive nuclei in hearts with or without exposure to Ast1306C. Percentage of Edu-positive nuclei in hearts with or without exposure to Ast1306 were determined and plotted. Six Tjp1 cKO mice that were treated or not treated with Ast1306 were used. Ten views were taken from each heart. FIG. 5D shows a set of Western blots illustrating that deletion of Tjp1 increases total ErbB4 protein levels and activated ErbB4 protein levels in the heart. Lysates of control and Tjp1 cKO hearts from tamoxifen induced mice were collected one day after the last tamoxifen injection and were processed to analyze expression of ErbB4 or activated pErbB4. GAPDH was used as a loading control. Two control and four Tjp1 cKO mice were analysed and data from a representative experiment is shown. FIG. 5E shows a set of photographs depicting immunohistochemistry result illustrating that the absence of Tjp1 enhances the stimulatory effect of Nrg1 on cell proliferation in the adult heart. Control and Tjp1 cKO mice were induced with tamoxifen daily for 5 days. Three weeks later, mice were injected with Edu and vehicle or Nrg1 daily for 5 days. One day after the last injection, hearts were harvested and sectioned stained to detect incorporated Edu (as indicated by arrows) and nuclei (DAPI, as indicated by arrowheads). FIG. 5F shows a bar graph depicting quantification of edu-positive nuclei in control or Tjp1 cKO hearts with or without exposure to Nrg1. Percentage of Edu-positive nuclei in control or Tjp1 cKO hearts with or without exposure to Nrg1 were determined and plotted. Six control and six Tjp1 cKO mice were used for each group. Ten views were taken from each heart. FIG. 5G shows a set of Western blots illustrating that silencing Tjp1 enhances and sustains Nrg1 mediated Erk activation and stabilizes ErbB4 protein levels. Control or Tjp1 shRNA treated MCF-7 cells were incubated with Nrg1 for the indicated periods of time. Cells were then lysed and processed for Western blot analysis. GAPDH was used as loading control. FIG. 5H shows a set of Western blots illustrating that silencing Tjp1 sensitizes cells to Nrg1 stimulation. Control or Tjp1 shRNA treated MCF-7 cells were incubated with various Nrg1 concentrations indicated and then lysed and processed for Western blot analysis. GAPDH was used as loading control. Ligand-stimulation and dose-response experiments were repeated at least three times. Data from a representative experiment is shown. FIG. 5I shows a set of amino acid sequences comparing the PDZ-binding motifs in the C-termini of ErbB2 and Erb4. FIG. 5J shows a set of Western blots illustrating that the ZO-1 (Tjp1) PDZ domains bind ErbB4 but not a mutant lacking the C-terminal PDZ binding motif. GST or a GST fusion protein carrying the three PDZ domains of Tjp1 (GST-Tjp1 PDZ1-3) was incubated with lysates from cells overexpressing ErbB4 or a mutant lacking the PDZ binding motif (ErbB4 ΔPBM). Bound proteins were eluted and detected by Western blot using anti-ErbB4 antibodies. Aliquots of cell lysate (10 µg) were run as controls (input) and GST or GST-Tjp1 PDZ1-3 fusion proteins were visualized by staining the membrane with Ponceau stain. FIG. 5K shows a set of Western blots illustrating that the ZO-1 (Tjp1) PDZ domains bind ErbB2. GST or a GST fusion protein carrying the 3 PDZ domains of Tjp1 (GST-Tjp1 PDZ1-3) or the closely related Tjp2 (GST-Tjp2 PDZ1-3) or Tjp3 (GST-Tjp3 PDZ1-3) were incubated with lysates from cells overexpressing ErbB2. Bound proteins were eluted and detected by Western blot using anti-ErbB2 antibodies. Aliquots of cell lysate (10 µg) were run as controls (input) and GST or GST-Tjp1 PDZ1-3 fusion proteins were visualized by staining the membrane with Ponceau stain. GST-binding experiments were carried out at least 3 times and data from a representative experiment is shown. Thus, FIG. 5 illustrates that Tjp1 has an inhibitory role on Nrg1-mediated ErbB4 signaling in the heart. Therefore, silencing of Tjp1 (e.g. shRNA-mediated silencing of Tjp1) sustained Nrg1-induced ErbB4 signaling and thereby promotes CM proliferation.

FIG. 6A shows a pair of photographs depicting immunohistochemistry result illustrating MI induced fibrosis in control and Tjp1 cKO hearts. MI was induced by permanent ligation of the left anterior descending coronary artery. After surgery, Tjp1 deletion was induced by daily tamoxifen injection for 5 days. Hearts were collected one week later, sectioned and stained with Masson's Trichrome to visualize Fibrosis. Based on Masson's Trichromes staining result, the control and Tjp1 cKO heart showed similar staining intensities, thereby indicating that the surgery to induce MI resulted in a similar initial damage to the control and Tjp1 cKO heart. FIG. 6B shows a set of photographs depicting immunohistochemistry result illustrating CM proliferation in the MI border region. Following induction of MI and tamoxifen induction as described above, Edu was administered daily for three days and mice were sacrificed. Control or Tjp1 cKO hearts were labeled to detect incorporated Edu and MHC to identify CMs. Nuclei were labeled with DAPI. Arrows point to Edu-positive MHC-positive cells, indicating more proliferating CMs in the Tjp1 cKO infarct border region. Large number of MHC negative nuclei in the infarcted tissue, presumably fibroblasts responsible for the fibrotic scar formation, was observed. FIGS. 6C and 6D show bar graphs depicting quantification of Edu- and MHC-positive cells of the control and Tjp1 cKO hearts. Edu- and MHC-positive cells in the MI border area of control and Tjp1 cKO hearts were counted and normalized to MI border area (FIG. 6C). More than 10 views were taken from each heart. Alternatively, Edu- and MHC-positive cells and total Edu-positive cells were counted in the MI border region and a remote non-infarcted area and the fraction of Edu-positive CMs determined and plotted (FIG. 6D). Ten views were taken from each heart. FIGS. 6E, 6F, 6G, and 6H show a bar graph and several scatter plots illustrating the result of heart function analysis. Following MI and tamoxifen induction, echocardiograms were recorded to estimate initial infarct size (FIG. 6E). Recordings at the indicated time intervals were used to calculate end diastolic volume (EDV; FIG. 6F), left ventricular ejection fraction (LVEF, FIG. 6G) and infract border zone wall thickness (FIG. 6H). Seven control and eight Tjp1 cKO mice were monitored. Data points for the control mice are indicated using black squares and data points for the Tjp1cKO mice are indicated using grey squares with white asterisks. FIG. 6I shows a graphical illustration of a model for illustrating the role of Tjp1 in modulating CM proliferation. In the adult heart, Tjp1 suppresses ErbB2/ErbB4 signaling and activation of the downstream effectors Erk, Akt, Stat3 and Wnt signaling. Deletion of Tjp1 results in partial CM dedifferentiation and release of para/autocrine factors. The lack of Tjp1 also sensitizes ErbB2/ErbB4 to Nrg1 or other ligands, which may be present in the tissue or are released in response to Tjp1 deletion and/or MI, to drive CM proliferation via activation of Erk, Akt, Stat3 and Wnt signaling. Thus, FIG. 6 illustrates that deleting of Tjp1 after MI leads to enhanced CM proliferation, in particular in the scar border region, limiting adverse remodeling and preserving heart function.

FIG. 7A shows a set of Western blots that illustrate the effect of the Stat inhibitor S31-20 on signaling. Control and Tjp1 cKO mice were induced with tamoxifen, with or without co-injection of S31-20, daily for five days. Hearts were collected one day after the last injection and processed for Western blot analysis. FIG. 7B shows a set of photographs depicting immunohistochemistry result illustrating the effect of the Stat3 inhibitor S31-20 on nuclear pStat3 and pErk levels. Hearts obtained as described on FIG. 7A were processed for immunohistochemistry to detect pErk or pStat3. FIG. 7C shows a pair of photographs depicting immunohistochemistry result illustrating that the inhibition of the Stat3 pathway blocks cell proliferation. Control and Tjp1 cKO mice were induced with tamoxifen daily for five days, with or without co-injection of S31-20. One day after the last induction, Edu was injected one hour before sacrificing mice. Hearts were labeled to detect incorporated Edu (as indicated by arrows) and nuclei (DAPI, as indicated by arrowheads). The result of the quantification is depicted on FIG. 4F. FIG. 7D shows a set of Western blots that illustrate the effect of the Akt inhibitor API-2 on signaling. Control and Tjp1 cKO mice were induced with tamoxifen, with or without co-injection of API-2, daily for five days. Hearts were collected one day after the last injection and were processed for Western blot analysis. FIG. 7E shows a pair of photographs depicting immunohistochemistry result illustrating that inhibition of the Akt pathway partially blocks cell proliferation. Control and Tjp1 cKO mice were induced with tamoxifen daily for five days, with or without co-injection of API-2. One day after the last induction, Edu was injected one hour before sacrificing mice. Hearts were labeled to detect incorporated Edu (as indicated by arrows) and nuclei (DAPI, as indicated by arrowheads). The result of the quantification is depicted on FIG. 4G. FIG. 7F shows a set of Western blots that illustrate the effect of the Wnt inhibitor LGK974 on signaling. Control and Tjp1 cKO mice were induced with tamoxifen, with or without co-injection of LGK974, daily for five days. Hearts were collected one day after the last injection and processed for Western blot analysis. FIG. 7G shows a pair of photographs depicting immunohistochemistry result illustrating that the inhibition of the Wnt pathway partially blocks cell proliferation. Control and Tjp1 cKO mice were induced with tamoxifen daily for five days, with or without co-injection of LGK974. One day after the last induction, Edu was injected one hour before sacrificing mice. Hearts were labeled to detect incorporated Edu (as indicated by arrows) and nuclei (DAPI, as indicated by arrowheads). The result of the quantification is depicted on FIG. 4H. Thus, FIG. 7, similar to FIG. 4, illustrates that inhibition of Stat3, Akt, and Wnt, suppressed cell proliferation in the Tjp1 cKO heart.

FIG. 8A shows a set of Western blots that illustrate effect of shRNAs targeting Tjp1 in the expression of Tjp1/ZO-1. Murine Hepa1-6 cells were transfected with different shRNAs targeting Tjp1 (TJP1#1, TJP1#2) or a non-targeting control shRNA (NT) and the effect on Tjp1/ZO-1 expression was determined by Western blot analysis. FIG. 8B shows a set of shRNA sequences. Sequences for TJP1#1 (mTJP1 shRNA#1; SEQ ID NO: 3) and TJP1#2 (mTJP1 shRNA#2; SEQ ID NO: 4) are shown. Thus, FIG. 8 shows that mouse Tjp1 can be silenced using shRNA that targets Tjp1.

DETAILED DESCRIPTION OF THE PRESENT INVENTION

Figure 1:
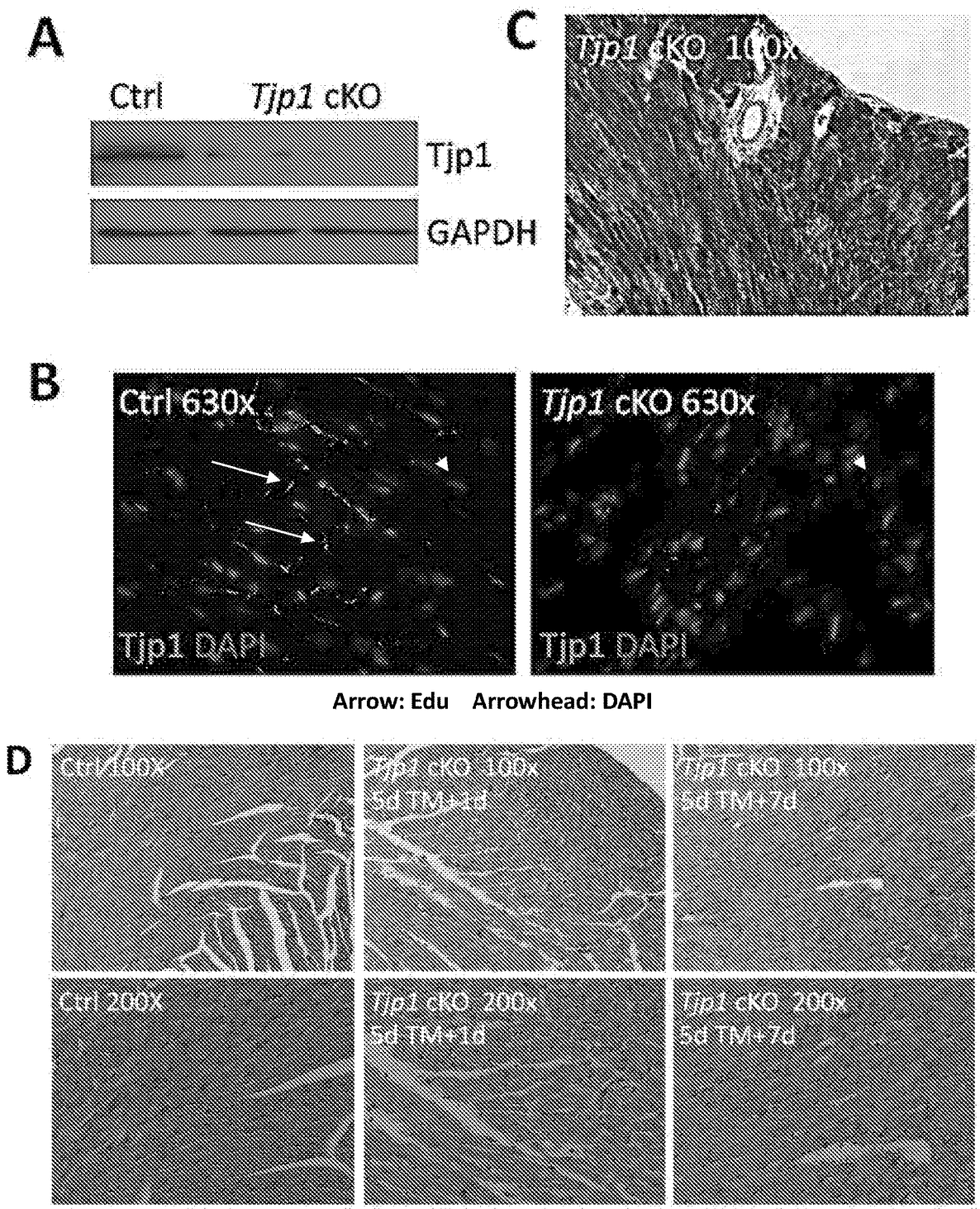
FIG. 1 shows a set of experimental results that illustrate efficient inducible deletion of Tjp1 in cardiomyocytes (CMs).
Figure 1:
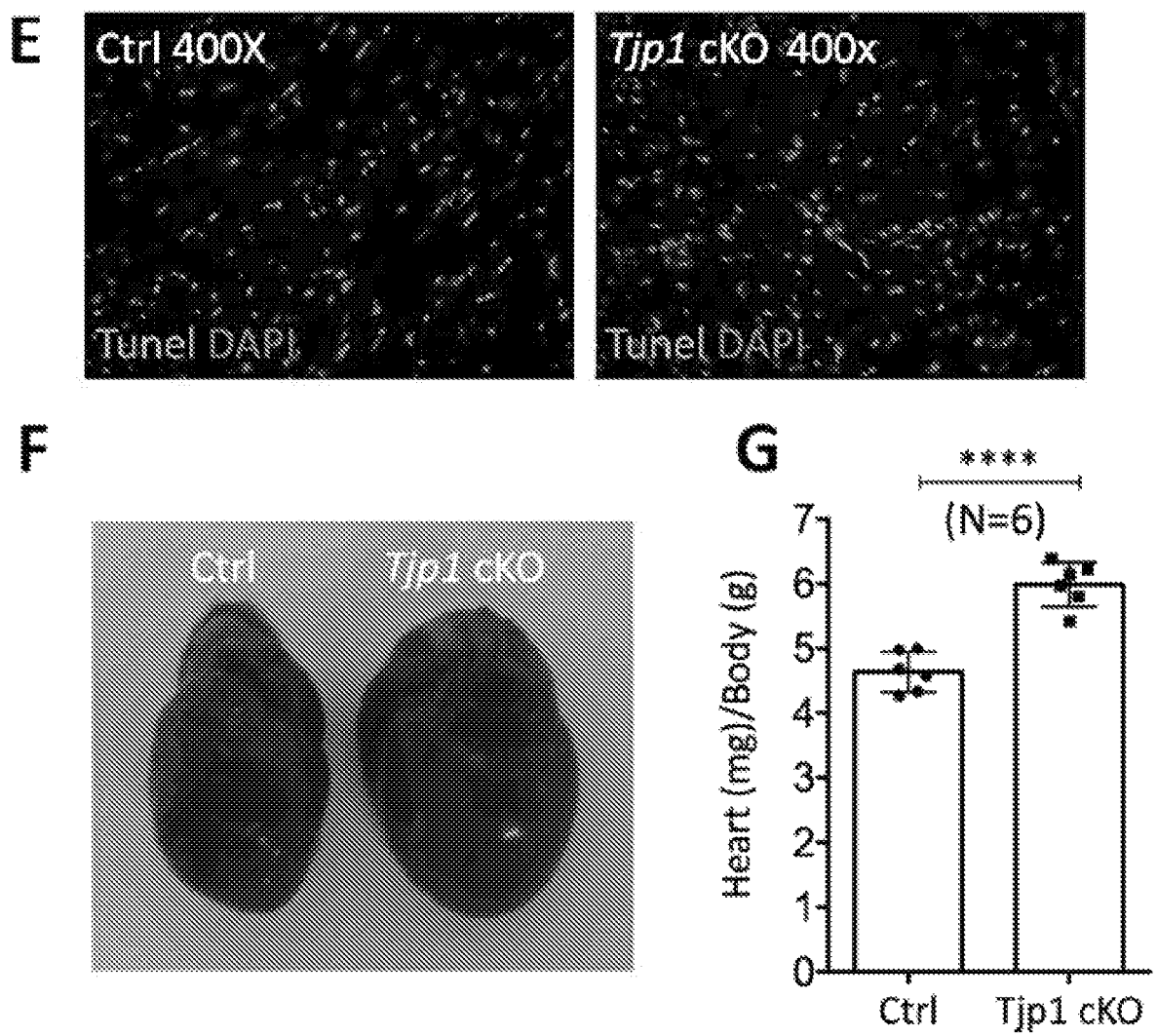

Heart diseases are the leading cause of hospitalization and mortality in adult humans worldwide. In the United States, for example, heart failure results in 1 out of 4 deaths. Congenital or acquired cardiovascular disease results in cardiomyocyte (CM) deficiency, which usually leads to heart failure and death. Heart failure (HF) can also ensue following myocardial infarction (MI) when cardiomyocytes (CMs) are irrecoverably lost and replaced by fibrosis. Despite benefits from blockade of the renin-angiotensin-aldosterone and sympathetic systems, outcomes in HF remain dismal, with a 5-year survival of only 50%. Unlike in human, in some other vertebrates, the heart has an intrinsic regenerative capacity. After resection of up to 20% of the ventricle, zebrafish can regenerate the lost tissue within 2 months. Regeneration is achieved by dedifferentiation and proliferation of pre-existing CMs. In mammals, the heart of newborn mice possesses a regenerative capacity that is lost within 7 days after birth. In adult mice and other mammals, however, heart injury result in scar tissue formation and loss of CM and heart function.

A major challenge in heart regeneration is the fact that human adult heart cells (such as human adult cardiomyocytes) have limited proliferative capacity. The lack of proliferative capacity of heart cells following MIs is problematic because it can affect restoration of cardiac function and prevention of HF following MI. In view of the above, there is a need to provide an alternative method for treating a heart disease in a subject and to induce the proliferation of heart cells.

The inventors of the present disclosure have found an alternative method for treating a heart disease in a subject. Thus, in one aspect, the present invention provides a method for treating a heart disease in a subject comprising the step of administering to the subject a (therapeutically effective amount of) Tjp1 inhibitor. It was surprisingly found that administration of a Tjp1 inhibitor inhibits Tjp1 expression. This inhibition leads to an inhibition of Tjp1 activity and thus induces proliferation of heart cells. Thus, in another aspect, the present invention provides a method for proliferating heart cells in a subject in need thereof comprising the step of administering to the subject a (therapeutically effective amount of) Tjp1 inhibitor. In some example, the subject has had a heart disease. Without being bound by theory, this proliferation of heart cells after myocardial infarction prevents or reduces formation of scar tissue by stimulating regeneration of heart cells, in particular cardiomyocytes. The method of inhibition of Tjp1 described herein is useful to induce proliferation of cardiomyocytes in human who have suffered from heart diseases.

As used herein the term Tjp1 (Tight Junction Protein 1) and ZO-1 (Zonula Occludens-1) are used interchangeably. The terms "Tjp1" and "ZO-1" refers to an actin-binding scaffold protein that in cardiomyocytes localizes to the intercalated disc. As used herein, the term "heart cells" refers to cell types that form the structure of a heart. The examples of heart cells include, but are not limited to, cardiomyocytes, fibroblasts cells, epicardium cells, endothelial cells, smooth muscle cells, and the like. The term "heart cells" does not refer to cell types that do not form the structure of a heart such as blood cells. Thus, in one example, the Tjp1 inhibitor described herein further induces proliferation of cells which include, but are not limited to, cardiomyocytes, fibroblast cells, epicardium cells, endothelial cells, smooth muscle cells, and the like. In one example, the cells which proliferation is induced by the Tjp1 inhibitor described herein are cardiomyocytes. In one example, the cardiomyocytes are mature or differentiated cardiomyocyte cells. In one example, the inventor has surprisingly observed that upon administration of Tjp1 inhibitor, the cardiomyocyte cells de-differentiate into immature cardiomyocyte and exhibit a regenerative phenotype.

A person skilled in the art will appreciate that the list of regenerative phenotypes included herein is not exhaustive. Examples of regenerative phenotypes include, but are not limited to, disorganized sarcomere structure, upregulation of Dab2 (Disabled-2), upregulation of Myh7 (Myosin Heavy Chain 7), upregulation of Destrin, upregulation of Runx1 (Runt Related Transcription Factor 1), upregulation and/or redistribution of transcriptional regulators (such as GATA4 (GATA Binding Protein 4) or Nkx2.5 (NK2 Homeobox 5)) from the cytoplasm to the nucleus, DNA replication (e.g. as indicated by Edu (5-ethynyl-2'-deoxyuridine) positive staining), and/or downregulation of Myh6 (Myosin Heavy Chain 6). As used herein, the term "upregulation" or "downregulation" refers to increase or decrease in comparison to a level before Tjp1 inhibition. Increased expression at mRNA and/or protein levels of, for example Myh7, Dab2, Destrin, Runx1, indicates de-differentiation as they are embryonic CM markers. Myh6 is a mature CM marker, thus a decreased expression of Myh6 can also be taken as indication of de-differentiation.

Figure 3:
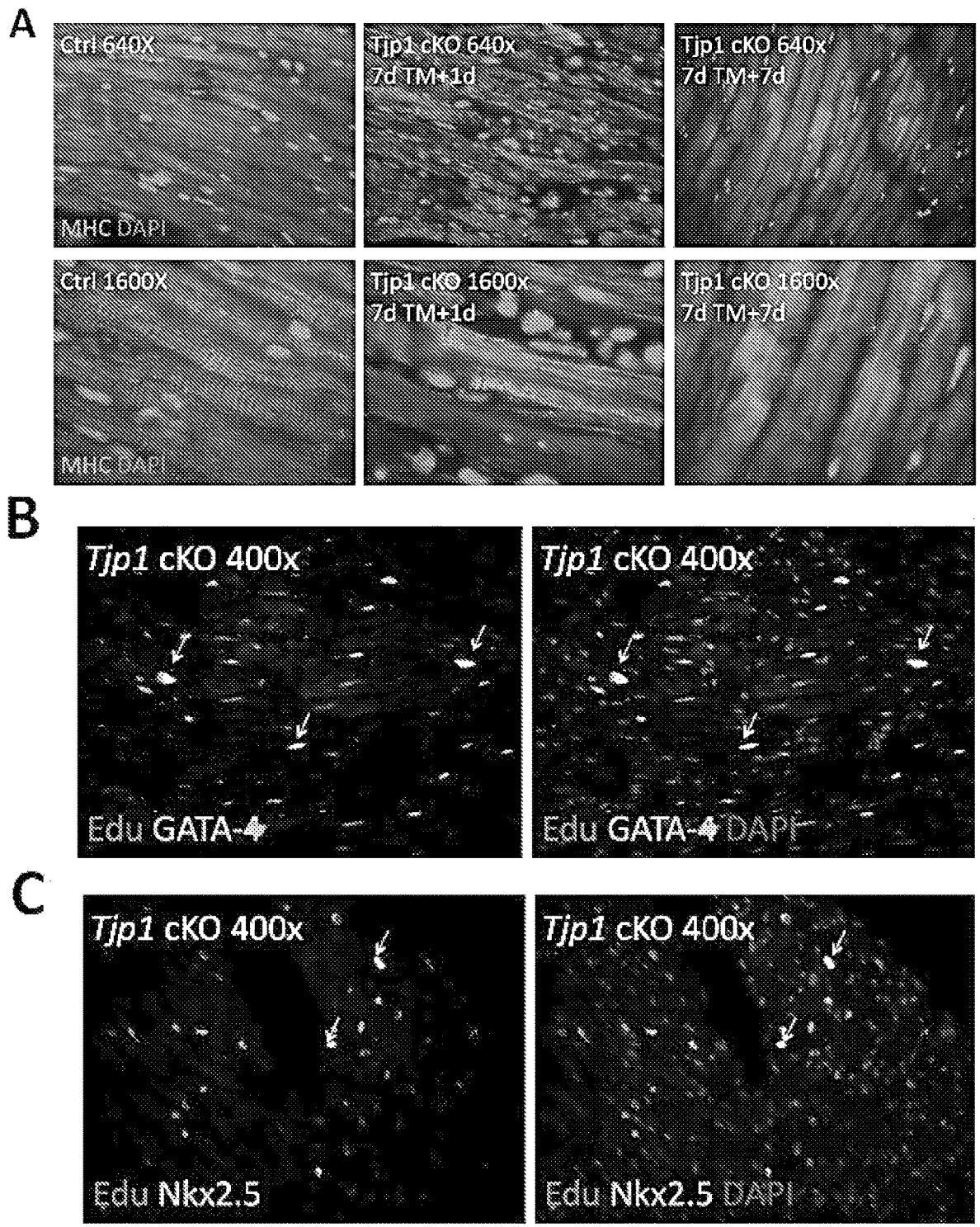
FIG. 3 shows a set of experimental results that illustrate the cardiomyocyte (CM) dedifferentiation after Tjp1 deletion.
Figure 3:
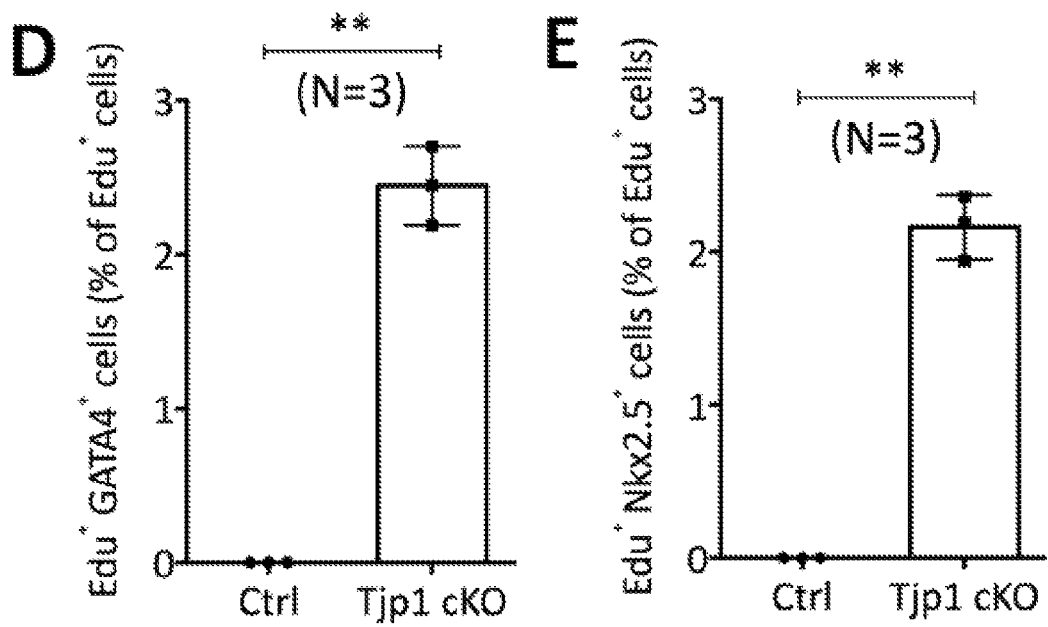
Figure 3:
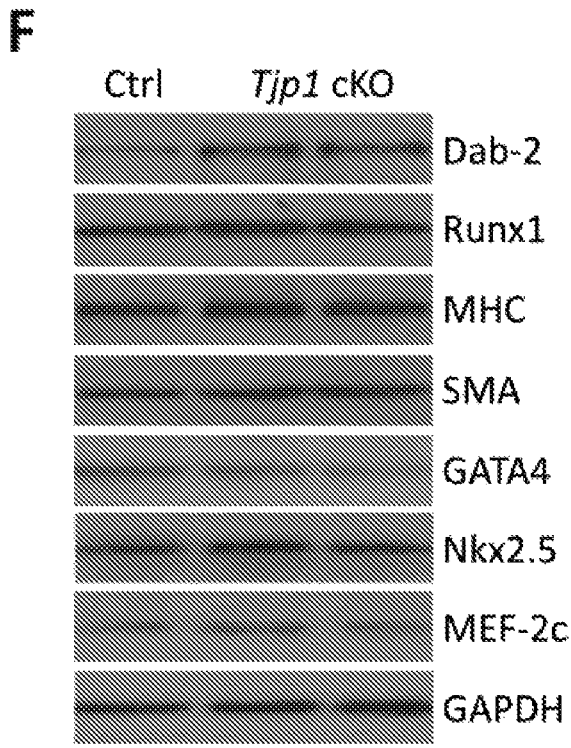

In one example, the regenerative phenotype that is exhibited when cardiomyocyte cells de-differentiate into immature cardiomyocytes includes, but is not limited to, at least one, or at least two, or at least three, or more of the regenerative phenotypes described herein. As shown for example on FIG. 3, changes to the levels of regenerative phenotype related to heart development signifying that CMs undergo partial dedifferentiation after Tjp1 deletion. In one example, said regenerative phenotypes include, but are not limited to, disorganized sarcomere structure, upregulation of Dab2, upregulation of Myh7, upregulation of Destrin, upregulation of Runx1, redistribution of transcriptional regulators (such as GATA4 or Nkx2.5) from the cytoplasm to the nucleus, DNA replication (for example as indicated by Edu positive staining), downregulation of Myh6, and the like.

In one example, the Tjp1 inhibitor described herein inhibits Tjp1 expression. The term "inhibit" is used herein generally to mean a decrease of the amount as compared to an untreated subject (or a patient to be treated) or a control. However, for avoidance of doubt, "inhibit" means a decrease sufficient to stimulate regeneration of heart cells, in particular cardiomyocytes. In one other example, inhibition means a decrease by at least 10% as compared to an untreated subject (or patient to be treated), or at least about 20%, or at least about 30%, or at least about 40%, or at least about 50%, or at least about 60%, or at least about 70%, or at least about 80%, or at least about 90% or up to and including a 100% decrease of Tjp1 expression as compared to an untreated subject (or patient to be treated), or any decrease between 10-100% of Tjp1 expression as compared to an untreated subject (or patient to be treated). As used herein, the term "control" refers to a population that is statistically similar to the set being tested, on which no changes are implemented. A non-limiting example of control as used herein is wild type mice (i.e. mice without Tjp1 knock-out).

It is believed that specific inhibition of Tjp1 on cardiomyoctyes would be sufficient to stimulate the proliferation of various cell types in the heart. In some examples, other than the expected autocrine or the secreted factors influences on cardiomyocytes (e.g. proliferation of cardiomyocytes per se), the deletion of Tjp1 also surprisingly induces paracrine or the secreted factors influences on non-cardiomyocytes (such as, but is not limited to, fibroblast). Thus, in one example, the cells which proliferation is induced by the Tjp1 inhibitor described herein are fibroblast.

Figure 5:
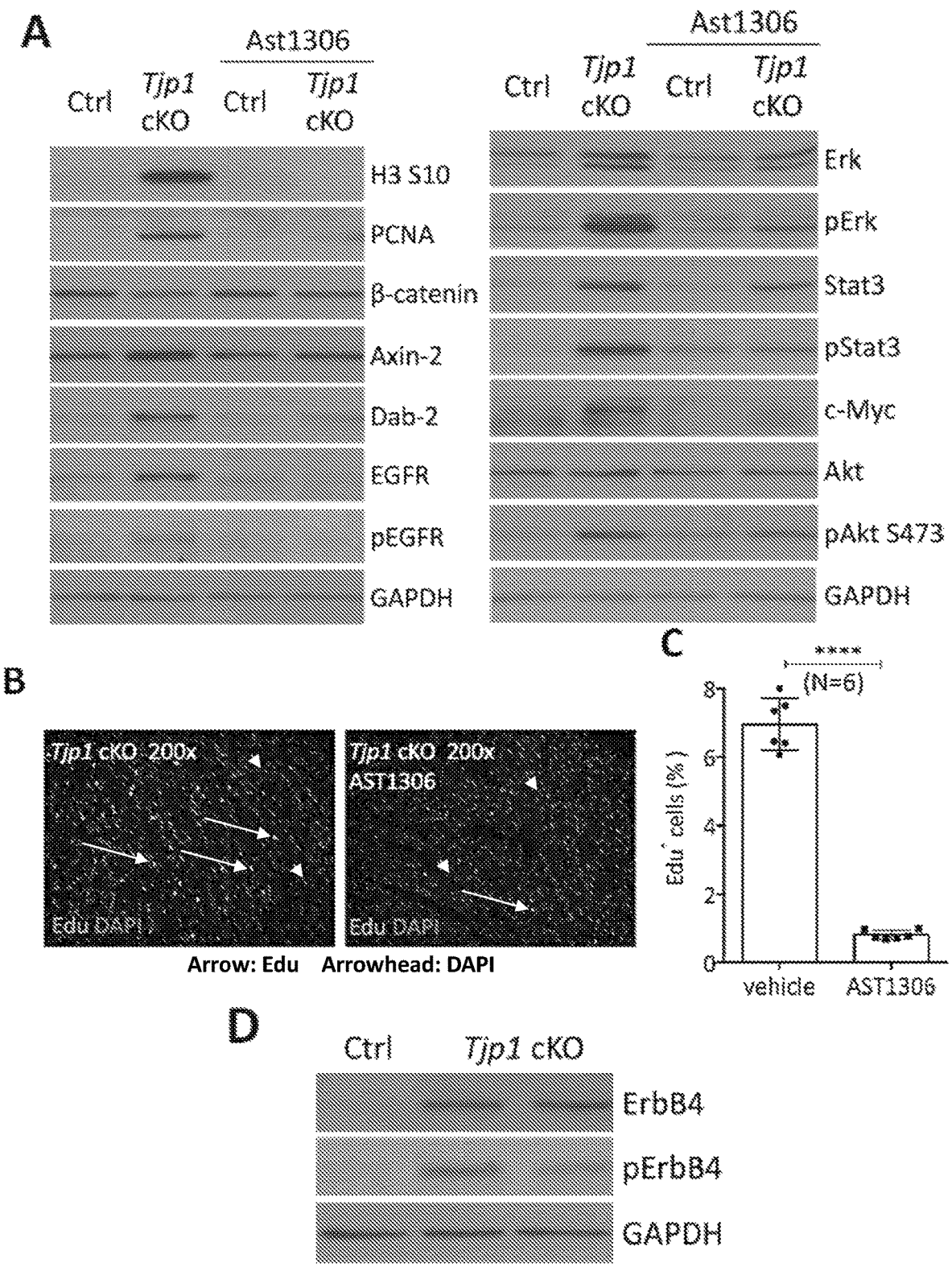
FIG. 5 shows a set of experimental results that illustrate that ErbB4 contributes to enhanced proliferation in the absence of Tjp1 and Tjp1 associates and suppresses ErbB4 signaling.
Figure 5:
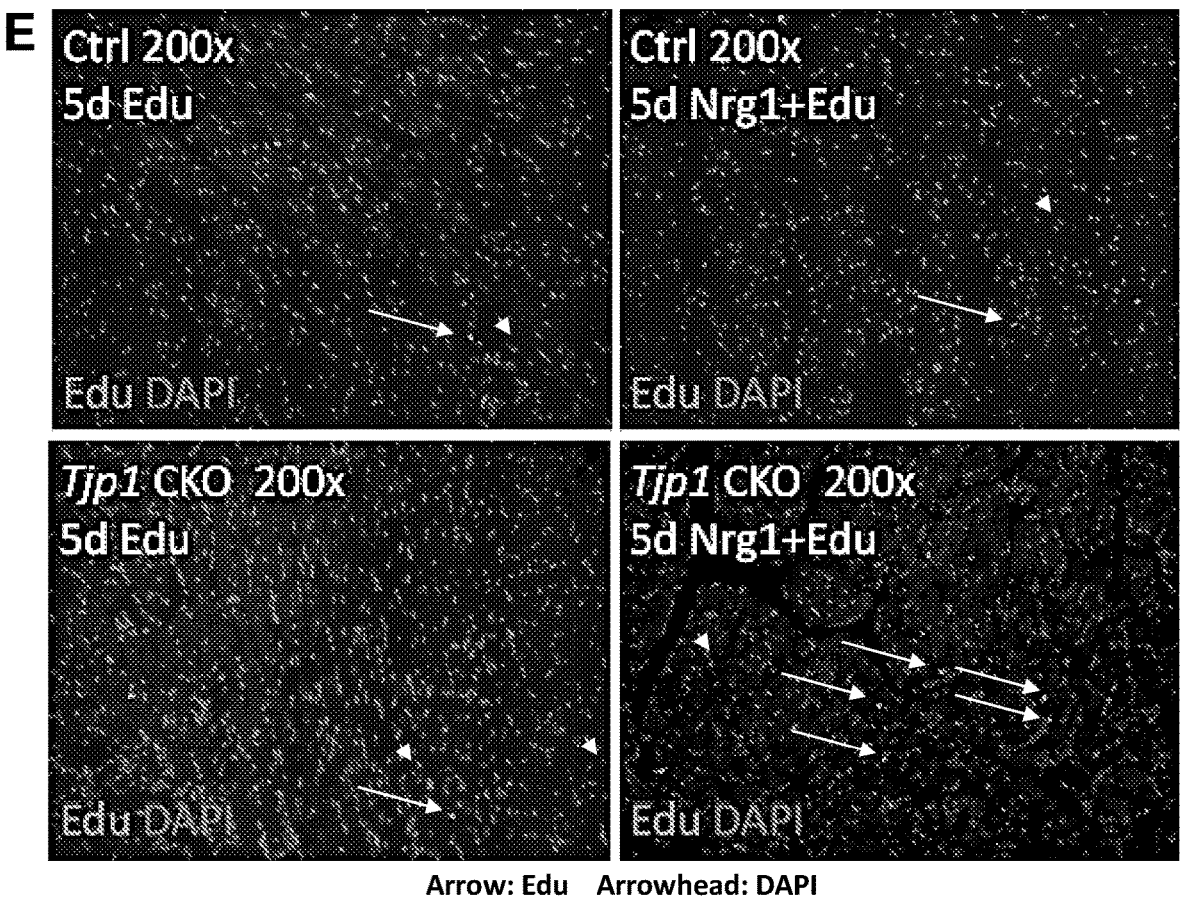
Figure 5:
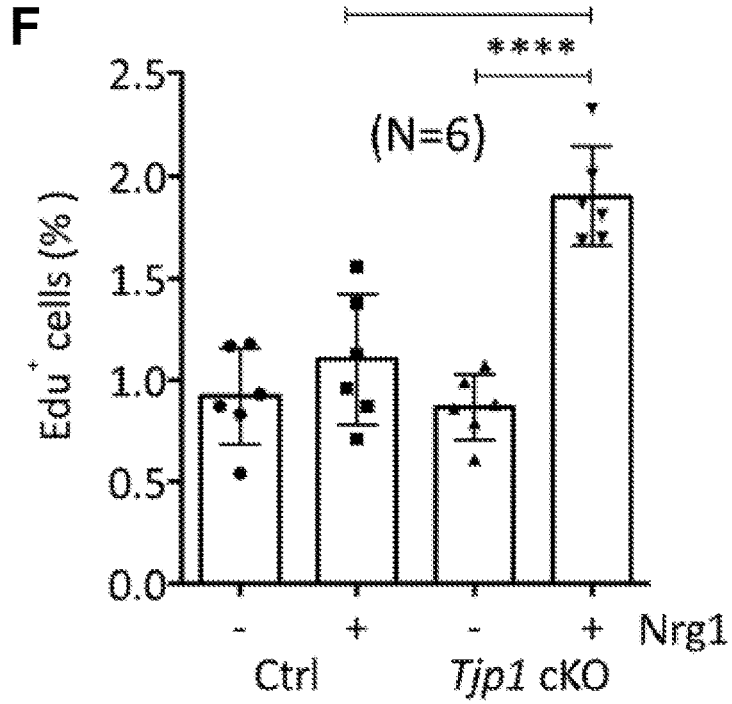
Figure 5:
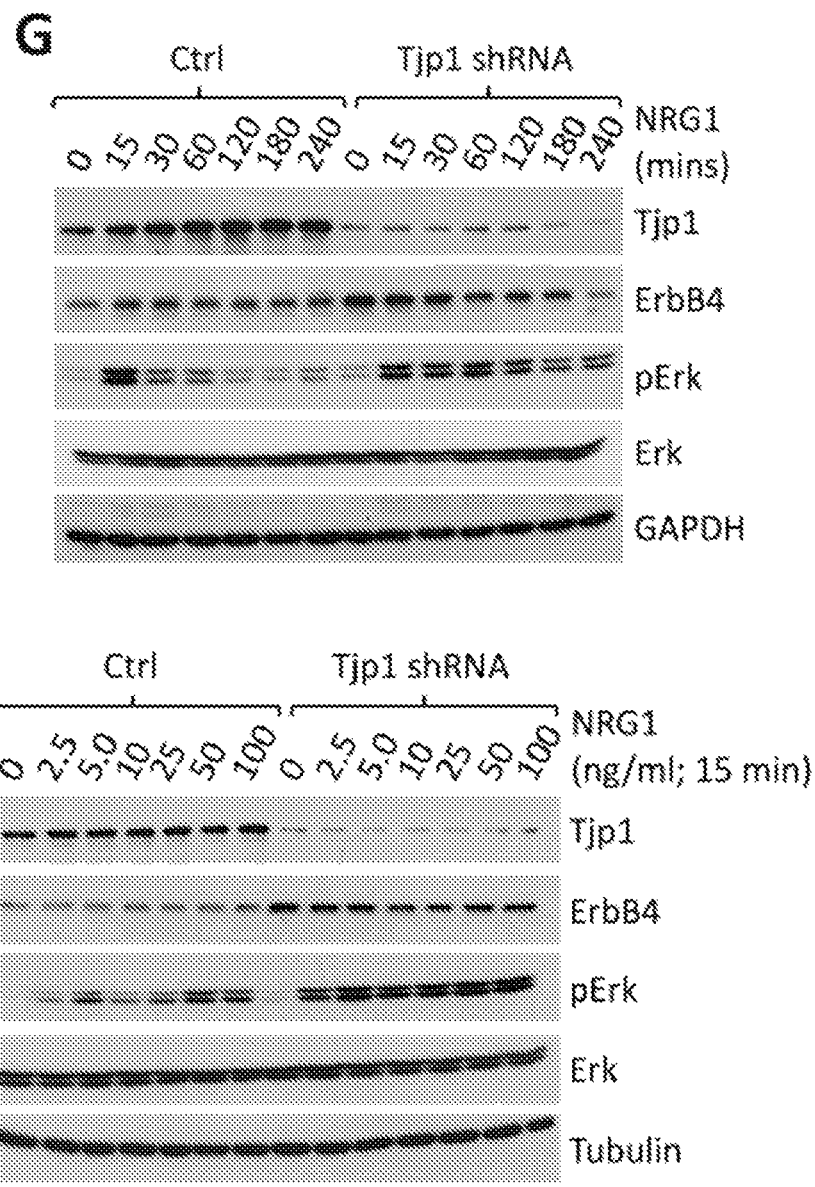
Figure 5:
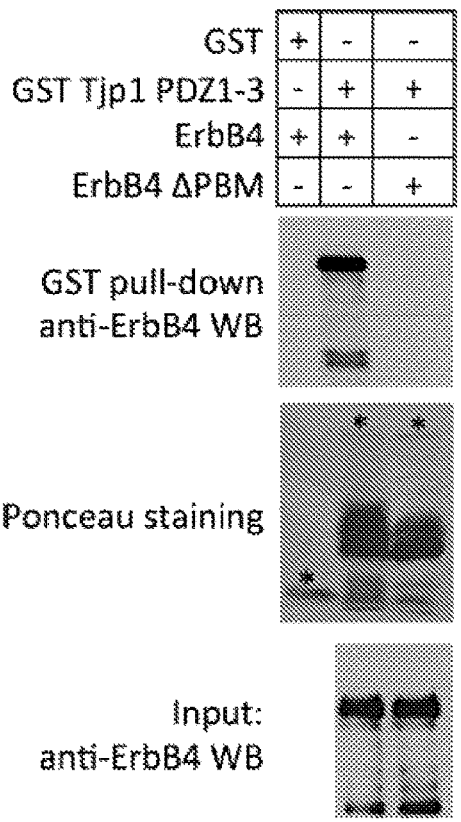
Figure 5:
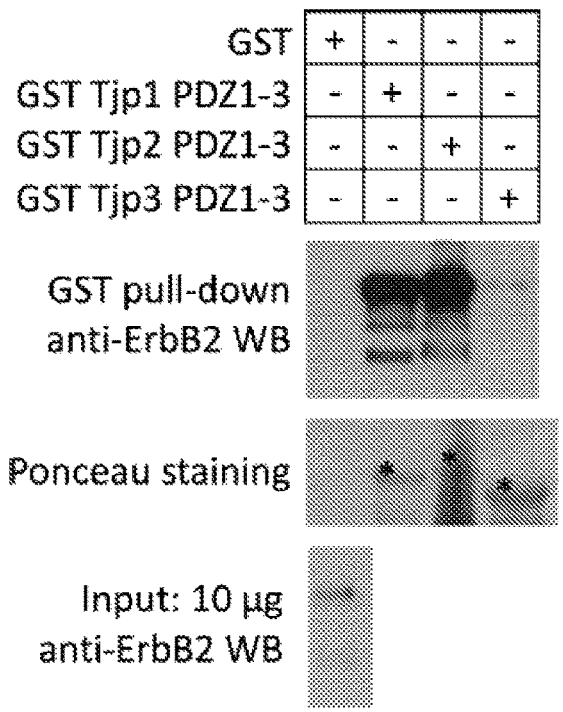

The inventors have surprisingly found that inhibition of Tjp1 expression activates multiple receptors. In one example, as shown for example in FIG. 5, Tjp1 has an inhibitory role on Nrg1-mediated ErbB4 signaling in the heart. Thus, in one example, the inhibition of Tjp1 expression enhances the surface expression of a or at least one receptor which includes, but is not limited to, ErbB1 receptor (EGF receptor), ErbB2 receptor, ErbB4 receptor, and the like.

Figure 4:
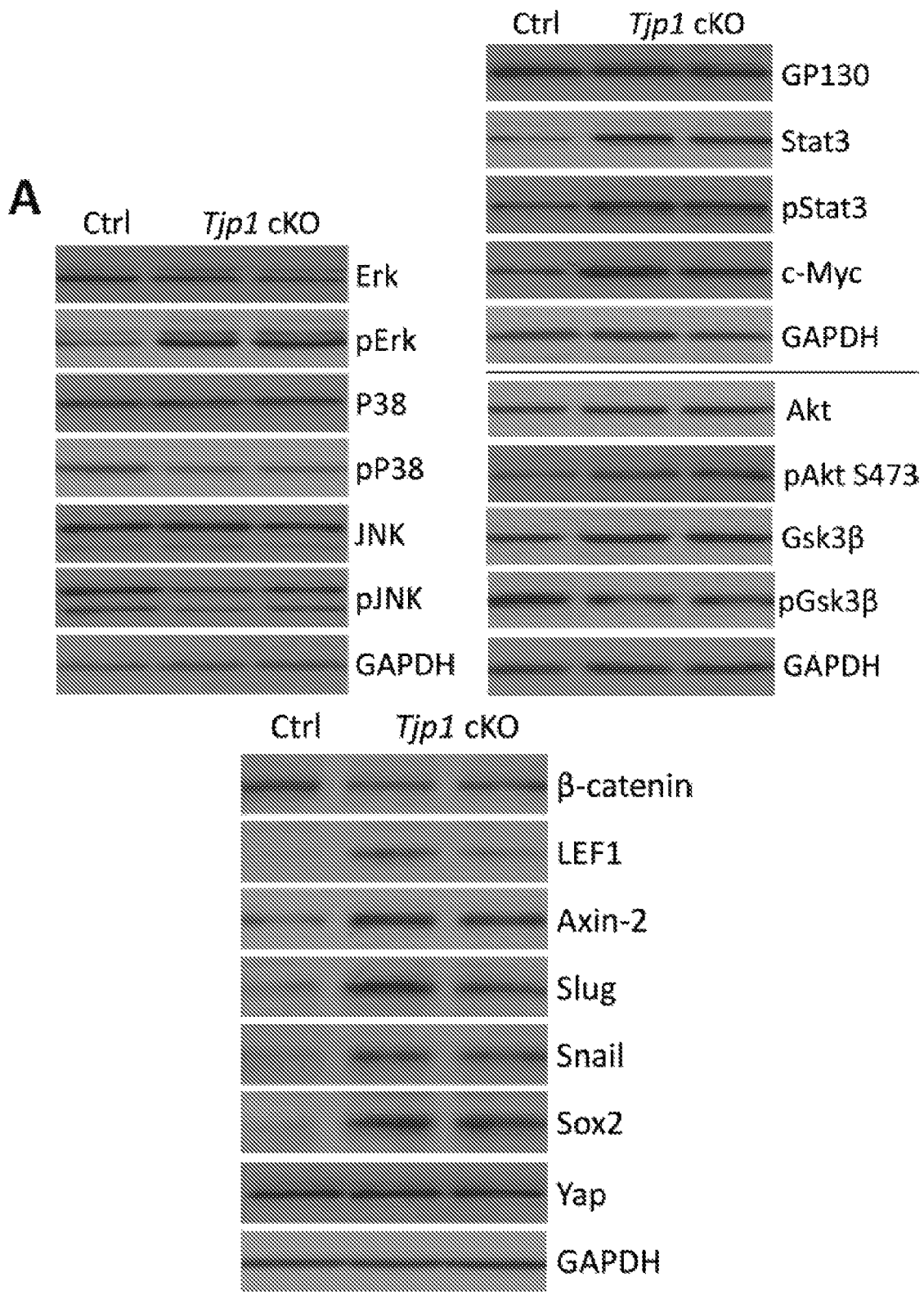
FIG. 4 shows a set of experimental results that illustrate that activation of Erk, Stat3, Akt and Wnt pathways in response to Tjp1 deletion contribute to cell proliferation in the adult heart.
Figure 4:
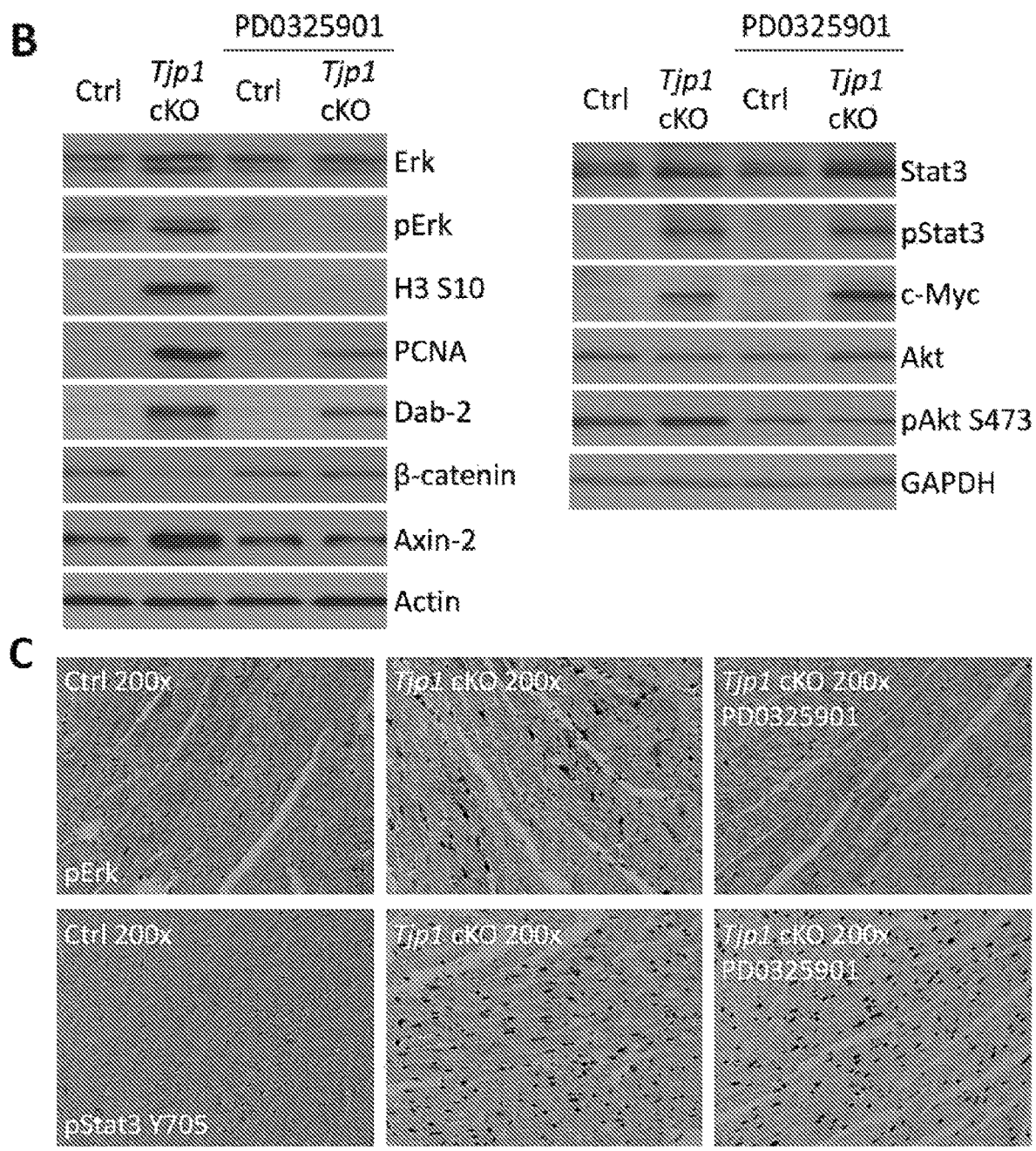
Figure 4:
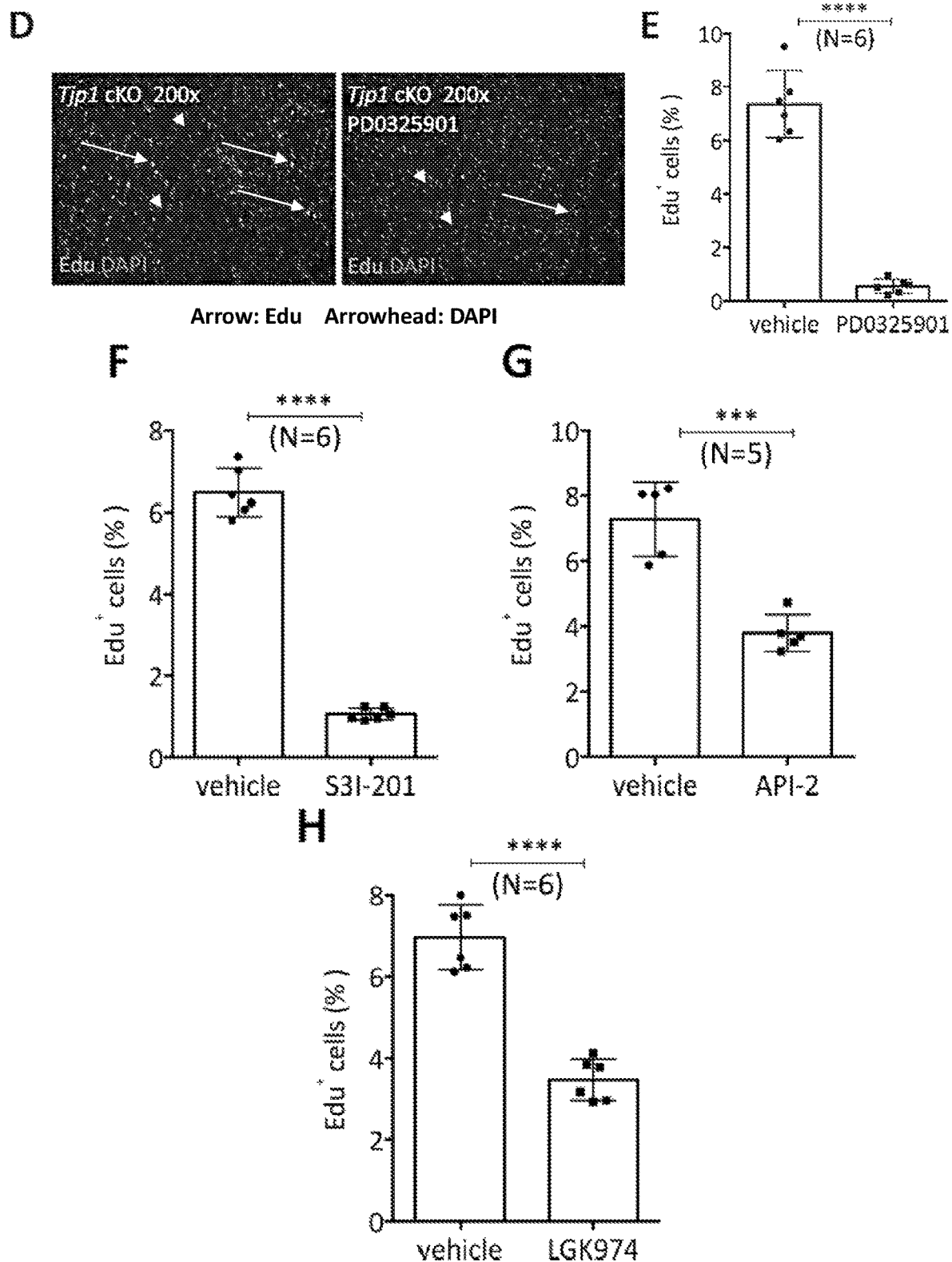

Besides inhibiting the Tjp1 expression, in one example, the Tjp1 inhibitor inhibits Tjp1 biological activity. The inventors have surprisingly found that inhibition of Tjp1 biological activity activates multiple signaling pathways. As shown for example in FIG. 4, Erk, Stat3, Akt and Wnt pathways are activated in response to Tjp1 deletion. Thus, in one example, the inhibition of Tjp1 biological activity activates at least one of the signaling pathways which includes but is not limited to mitogen-activated protein kinase (MAPKs) pathway, Stat3 signaling pathway, Akt signaling pathway, Wnt signaling pathway, Hippo pathway, and the like.

As described above, the inhibition of Tjp1 expression induces proliferation of heart cells. Therefore, controlling the duration of Tjp1 inhibition is important. Thus, in one example, the Tjp1 inhibitor is a transient (reversible or non-permanent) inhibitor or a permanent (irreversible) inhibitor. As used herein, the term "transient or reversible or non-permanent inhibitor" refers to inhibitor of Tjp1 that does not alter the genes of the heart cells and/or that can be readily removed from the target that the inhibitor binds to. As used herein, the term "permanent or irreversible inhibitor" refers to inhibitor of Tjp1 that alter the genes of the heart cells and/or that cannot be readily removed from the target that the inhibitor binds to. Non-limiting examples of permanent or irreversible inhibitor are inhibitors that target and genetically modify the genes of the heart cells. Targeting and modification of the genes can be implemented using any method known in the art which includes, but is not limited to, CRISPR/Cas9, TALEN, zinc finger nucleases, and the like.

A non-limiting example of permanent inactivation of Tjp1 (e.g. after Tjp1 deletion) is the Tjp1 cKO mouse described herein. However, it was also observed that Edu incorporation after deletion decreases over time thereby suggesting that Tjp1 can also be transiently inactivated. In one example, the Tjp1 inhibitor would be an inhibitor that inactivates Tjp1 expression or activity for a period of time sufficient to obtain an effect (e.g. regeneration of heart cells). After the desired effect has been obtained, the inhibitor is no longer required to inhibit Tjp1 expression or activity. A non-limiting example of an inhibitor that inactivates Tjp1 expression or activity in a time sufficient to obtain an effect is shRNA that is introduced using AAVs (adeno-associated viruses). The shRNA will remain as an episomal plasmid in cardiomyocytes and will be diluted out during cell proliferation or be subjected to natural turnover. Sequences introduced via AAV are known to remain active from weeks to over a year, which would be examples of timeframe required to stabilize heart function.

It would be appreciated that any methods known in the art to be capable of reducing or inactivating Tjp1 expression or activity would be suitable for use in the methods of the present disclosure. A person skilled in the art will appreciate that the list of the types of Tjp1 inhibitors included herein is not exhaustive. The examples of the types of Tjp1 inhibitors include, but are not limited to, a small molecule, an antibody, a polypeptide, a nucleic acid, and any other biological or chemical entity capable of inhibiting Tjp1 expression, function or activity. In one example, Tjp1 inhibitor includes, but is not limited to, a small molecule, an antibody, a polypeptide, a nucleic acid, and the like. A person skilled in the art will also appreciate that in some embodiments, the antibody that can be used as Tjp1 inhibitor is a monoclonal antibody, a polyclonal antibody, a recombinant antibody, a human antibody, a humanized antibody, a chimeric antibody, a multispecific antibody, or an antibody fragment thereof. In some examples, the antibody include, but is not limited to, a Fab fragment, a Fab' fragment, a F(ab')2 fragment, a Fv fragment, a diabody, or a single chain antibody molecule. In some examples, the antibody is a human antibody.

As would be appreciated by the person skilled in the art, nucleic acid sequences such as vectors, DNA inserts, shRNAs can be designed to target Tjp1. In one example, the nucleic acid that is used as Tjp1 inhibitor includes, but is not limited to, an siRNA, an shRNA, an antisense oligonucleotide, a gapmers, a short hairpin Antisense Oligonucleotide (shAON), and the like. In one example, when a nucleic acid is used as Tjp1 inhibitor, the nucleic acid may bind to or interacts with mRNA which encodes Tjp1 and forms a nucleic acid-mRNA complex. In one example, when the nucleic acid that is used as Tjp1 inhibitor bind to or interact with the mRNA that encodes the Tjp1 and form a nucleic acid-mRNA complex, the mRNA in the nucleic acid-mRNA complex is cleaved and/or is not translated.

The method of using of a nucleic acid as a Tjp1 inhibitor that binds to or interacts with the mRNA that encodes the Tjp1 is also known as "antisense oligonucleotide therapy". As used herein, the term "antisense oligonucleotide therapy" refers to the method to synthesize a strand of nucleic acid (such as DNA, RNA, a chemical analogue, and the like) that will bind to the messenger RNA (mRNA) produced by Tjp1 and inactivate it, effectively turning that gene "off". This is because mRNA has to be single stranded for it to be translated. "Antisense oligonucleotide therapy" also refers to the method to synthesize a strand of nucleic acid (such as DNA, RNA, a chemical analogue, and the like) that is targeted to bind to a splicing site on pre-mRNA, modify the exon content of an mRNA, and thus the mRNA will not be translated. A person skilled in the art would appreciate that the nucleic acid that is used as a Tjp1 inhibitor for the antisense oligonucleotide therapy includes, but are not limited to, shRNA, siRNA, morpholinos, and the like. The nucleic acid used for the antisense oligonucleotide therapy can be delivered with any manner known in the art. The delivery method of the nucleic acid used for the antisense oligonucleotide therapy includes, but is not limited to delivery method using adeno-associated viruses, delivery method using other viruses, delivery method using liposomes, delivery method by binding to aptamers for targeting, and the like.

A person skilled in the art would appreciate that the nucleic acid that is used as a Tjp1 inhibitor can be encoded using any nucleotide sequence. In one example, as shown for example on FIG. 5G, Western blot analysis has shown that Tjp1 can be silenced using shRNA that targets Tjp1. A person skilled in the art appreciates that the shRNA that targets Tjp1 are shRNA having sequences that are complementary to and/or that bind to the sequences of the cDNA and/or mRNA that encodes Tjp1. The shRNA that targets Tjp1 can be designed according to various methods that are known in the art. Thus, the shRNA that targets Tjp1 or the shRNA inhibitor can have any sequence and are not limited to the sequences listed herein. In one example, the nucleic acid encoding the Tjp1 inhibitor has at least 70% identity, or at least 75% identity, or at least 80% identity, or at least 85% identity, or at least 90% identity, or at least 95% identity, or at least 98% identity, or at least 99% identity, or at least 99.5% identity, to a sequence of SEQ ID NO:1 (CCGGGCCTGCATACAATAAAGCAAACTCGAGTTTGCTTTATTGTATGCAGGCTTT TTG), and/or SEQ ID NO:2 (CCGGGGAACCACTCTATCAAGTATTCTCGAGAATACTTGATAGAGTGGTTCCTTT TTG) and wherein the sequence still retains the ability to encode a Tjp1 inhibitor. In one example, the nucleic acid encoding the Tjp1 inhibitor has at least 70% identity, or at least 75% identity, or at least 80% identity, or at least 85% identity, or at least 90% identity, or at least 95% identity, or at least 98% identity, or at least 99% identity, or at least 99.5% identity, to a sequence of SEQ ID NO:3 (CCGGCGTGGATTGAACTTACTAAATCTCGAGATTTAGTAAGTTCAATCCACGTTT TTG), and/or SEQ ID NO: 4 (CCGGCCGCGAAGTTATGAGCAAGTTCTCGAGAACTTGCTCATAACTTCGCGGTT TTTG) and wherein the sequence still retains the ability to encode a Tjp1 inhibitor. In one example, the nucleic acid encoding the Tjp1 inhibitor has a sequence of SEQ ID NO:1 (CCGGGCCTGCATACAATAAAGCAAACTCGAGTTTGCTTTATTGTATGCAGGCTTT TTG), and/or SEQ ID NO:2 (CCGGGGAACCACTCTATCAAGTATTCTCGAGAATACTTGATAGAGTGGTTCCTTT TTG). In one example, the nucleic acid encoding the Tjp1 inhibitor has a sequence of SEQ ID NO:3 (CCGGCGTGGATTGAACTTACTAAATCTCGAGATTTAGTAAGTTCAATCCACGTTT TTG), and/or SEQ ID NO: 4 (CCGGCCGCGAAGTTATGAGCAAGTTCTCGAGAACTTGCTCATAACTTCGCGGTT TTTG).

In yet another aspect, the present invention provides a nucleic acid encoding a Tjp1 inhibitor, wherein the nucleic acid has at least 70% identity, or at least 75% identity, or at least 80% identity, or at least 85% identity, or at least 90% identity, or at least 95% identity, or at least 98% identity, or at least 99% identity, or at least 99.5% identity, to a sequence selected from the group consisting of SEQ ID NO:1 (CCGGGCCTGCATACAATAAAGCAAACTCGAGTTTGCTTTATTGTATGCAGGCTTT TTG), SEQ ID NO:2 (CCGGGGAACCACTCTATCAAGTATTCTCGAGAATACTTGATAGAGTGGTTCCTTT TTG), SEQ ID NO: 3 (CCGGCGTGGATTGAACTTACTAAATCTCGAGATTTAGTAAGTTCAATCCACGTTT TTG), and SEQ ID NO: 4 (CCGGCCGCGAAGTTATGAGCAAGTTCTCGAGAACTTGCTCATAACTTCGCGGTT TTTG), and wherein the sequence still retains the ability to encode a Tjp1 inhibitor. In one example, the present invention provides a nucleic acid encoding a Tjp1 inhibitor, wherein the nucleic acid has at least 70% identity, or at least 75% identity, or at least 80% identity, or at least 85% identity, or at least 90% identity, or at least 95% identity, or at least 98% identity, or at least 99% identity, or at least 99.5% identity, to a sequence selected from the group consisting of SEQ ID NO: 3 (CCGGCGTGGATTGAACTTACTAAATCTCGAGATTTAGTAAGTTCAATCCACGTTT TTG) and SEQ ID NO: 4 (CCGGCCGCGAAGTTATGAGCAAGTTCTCGAGAACTTGCTCATAACTTCGCGGTT TTTG), and wherein the sequence still retains the ability to encode a Tjp1 inhibitor.

As would be appreciated by the person skilled in the art, the nucleic acid sequences as disclosed herein (such as SEQ ID NO: 1 and/or SEQ ID NO: 2) are DNA inserts. In some examples, the nucleic acids (i.e. DNA inserts) are inserted into a vector (such as plasmid vector) from which the shRNA is generated. A person skilled in the art appreciate that the shRNA generated by a vector binds to the region in the mRNA of the target (for example mRNA that may be translated as Tjp1) that is complementary to the sequence of the shRNA generated. In one example, nucleic acid sequences as disclosed in SEQ ID NO: 1 and SEQ ID NO: 2 can be both inserted into a single vector thereby a single vector will express more than one shRNAs. Without wishing to be bound by theory, combination of multiple shRNAs may increase the inhibitory effects of shRNA on Tjp1 expression or activity. A person skilled in the art would appreciate that the nucleic acid that is used as a Tjp1 inhibitor can be expressed from a promoter derived from MHC or Tttn2, which would allow specific expression of the inhibiting nucleic acid in cardiomyocytes. In one example, the vector that is used to express Tjp1 inhibitor is an adeno associated virus (AAV) vector. AAV serotype 9 (AAV9) based vectors can efficiently transduce cardiomyocytes. In another example, an altered version of AAV termed self-complementary adeno-associated virus (scAAV) can be used to transduce the inhibitory nucleic acid. Whereas AAV packages a single strand of DNA and must wait for its second strand to be synthesized, scAAV packages two shorter strands that are complementary to each other. By avoiding second-strand synthesis, scAAV can express more quickly.

The inventors have also found that the efficacy of the Tjp1 inhibitor is improved when the inhibitor is administered with other factors. The inventors have observed that Tjp1 deletion itself activates Wnt signaling. Therefore, without wishing to be bound by theory, and as shown in example titled "Tjp1 deletion activates signaling pathways that drive CM proliferation", addition of Wnts, Norrin or R-Spondin appears to synergize with Tjp1 deletion. Thus, in one example, the Tjp1 inhibitor is administered with at least one, or at least two, or at least three, or at least four, or at least five, or more additional factor(s) which include, but are not limited to, small molecules (such as activators of Wnt signaling pathways), antibodies or fragments thereof, polypeptides (such as DARPin (Designed Ankyrin Repeat Protein)), nucleic acids (such as aptamers, single stranded RNA, and single stranded DNA), and the like. In one example, the Tjp1 inhibitor is administered together or separately with the Tjp1 inhibitor.

A person skilled in the art will appreciate that the list of factors can include fragments of these factors, antibodies, peptides, aptamers, darpins which can bind to ErbB receptors and in combination with Tjp1 inactivation, enhance ErbB receptor signaling. As will also be appreciated by a person skilled in the art, ErbB4 can homodimerize as well as heterodimerize with ErbB/Her2 and Tjp1 and/or Tjp2 can also bind ErbB 1/EgfR (which can homodimerize and heterodimerize with ErbB2/Her2) and ErbB2/Her2 (which can homopdimerize and heterodimerize with Her1EgfR, ErbB3 and ErbB4) and Tjp1 may therefore also regulate signaling through ligands that bind to these receptor combinations.

In one example, the nucleic acid that is administered with the Tjp1 inhibitor is a nucleic acid encoding for Cyclin A2. In one example, when the Tjp1 inhibitor is administered with polypeptide, the polypeptide includes, but is not limited to, a growth factor, a cytokine, a chemokine, a secreted factor, a stimulatory factor, and the like. In one example, when the Tjp1 inhibitor is administered with polypeptide, the polypeptide is a growth factor and/or a secreted factor (or secreted protein). As used herein, the term "stimulatory factors" refers to extracellular domains of ligand/receptors that are capable to stimulate adjacent cells (for example, Notch pathway).

In one example, the polypeptide that is administered with the Tjp1 inhibitor binds to ErbB4 receptors. In one example, the polypeptide that binds to the ErbB4 receptors and that is administered with the Tjp1 inhibitor includes, but is not limited to, Fibroblast Growth Factor (FGF), Vascular Endothelial Growth Factor (VEGF), Neuregulin-1, Neuregulin-2 (NRG2), Neuregulin-3 (NRG3), Betacellulin (BTC), Epiregulin (EPR), Heparin Binding EGF-like Growth Factor (HB-EGF), Epidermal Growth Factor (EGF), β-Cellulin, Transforming Growth Factor Alpha (TGFα), Amphiregulin (AR), and the like. In one example, the polypeptide that binds to the ErbB4 receptors and that is administered with the Tjp1 inhibitor is Neuregulin-1 (NRG1). In one example, the polypeptide that is administered with the Tjp1 inhibitor is a secreted factor. As used herein, the term "secreted factors" refers to factors that are secreted out of the cells. In one example, the secreted factor is Follistatin-like 1 (Fstl1). In one example, the polypeptide that is administered with the Tjp1 inhibitor activates Wnt signaling. In one example, the polypeptide that is administered with the Tjp1 inhibitor and activates Wnt signaling include, but are not limited to, Wnts, Norrin, R-spondin, and the like.

A person skilled in the art will appreciate that Tjp1 inhibitor may be administered using any delivery system known in the art and that the list of delivery system for the administration of the Tjp1 inhibitors listed herein is not exhaustive. The example of such delivery systems include, but are not limited to, a virus-mediated delivery system, a polymer-based delivery system, an implantable patch, a site specific delivery system (such as into perivascular space and adventitia via adventitial catheter), an injectable system (optionally combined with stent delivery system), an implantable release delivery system, and the like. In one example, wherein when the Tjp1 inhibitor is a nucleic acid inhibitor, the inhibitor is administered using systems which include, but are not limited to, a virus-mediated delivery system, a polymer-based delivery system, an implantable patch, a site specific delivery system (such as into perivascular space and adventitia via adventitial catheter), and the like.

A person skilled in the art will appreciate that the list of viruses for the administration of the Tjp1 inhibitors via virus-mediated delivery system listed herein is not exhaustive. The examples of such viruses include, but are not limited to a retrovirus, an adenovirus, an adeno-associated virus, a herpes simplex virus, and the like. In one example, wherein when the delivery system of the Tjp1 inhibitor is virus-mediated delivery system, the virus includes, but is not limited to, a retrovirus, an adenovirus, an adeno-associated virus, a herpes simplex virus, and the like. In one example, wherein when the delivery system of the Tjp1 inhibitor is virus-mediated delivery system, the virus is an adeno-associated virus. The adeno-associated virus that can be used for the delivery of Tjp1 inhibitor has a variety of serotype. In one example, the adeno-associated virus that is used for the delivery of Tjp1 inhibitor includes, but is not limited to AAV serotype 1, AAV serotype 2, AAV serotype 3, AAV serotype 4, AAV serotype 5, AAV serotype 6, AAV serotype 7, AAV serotype 8, AAV serotype 9, AAV serotype 10, AAV serotype 11, and the like. In one example, the adeno-associated virus that is used for the delivery of Tjp1 inhibitor is AAV serotype 9. In one example, wherein when the delivery system of the Tjp1 inhibitor is virus-mediated delivery system, the dosage of the inhibitor is from $4.00 \times 10^7$ vg/kg to $4.00 \times 10^{15}$ vg/kg, or from $4.00 \times 10^8$ vg/kg to $4.00 \times 10^{14}$ vg/kg, or from $4.00 \times 10^9$ vg/kg to $4.00 \times 10^{13}$ vg/kg, or from $4.00 \times 10^{10}$ vg/kg to $4.00 \times 10^{12}$ vg/kg, or about $4.00 \times 10^7$ vg/kg, or about $4.00 \times 10^8$ vg/kg, or about $4.00 \times 10^9$ vg/kg, or about $4.00 \times 10^{10}$ vg/kg, or about $4.00 \times 10^{11}$ vg/kg, or about $4.00 \times 10^{12}$ vg/kg, or about $4.00 \times 10^{13}$ vg/kg, or about $4.00 \times 10^{14}$ vg/kg, or about $4.00 \times 10^{15}$ vg/kg. As used herein, the term "vg/kg" refers to viral (or vector) genomes per kilogram body weight of the subject.

In one example, wherein when the Tjp1 inhibitor is a small molecule, an antibody, or a polypeptide, the delivery system includes, but is not limited to, localized delivery system, systemic delivery system, and the like. In one example, the localized delivery system for the Tjp1 inhibitor includes, but is not limited to, a polymer-based delivery system, an injectable system (optionally combined with stent delivery system), an adventitial catheter, an implantable release delivery system, and the like. In one example, the systemic delivery system for the Tjp1 inhibitor include, but is not limited to, an oral delivery system (i.e. oral formulations such as a capsule, a solution, a tablet, or the like), a suppository, intravenous delivery system, intraperitoneal delivery system, intramuscular delivery system, intradermal delivery system, subcutaneous injection, and the like. In one example, wherein when the Tjp1 inhibitor is a small molecule, an antibody, or a polypeptide, the dosage of the inhibitor is from 1 µg/kg to 1000 mg/kg, or 10 mg/kg to 100 mg/kg, or about 10 mg/kg, or about 20 mg/kg, or about 30 mg/kg, or about 40 mg/kg, or about 50 mg/kg, or about 60 mg/kg, or about 70 mg/kg, or about 80 mg/kg, or about 90 mg/kg, or about 100 mg/kg.

In order for the inventors to be able to provide an alternative method for treating a heart disease by administration of Tjp1 inhibitor and promoting proliferation of heart cells, there is a need to provide a method to identify active compounds. Thus, in another aspect, the present invention provides a method of identifying a compound capable of promoting cardiomyocyte proliferation, wherein the method comprises the steps of: (a) contacting the compound to a Tjp1 knock out host or to a host in which Tjp1 has been inhibited, and (b) observing the presence or absence of cardiomyocyte proliferation in the host, wherein the presence of cardiomyocyte proliferation indicates the compound to be capable of promoting cardiomyocyte proliferation. As used herein, the term "knock out" refers to partial or complete suppression of the expression of at least a portion of a Tjp1 encoded by an endogenous DNA sequence in a cell.

In yet another aspect, the present invention provides a method of identifying factors secreted in response to Tjp1 inhibition (with or without myocardial infarct), wherein the method comprises: (a) administration of Tjp1 inhibitor to a host or use of a Tjp1 knock out host (either with or without myocardial infarct induction), (b) collecting a sample from the host before and after step (a), and (c) determining factors secreted after step (a) to thereby identify the factors secreted in response to Tjp1 inhibition.

In one example, the host used in a method of identifying a compound capable of promoting cardiomyocyte proliferation or factors secreted in response to Tjp1 inhibition is a non-human mammalian host. In one example, the non-human mammalian host includes, but is not limited to, a mouse, a pig, a rat, a guinea pig, a hamster, a rabbit, a non-human primate, a cat, a dog, and the like. In one example, the non-human mammalian host is a mouse or a pig. In one example, the method of identifying a compound capable of promoting cardiomyocyte proliferation or factors secreted in response to Tjp1 inhibition is performed using an assay that includes, but is not limited to, an antibody array, an assay to identify and quantitate cytokines and signal transduction proteins (such as Luminex multiplex assay), and the like.

In yet another aspect, the present invention provides Tjp1 inhibitor for use in therapy. In yet another aspect, the present invention provides use of a Tjp1 inhibitor in the manufacture of a medicament for treating a heart disease. The Tjp1 inhibitor inhibits Tjp1 expression. The inhibition of Tjp1 expression can lead to inhibition of Tjp1 activity. Thus, inhibition of Tjp1 will ultimately induce proliferation of heart cells (for example, such as cardiomyocytes). In one example, the heart disease includes, but is not limited to, myocardial infarct, acute myocardial infarction (AMI), heart failure, cardiomyopathy, congenital heart disease, acquired cardiovascular disease, cardiomyocytes deficiency, cardiac ischemic reperfusion injury, cardiac trauma, cardiac disease that can be treated by regeneration of heart cells (such as cardiomyocytes) after myocardial infarct, and the like. In one example, the heart disease also includes other cardiac injury in a patient where regeneration of heart cells is beneficial.

In yet another aspect, the present invention provides a pharmaceutical composition comprising a Tjp1 inhibitor as described herein. In one example, the composition comprising a Tjp1 inhibitor is to be administered with at least one additional factor as described herein. In yet another aspect, the present invention provides a patch, wherein the patch comprises Tjp1 inhibitor as described herein. In one example, the patch comprises the Tjp1 inhibitor is implantable. As used herein, the term "patch" refers to a device or an implant that is contacted with the heart in order to provide a Tjp1 inhibitor as described herein to the heart. The patch can be prepared using any method known in the art.

As used in this application, the singular form "a," "an," and "the" include plural references unless the context clearly dictates otherwise. For example, the term "a Tjp1 inhibitor" includes a plurality of Tjp1 inhibitors, including mixtures and combinations thereof.

As used herein, the term "about" in the context of concentration of a substance, size of a substance, length of time, or other stated values means +/−5% of the stated value, or +/−4% of the stated value, or +/−3% of the stated value, or +/−2% of the stated value, or +/−1% of the stated value, or +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Tight junction protein 1 (Tjp1), also known as Zonula Occludens-1 (ZO-1), is an actin-binding scaffold protein that in CMs localizes to the intercalated disc. This plasma membrane subdomain contains N-cadherin-based adherens junctions, desmosomes and gap junctions and provides mechanical and electrical coupling between CMs. Tjp1 binds α-catenin, which associates with N-cadherin, as well as Cx-43. Tjp1 modulates self-renewal and differentiation of mouse ES cells and Tjp1-deficient mice show early embryonic lethality. Functional roles of Tjp1 in CMs are poorly understood. Tjp1 associates with Cx43 following gap junction internalization during MI-induced cardiac remodeling. Expression of a peptide that encodes the first two PDZ domains of Tjp1 leads to abnormal subcellular organization of adherens and gap junctions in rat ventricular CMs. Tjp1 levels studied with human HF showed lower Tjp1 levels in the failing heart, but upregulation in dilated and ischemic cardiomyopathy.

Here, it was shown that in contrast to stimulatory cues for CM proliferation provided by growth factors, the structural protein Tjp1 suppresses CM proliferation and regeneration following MI. Inducible inactivation of Tjp1 in adult CMs is sufficient to drive proliferation of heart cells, including abundant CMs, via activation of ErbB receptors and downstream Mek-Erk, Stat3, Akt, and Wnt signaling. Tjp1 directly binds ErbB4, thereby suppressing Nrg1-mediated signaling. After MI, enhanced CM proliferation in the infarct zone in the absence of Tjp1 limits pathological remodeling and prevents deterioration of cardiac function. Thus, silencing Tjp1 after MI may provide a novel therapeutic opportunity.

Material and Methods

Inducible Tjp1 Deletion in Mouse CMs

The generation of floxed Tjp1 (Tjp1$^{F/F}$) mice has been described. To specifically delete Tjp1 in CM, Tjp1$^{F/F}$ C57BL/6N mice were crossed to Myh6Cre$^{ERT2}$ (MerCreMer) C57BL/6 mice (kindly provided by Kristin B. Andersson (Institute for Experimental Medical Research, Oslo University Hospital, Norway with permission from Jeff Molkentin, Howard Hughes Medical Institute, Cincinnati Children's Hospital Medical Center), which express Cre in a tamoxifen inducible manner under the control of the CM specific α-myosin heavy chain (Myh6, MHC) promoter. Mice were back-crossed to the C57BL/6N background for more than 5 generations. Tamoxifen (Sigma) was dissolved in ethanol and diluted in autoclaved sunflower oil (Sigma). Six- to eight-week old mice were injected with 20 mg/ml Tamoxifen intraperitoneally for 5 days with a daily dose of 100 mg/kg body weight. Deletion of ZO-1 protein was verified by immunostaining and Western blot analysis. Control (Tjp1$^{+/+}$ Myh6-Cre$^{ERT2}$.) and Tjp1 cKO (Tjp1$^{F/F}$ Myh6-Cre$^{ERT2}$) mice induced with tamoxifen were used in the experiments. All animal experimentation protocols were approved by the relevant IACUC committee.

Genotyping

Genomic DNA was isolated from tail clippings and two primers were used in the PCR genotyping. Primer 1 (5'-CTT CTC TGA CCC TAC ACA GCT ACC-3'; SEQ ID NO: 5) and primer 2 (5'-ATC GTG TGG GAA AGA CAA GC-3'; SEQ ID NO: 6) amplified a fragment of 279 bp for the wild-type allele, and a fragment of 471 bp for the conditional mutant allele.

Histological Analysis

Freshly dissected hearts were fixed in 4% paraformaldehyde overnight, embedded in paraffin, sectioned to 5 µm in thickness and stained with hematoxylin and eosin. For detection of fibrosis, the heart sections were stained with a Masson's Trichrome Staining Kit (Polyscience).

Western Blot Analysis

Freshly dissected hearts were homogenized with a mortar and lysed for 15 min in lysis buffer (50 mM Tris-HCl, pH 7.5, 100 mM NaCl, 1 mM MgCl$_2$, and 0.5% Triton X-100) on ice. Lysates were sonicated and cleared by centrifugation (13,000×g for 15 min) at 4° C. The supernatant (equal amount of protein) was fractionated by SDS-polyacrylamide gel electrophoresis and subjected to Western blot analysis. Antibodies against ZO-1 (rabbit; Invitrogen Cat. #617300 or ThermoFisher Scientific Cat. #61-7300), Dab2 (mouse; BD Biosciences Cat. #610464), β-catenin (mouse; BD Biosciences, Cat. #610154), LEF1 (rabbit; Cell Signalling, Cat. #2230), Slug (rabbit; Cell Signalling, Cat. #9585), Snail (rabbit; Cell Signalling, cat. #3895), Sox2 (rabbit; Cell Signalling, Cat. #2748), Gsk3β (rabbit; Cell Signalling, Cat. #9315), pGsk3β (rabbit; Cell Signalling, Cat. #9323;), Erk1/2 (rabbit; Cell Signalling, Cat. #9102 or #4695), pErk1/2 (rabbit; Cell Signalling, Cat. #9101 or #4695), JNK (rabbit; Cell Signalling, Cat. #9258), pJnk (rabbit; Cell Signalling, Cat. #9255), p38 (rabbit 8690; Cell Signalling), phospho-p38 (rabbit; Cell Signalling, Cat. #4511), Akt (rabbit; Cell Signalling, Cat. #2920), pAkt (S473)(rabbit; Cell Signalling, Cat. #4060), Stat3 (rabbit; Cell Signalling, Cat. #4904), pStat3 (rabbit; Cell Signalling, Cat. #9145), cMyc (rabbit; Cell Signalling, Cat. #13987), pH3 (S10) (rabbit; Cell Signalling, Cat. #3377), cyclin D1 (rabbit; Cell Signalling, Cat. #2922), cyclin E (mouse; Cell Signalling, Cat. #4129), cyclin A2 (rabbit; Cell Signalling, Cat. #4656), Yap (rabbit; Cell Signalling, Cat. #8418), Runx1 (rabbit; Cell Signalling, Cat. #4336), MEF2c (rabbit; Cell Signalling, Cat. #5030), GP130 (rabbit; Santa Cruz, Cat. # SC-656), cyclin B1 (rabbit; Santa Cruz, Cat.# SC-752) GATA4 (rabbit; Santa Cruz, Cat.# SC-9053), Axin2 (rabbit; Abcam, Cat. # Ab332197), p21 (rabbit; Abcam, Cat. # Ab7960), SMA (rabbit; Abcam, Cat. # Ab5964), PCNA (mouse; Abnova, Cat. # H00005111), MF20 (mouse; The Developmental Studies Hybridoma Bank at the University of Iowa, Cat. # MF20-C), ErbB4 (rabbit; Cell Signalling Cat. #4795), pErbB4 (rabbit; Cell Signalling, Cat. #4757), EGFR (rabbit;

Cell Signalling, Cat. #4267), and pEGFR (rabbit; Cell Signalling, Cat. #3777) were used.

Immunostaining

Paraffin sections were dewaxed and the antigen was retrieved by steaming the slides for 20 min in a 2100 Retriever (Pick Cell Laboratories). Sections were incubated with primary antibodies against ZO-1 (rabbit; Invitorgen, Cat.#617300) and MF20 (mouse; The Developmental Studies Hybridoma Bank at the University of Iowa, Cat.# MF20-C) followed by suitably labelled secondary antibodies from Invitrogen, essentially as described previously. Nuclei were labelled with 4,6-diamidino-2-phenylindole (DAPI).

Apoptosis Assay

Paraffin sections were dewaxed and Terminal deoxynucleotidyltransferase-mediated dUTP-biotin nick end labelling (TUNEL) assays were carried out with the TMR Red In Situ Cell Death Detection kit (Roche Diagnostics) according to the manufacturer's protocol.

Proliferation Analysis

One hour before the mice were sacrificed, 50 μg of 5-ethynyl-2'deoxyuridine (Edu; Invitrogen) per gram of body weight were injected intraperitoneally into the mouse. Hearts were dissected out and processed as described above. The paraffin sections were dewaxed and stained with Click-iT™ EdU Imaging Kits (Invitrogen) according to the manufacturer's protocol.

In Vivo Treatment with Pharmacological Inhibitors

To block different signaling pathways, animals were administered either the Mek inhibitor PD0325901 (25 mg/kg mouse body weight; Sigma), the Stat3 inhibitor S31-201 (5 mg/kg mouse body weight; Santa Cruz Biotechnology), the Wnt inhibitor LGK974 (3 mg/kg mouse body weight; Biovision), or the EGFR/ErbB inhibitor Ast1306 (25 mg/kg mouse body weight; Selleckchem) via daily intraperitoneal injections for 5 days. The same route and schedule was used to administer Nrg1 (2.5 μg/mouse; dissolved in PBS, 0.1% BSA; ProsPec, Cat. # cyt-407c).

Surgical Procedures for MI and Cardiac Function Assessment

Myocardial infarction was induced in mice as previously described. Briefly, male mice (10-12 weeks old; 20-25 g) were anaesthetized with a mixture of 0.5 mg/kg Medetomidine (Pfizer Animal Health, Exton, Pa., USA), 5.0 mg/kg Dormicum (Sciencelab.com, Inc., Texas, USA) and 0.05 mg/kg Fentanyl (Pfizer Pharmaceuticals Group, New York, USA) and then subjected to permanent ligation of the left anterior descending artery. The mice were recovered by subcutaneous injection of 0.5 mg/kg Atipamezole (Pfizer Animal Health, Exton, Pa., USA) and 5 mg/kg Flumazenil (Sagent Pharmaceuticals, Illinois, USA) followed by 0.1 mg/kg Temgesic (Hospira Inc., Illinois, USA) for analgesia. After surgery, mice were injected via intraperitoneal route daily with 100 mg/kg tamoxifen for 5 days. Mouse genotypes were not known to the surgeon.

Cardiac function was assessed with a high frequency ultrasound system Vevo® 2100 (Visualsonics) and analyzed with Vevo® 2100 software, version 1.7.0, by a an experienced researcher who did not know the mouse genotpyes, as described. Briefly, B-Mode 3D datasets were acquired with the automated 3D-motor (Visualsonics) and using the integrated respiration and ECG gating to reduce artefacts. Echocardiography was performed on mice under general anaesthesia (1-1.5% isoflurane, Baxter, Singapore) at baseline, 1, 4, 8 and 12 weeks after MI. Body temperature was monitored with a rectal probe and maintained at 36-37° C.

Statistical Analysis

Comparisons between groups over time were performed using two-way ANOVA with Bonferroni post hoc analysis or GLM for repeated measurements. Values are reported as mean±SEM. P-value≤0.05 was considered statistically significant. Data were analyzed with SPSS (IBM® SPSS® Statistics version 22.0) and Prism (version 6, GraphPad Software) software.

cDNA and shRNA Plasmids

The untagged pcDNA3.1-ERBB4 was a gift from Yardena Samuels (Addgene plasmid #29527). In order to generate the ErbB4 mutant, the last three C-terminal amino acids of ErbB4 were mutated to alanine to abolish the PDZ binding motifs using Quik change site directed mutagenesis kit according to manufacturer's instructions (Agilent Technologies). PDZ 1-3 domains of human ZO-1 were cloned into pGEX 4T-1 vector using standard cloning protocols. ZO1 or TJP1 and control shRNA plasmids were obtained from Mission shRNA (Sigma).

GST Pull Down Assays

ErbB4 and mutant was transfected into HEK293 cells using JetPrimePolyPlus transfection kit (PolyPlus Transfections) according to manufacturer's instructions. Cell lysates were prepared in lysis buffer (20 mM Tris-HCl, pH7.4, 150 mM NaCl, 1 mM EDTA, 0.25% deoxycholate, 1% NP-40 and protease inhibitors). GST and GST ZO-1PDZ1-3 domain fusion proteins were were generated, purified, and bound to Glutathione Sepharose-4B (GE Healthcare Life Sciences) using standard protocols. Bound proteins were quantified by SDS-PAGE by using known amounts of BSA as standards. 18 μl of GST beads were incubated with 1 μg of GST fusion proteins. Unbound proteins were removed by washing with ice cold PBS. 300 μg of the transfected cells were then added and incubated at 4° C. for 2 hr followed by washing 4 times with ice cold lysis buffer. The bound fractions were eluted with 4×SDS-PAGE sample buffer, separated by SDS PAGE, immunoblotted onto PVDF membranes and probed with Rabbit anti-ErbB4 antibodies.

ZO-1 shRNA Knockdown in MCF7 Cells and NRG-1 Stimulation

Lentiviral particles were generated using 293FT cells and Virapower Lentiviral packaging mix and Lipofectamine 2000 reagents according to manufacturer's protocols (Life Technologies). The lentiviral particles were then added to MCF7 cells and stable selection was carried out using puromycin. Cells then were plated on 60 mm dishes and the following day washed with OPTI-MEM media with overnight incubation. The next day, serum starved cells were stimulated with human NRG-1 (Cell Signalling Technology, Cat. #5218) at different time points. Cells were lysed in RIPA buffer (20 mM Tris-HCl, pH7.4, 150 mM NaCl, 1 mM EDTA, 0.25% deoxycholate, 1% TritonX-100, 0.1% SDS and protease inhibitors), quantitated and analysed on SDS-PAGE and Western blot. For dose-response experiments, cells were plates on 60 mm dishes and serum starved overnight as indicated above. The following day, cells were stimulated with varying concentrations of NRG-1 for 15 mins subsequently washed in ice-cold PBS, lysed with RIPA buffer and processed for SDS-PAGE and Western blot.

Experimental Result

Inactivation of Tjp1 in CMs Leads to Cell Proliferation in Adult Mouse Heart

After Cre-mediated inactivation of Tjp1 in CMs, Tjp1 protein level in the heart (FIG. 1A) was reduced and the protein undetectable in most CMs (FIG. 1B). This correlated with widespread LacZ staining, indicative of Cre-recombinase expression, in a majority of CMs in the Tjp1$^{F/F}$ Myh6-CreERT2/Rosa26-LacZ reporter mouse line following tamoxifen induction (FIG. 1C). The LacZ staining pattern remained similar up to one year after tamoxifen induction (data not shown), indicating that wildtype cells did not replace Tjp1-null CMs. Histological analysis of the Tjp1 cKO heart at one or seven days after the last tamoxifen injection did not show gross abnormalities (FIG. 1D) or apoptosis (FIG. E).

Figure 2:
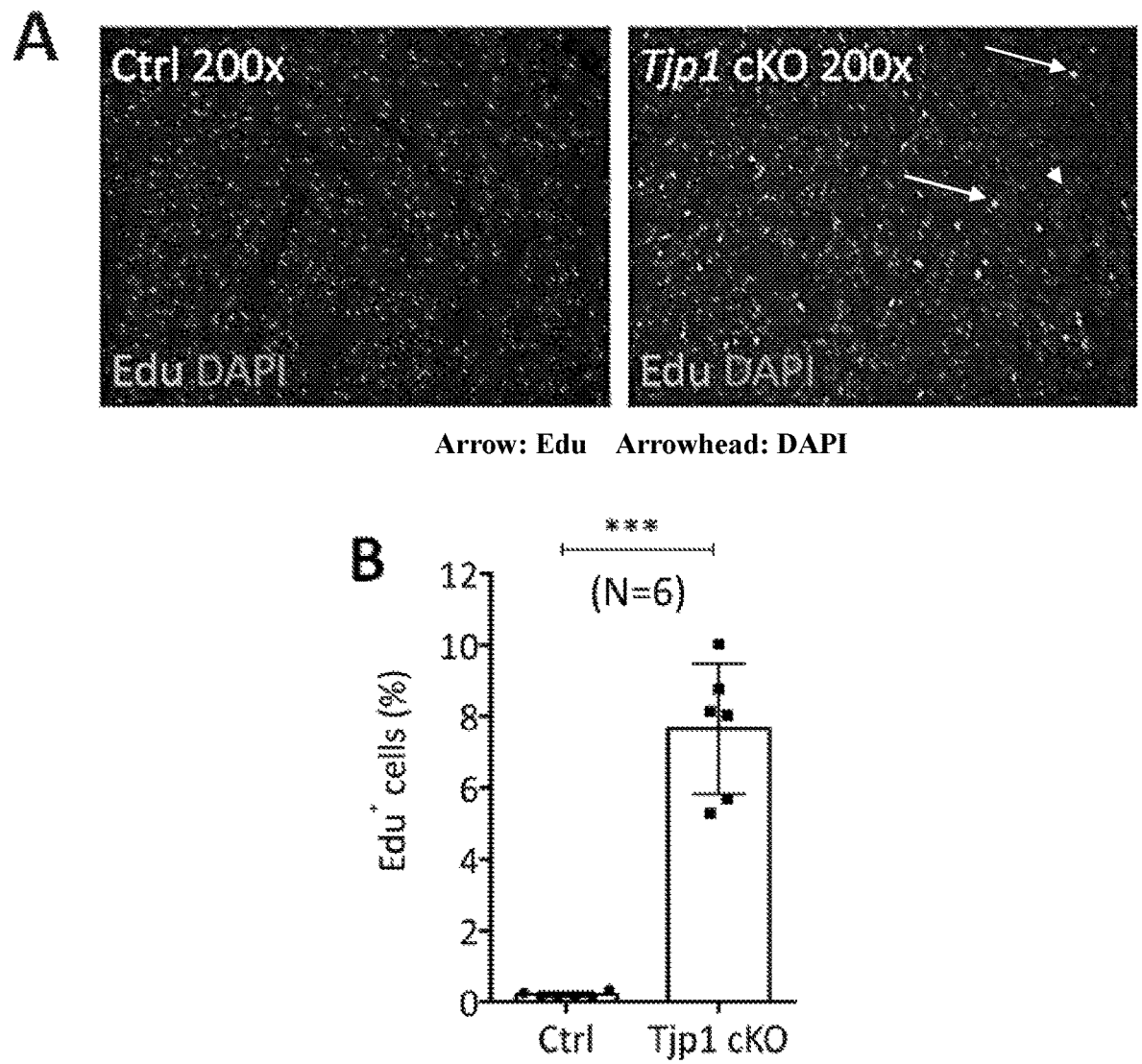
FIG. 2 shows a set of experimental results that illustrate that the deletion of Tjp1 induces cell proliferation in the adult heart.
Figure 2:
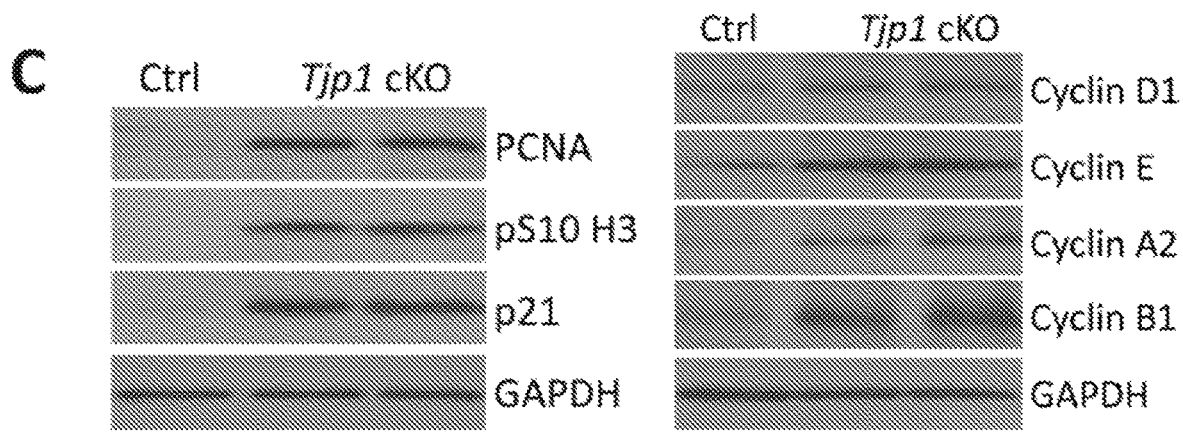
Figure 2:
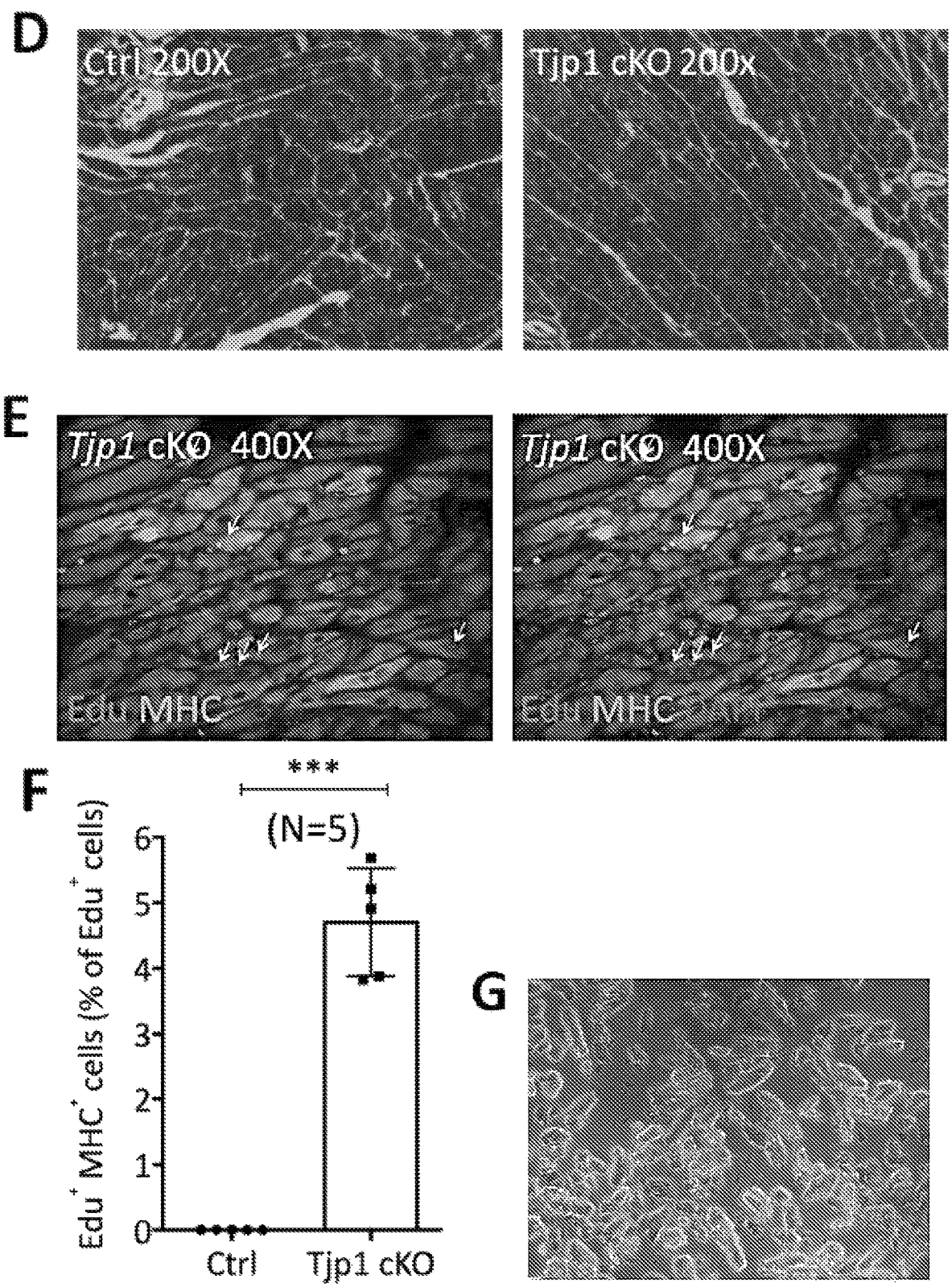
Figure 2:
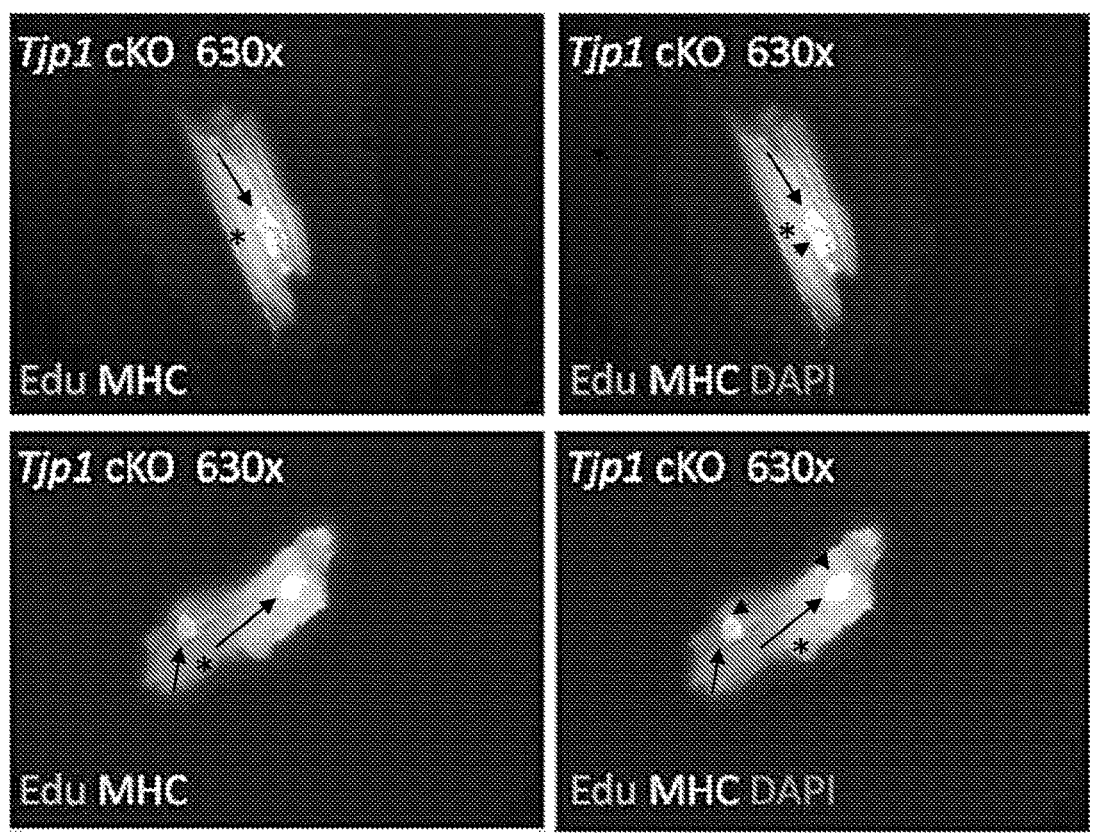
Figure 2:
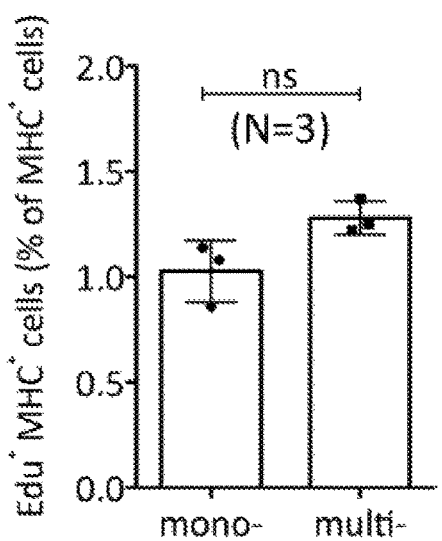
Figure 2:
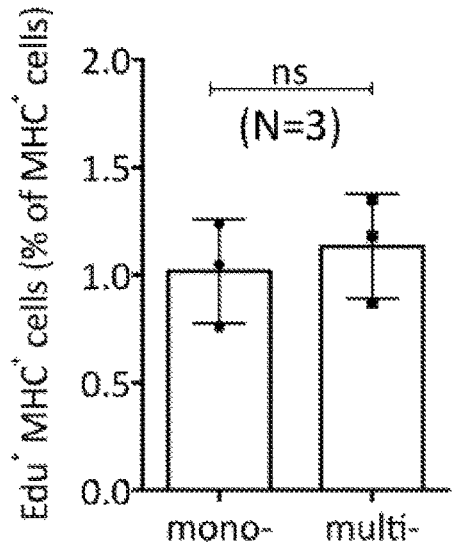
Figure 2:
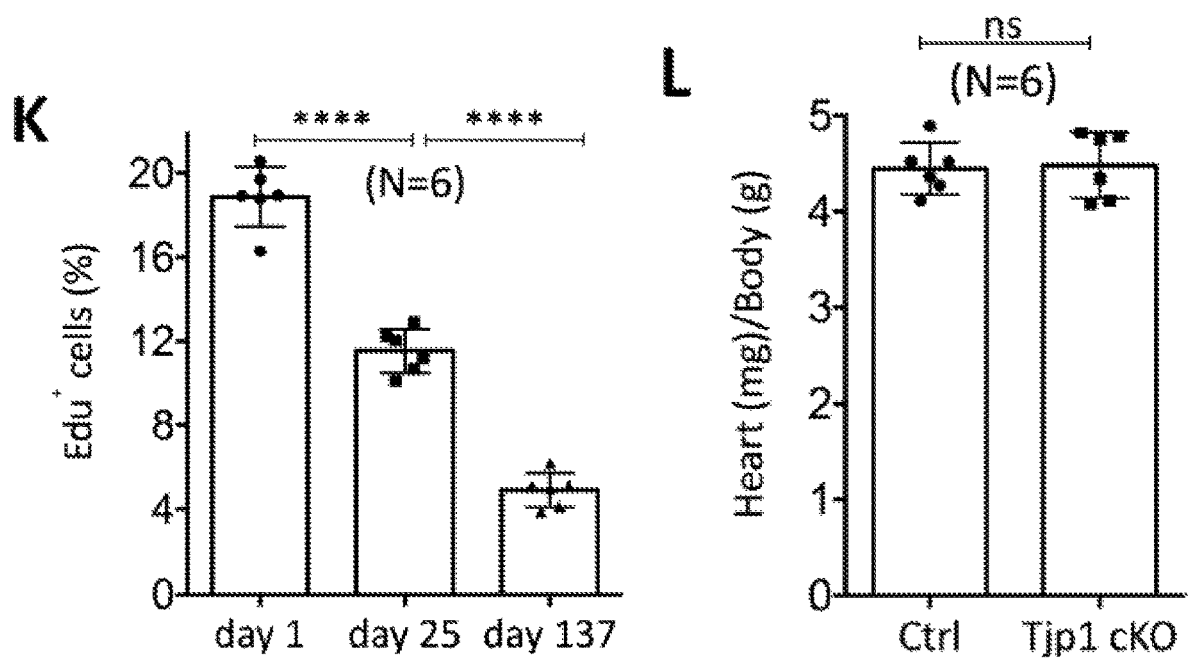

Despite normal histology, heart size (FIG. 1F) and heart to body weight ratio (FIG. 1G) of Tjp1 cKO mice were slightly higher compared to controls. To analyze if the larger Tjp1 cKO heart size reflected cell proliferation, Edu was injected one day after the last tamoxifen administration. Edu-positive nuclei, rarely found in control sections, were abundant in the Tjp1 cKO heart (FIGS. 2A, B). Consistent with mitosis and enhanced cell proliferation, higher PCNA, pS10-H3, Cyclin D1, Cyclin E, Cyclin A2 and Cyclin B1 protein levels were detected in adult Tjp1 cKO heart (FIG. 2C). Masson's Trichrome staining did not show fibrosis in Tjp1 cKO heart (FIG. 2D).

Co-labeling for the CM maker cardiac a-myosin heavy chain (MHC; Myh6) showed that at least 5% of Edu-positive cells were MHC-positive CMs (FIGS. 2E, F). In dissociated CMs (FIG. 2G), approximately 50% of the Edu- and MHC-positive cells contained a single nucleus 3 days after the last tamoxifen injection (FIG. 2I) and this fraction did not change one month later (FIG. 2J). In contrast, the fraction of total Edu-positive cells declined with time (FIG. 2K), likely explaining the normalization of the heart to body weight ratio after 137 days (FIG. 2L).

CMs Undergo Partial Dedifferentiation after Tjp1 Deletion

Dedifferentiation of pre-existing CMs followed by proliferation and re-differentiation is one mechanism by which new CMs can be generated. Indicative of dedifferentiation, high magnification visualization of MHC stained heart sections prepared one day after the last tamoxifen injection revealed changes in sarcomere organization in Tjp1 cKO heart (FIG. 3A). One week later, the sarcomere structure recovered. More than 2% of the Edu-positive cells labeled with either GATA4 (FIGS. 3B, C) or Nkx2.5 (FIGS. 3D, E), two early markers of CM differentiation. Dab2, highly expressed in embryonic heart and repressed after birth and considered a marker for CM dedifferentiation, was upregulated in the Tjp1 deficient heart (FIG. 3F). Changes in protein levels of Runx1, MHC, α-SMA or Nkx2.5, which have also been linked to heart development, were less pronounced.

Tjp1 Deletion Activates Signaling Pathways that Drive CM Proliferation

Next, signaling pathways activated in the Tjp1 cKO heart, focusing on pathways that linked to CM proliferation, was assessed. The mitogen-activated protein kinase (MAPK) pathway is activated by receptors implicated in CM proliferation, including ErbB2 and ErbB4. Inhibition of Stat3 in the zebrafish, while not affecting growth-related CM proliferation, restricts injury-induced heart regeneration. Activation of Akt through PI3K stimulates CM proliferation, as does Wnt signaling.

Consistent with increased cell proliferation, MAPK signaling was activated in response to deletion of Tjp1 (e.g. higher pThr202/Tyr204-Erk levels) (FIG. 4A). Conversely, p38 and JNK, which when inhibited promote cell-cycle re-entry and cytokinesis of CMs, were suppressed in Tjp1 cKO heart (e.g. lower pThr180/Tyr182-p38 and pThr183/Tyr185-JNK levels). Total Stat3 as well as pY705-Stat3 protein levels were elevated in hearts lacking Tjp1 (FIG. 4A). Consistent with Stat3 activation, the downstream target gene c-Myc was up-regulated. Gp130, which is upstream of Stat3, was unchanged. Akt1 and in particular pS473-Akt protein levels were increased in the Tjp1 cKO heart. Despite slightly reduced total β-catenin levels after tamoxifen induction, the expression of its coactivator LEF1 and several downstream target genes, including Axin2, Slug, Snail, and Sox2, were highly elevated (FIG. 4A), indicating activation of Wnt signaling.

Figure 7:
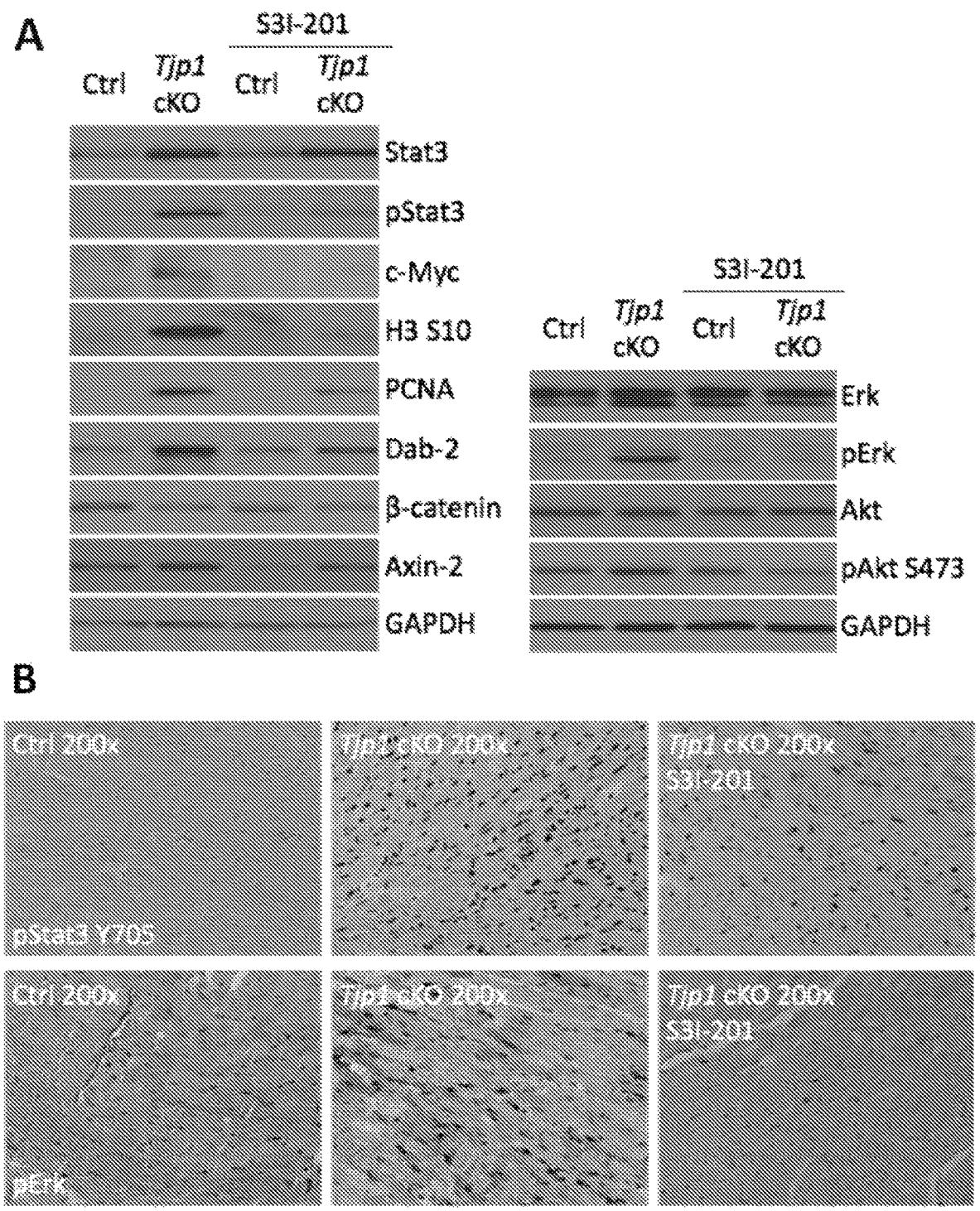
FIG. 7 shows a set of experimental results that illustrate that inhibitors of Stat3, Akt and Wnt suppress signaling and proliferation induced by Tjp1 deletion in the adult heart to different extents.
Figure 7:
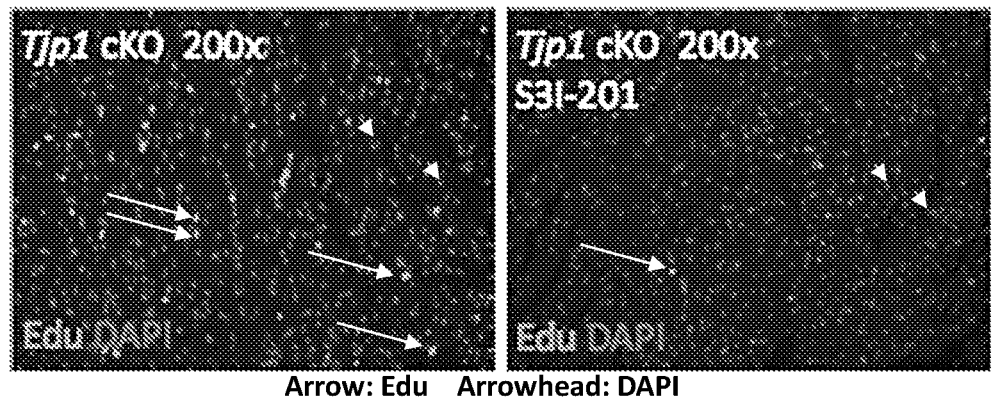
Figure 7:
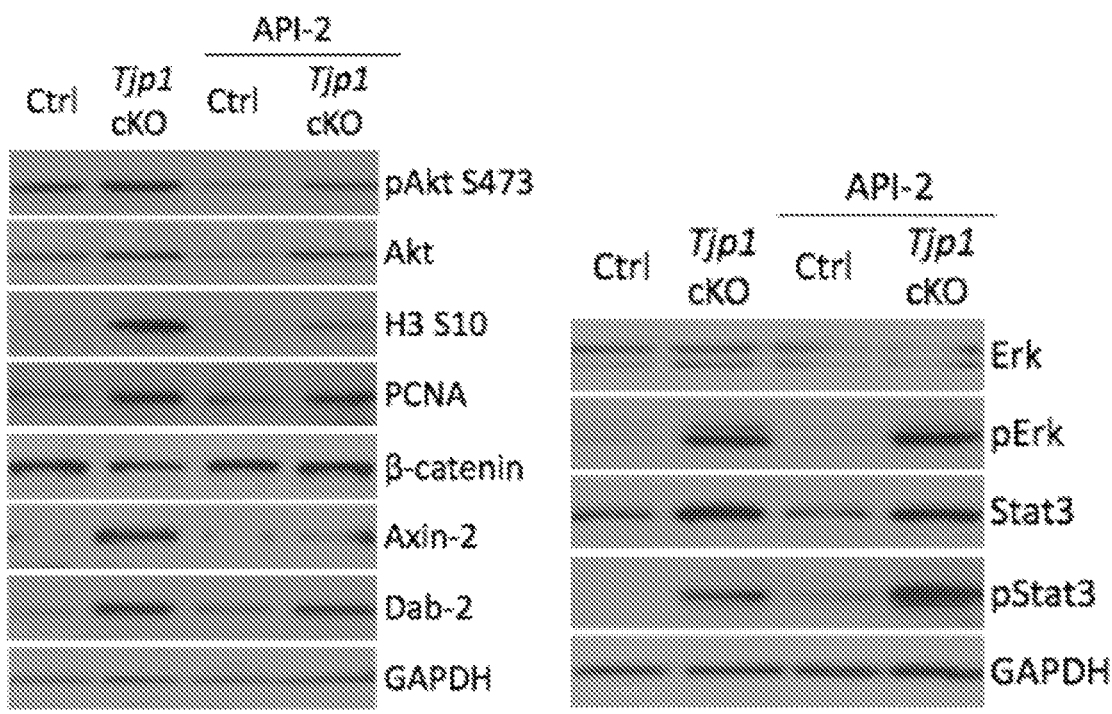
Figure 7:
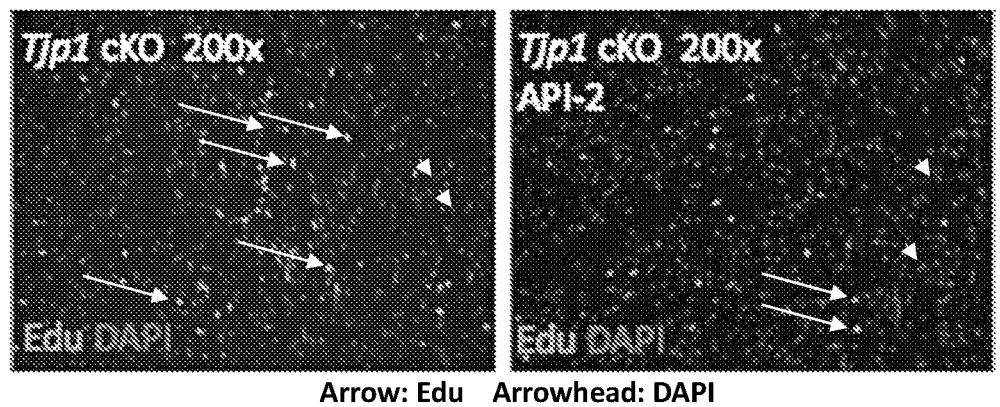
Figure 7:
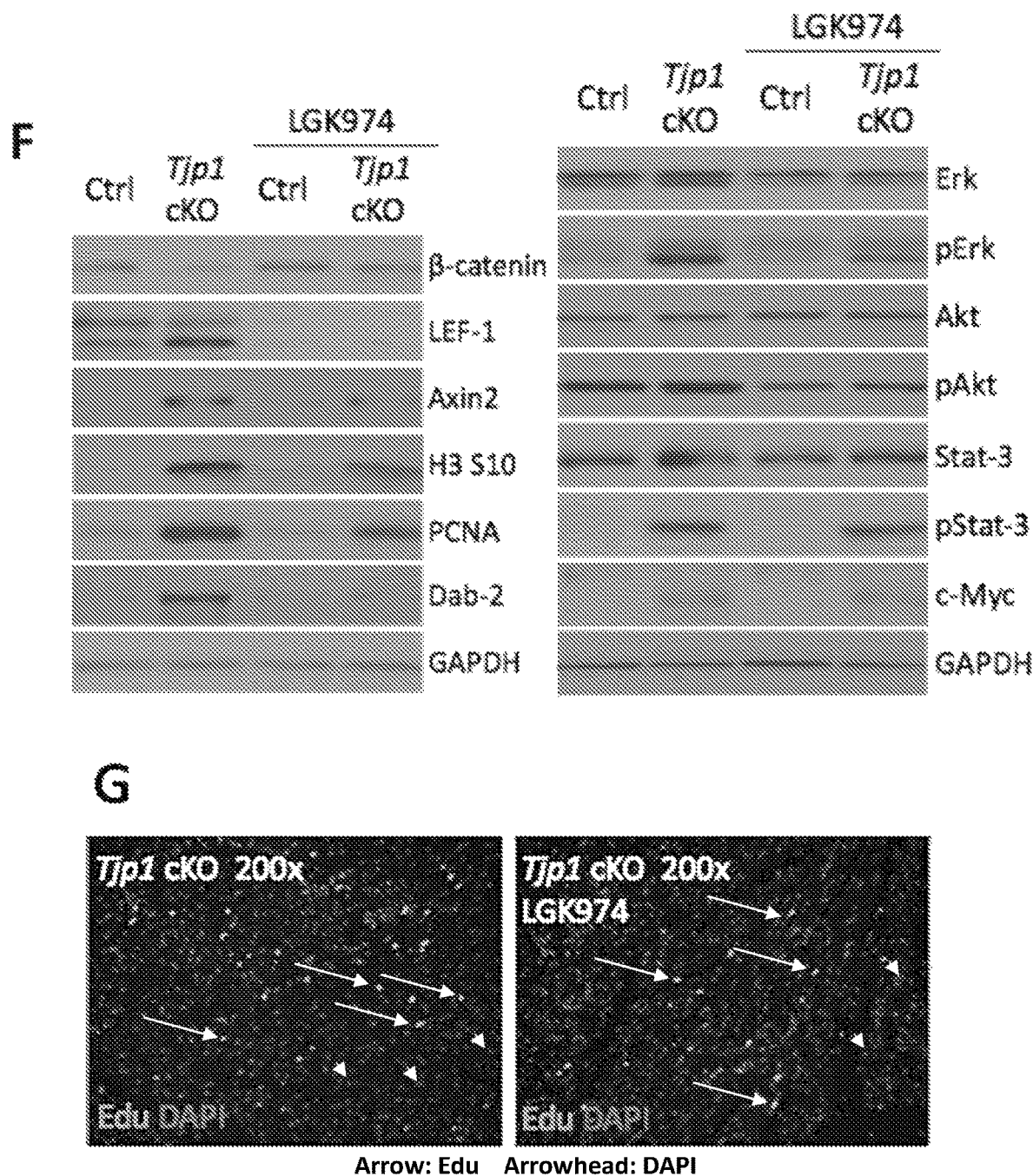
Figure 8:
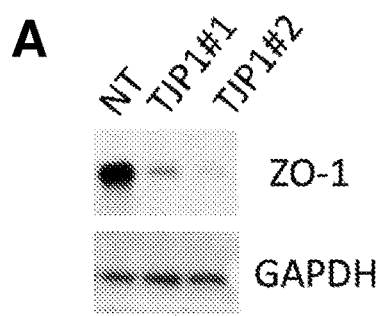
FIG. 8 shows a set of experimental results that illustrate the silencing of mouse Tjp1 and Tjp2 with shRNAs.

To explore the contribution of the different signaling pathways and to confirm that their activation drives cell proliferation upon Tjp1 deletion, chemical inhibitors that are well tolerated by mice during short-term systemic exposure were used. The inhibitors were administered simultaneously with the daily tamoxifen injection over 5 days to induce deletion of Tjp1. After the last injection, hearts were collected and analyzed. Mek phosphorylates and activates Erk, its immediate downstream target. PD0325901, a specific Mek inhibitor, suppressed activation of the different effectors (FIGS. 4B, C) and consequently cell proliferation activated by Tjp1 deletion (FIG. 4D, E). The Stat3 inhibitor S31-201 prevented Stat3 and Erk activation, moderately inhibited Akt and Wnt signaling and suppressed cell proliferation in the Tjp1 cKO heart (FIG. 4F, FIG. 7). The Akt inhibitor API-2 significantly suppressed Akt phosphorylation, partially reduced Wnt signaling, but did not affect pErk or pStat3 levels. LGK974, a small molecule inhibitor of Porcupine, the activity of which is required for Wnt secretion, suppressed Wnt signaling, moderately reduced Erk and Akt but not Stat3 phosphorylation. Consistent with their partial effects, API-2 and LGK974 reduced Tjp1 deletion-induced cell proliferation to a more moderate extent (~50%; FIGS. 4G, H).

CM Proliferation after Tjp1 Deletion Requires ErbB Receptor Activation and is Enhanced by Nrg1

Erk, Stat3 and Akt are common downstream effectors of the ErbB family of growth factor receptors, suggesting that these receptors may be activated upon deletion of Tjp1. It was therefore determined if AST1306, an irreversible inhibitor of the kinase activity of ErbB receptors that blocks ligand induced autophosphorylation and activation, suppresses the activation of the downstream effectors. Increase in phosphorylated Erk, Stat3 and Akt in Tjp1 cKO hearts was strongly abrogated by AST1306, as was c-Myc level (FIG. 5A). Lower Axin-2 protein level also indicated inhibition of Wnt signaling. pS10-H3 and PCNA expression in Tjp1 cKO hearts was strongly reduced by the compound (FIG. 5A). Less than 1% of Edu-positive cells were present in the treated as compared to 7% in the non-treated Tjp1 cKO heart (FIGS. 5B, C).

Interestingly, EGFR protein levels and phosphorylation were elevated upon Tjp1 deletion and this was abrogated by AST1306 (FIG. 5A). Since the Nrg1/ErbB4 axis has been implicated in CM proliferation and AST1306 is a pan-ErbB inhibitor, ErbB4 activation in Tjp1 cKO hearts was analyzed. Similar to EGFR, ErbB4 protein and phosphorylation levels were increased in the Tjp1 cKO heart (FIG. 5D). To assess a possible role of Nrg1 on cell proliferation, 5 daily injections of Nrg1 and Edu were carried out 3 weeks after Tjp1 deletion, when the number of Edu-positive cells had declined (FIGS. 2K; 5E, F). Nrg1 significantly increased cell proliferation in Tjp1 cKO hearts as compared to non-treated or treated control hearts (FIGS. 5E, F). Nrg1 application generated abundant Edu- and MHC-positive cells (10 out of 576) in the Tjp1 cKO heart as opposed to mostly MHC-negative proliferating cells in control heart.

Tjp1 Associates with ErbB4 to Suppress Nrg1 Mediated Signaling

The above data indicates an inhibitory role of Tjp1 on Nrg1-mediated ErbB4 signaling in the heart. To confirm this and further analyze the mechanism, MCF7 cells, which are easier to culture and analyze than adult CMs, were used. shRNA-mediated silencing of Tjp1 sustained Nrg1-induced ErbB4 signaling (FIG. 5G). In control cells, Erk phosphorylation peaked ~15 min after ligand addition and subsequently declined to basal levels between 60 and 120 min. In contrast, Erk remained phosphorylated after 240 min in cells where Tjp1 had been silenced. Concomitant with enhanced Nrg1-induced signaling and as observed in heart, ErbB4 protein levels increased when Tjp1 was silenced, suggesting effects on receptor trafficking and/or processing. Dose-response experiments showed that silencing of Tjp1 highly sensitized cells to Nrg1 (FIG. 5H). While maximal Erk activation required 50-100 ng/ml Nrg1 in control cells, this was achieved with as little as 2.5 ng/ml after depletion of Tjp1.

ErbB4 contains a C-terminal PDZ-binding motif (PBM) (FIG. 5I). To test if this PBM can interact with PDZ domains of Tjp1, pull-down assays using a GST-fusion protein carrying the three PDZ domains of Tjp1 (Tjp1 PDZ1-3) and lysates from cells expressing wild-type ErbB4 or a mutant with a disrupted PBM (ErbB4 ΔPBM) were performed. The Tjp1 PDZ domains were able to pull down ErbB4 and this association required an intact PBM (FIG. 5J). The ErbB4 co-receptor ErbB2 also contains a putative PBM and likewise interacted with the Tjp1 PDZ domains (FIGS. 5I and K).

Inactivation of Tjp1 after MI Promotes CM Proliferation and Preserves Cardiac Function.

Figure 6:
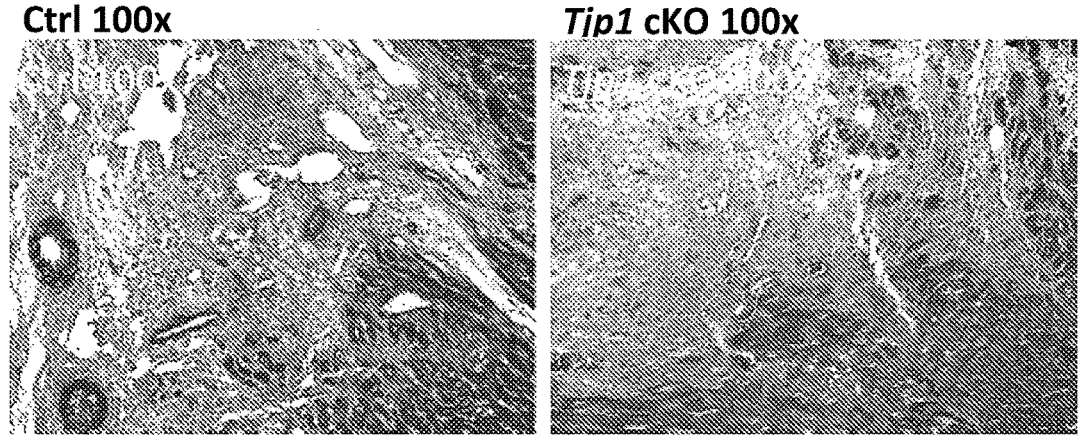
FIG. 6 shows a set of experimental results that illustrate that enhanced cardiomyocyte (CM) proliferation and sustained heart function were observed following experimental myocardial infarct (MI) and Tjp1 deletion.
Figure 6:
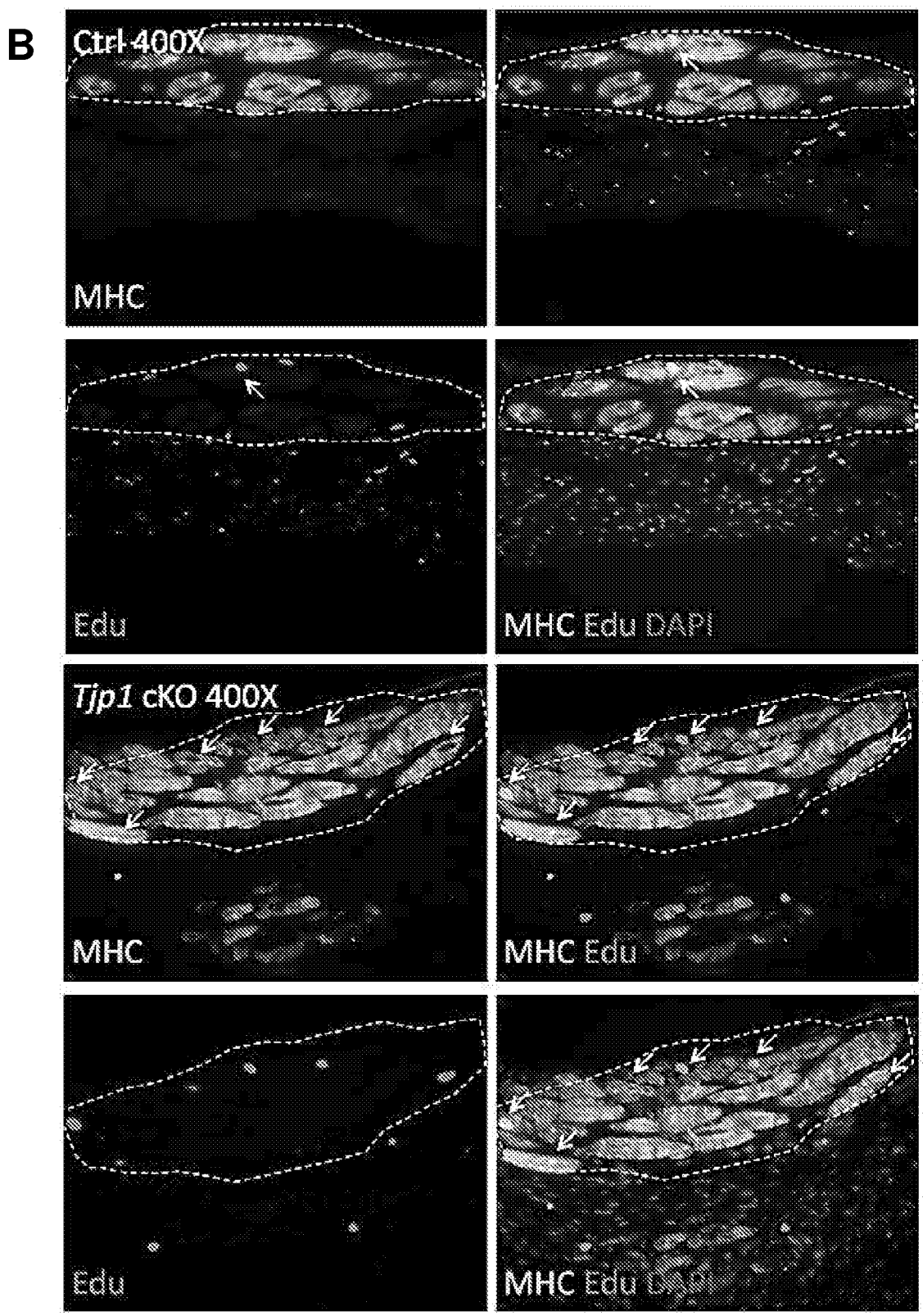
Figure 6:
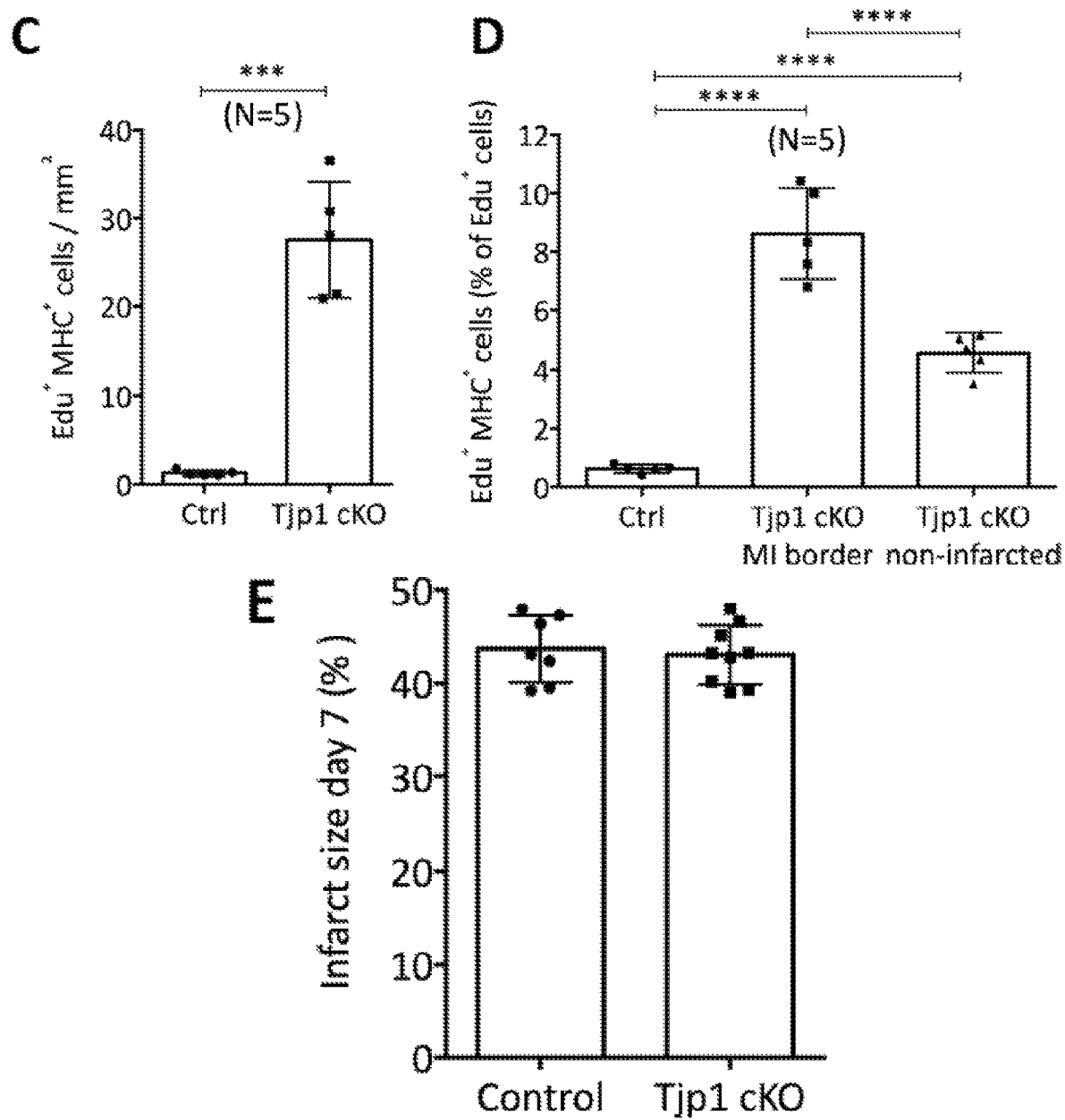
Figure 6:
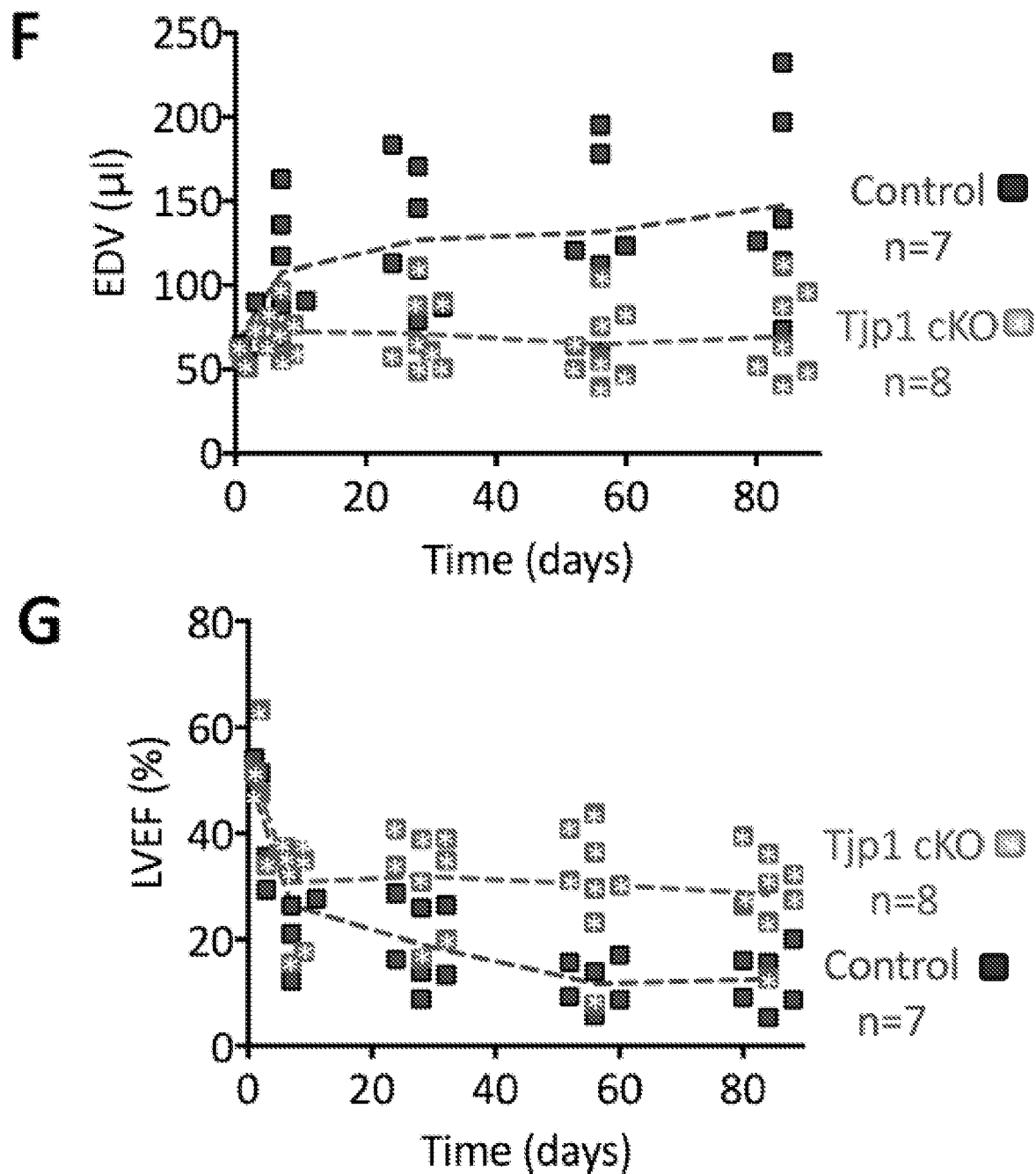
Figure 6:
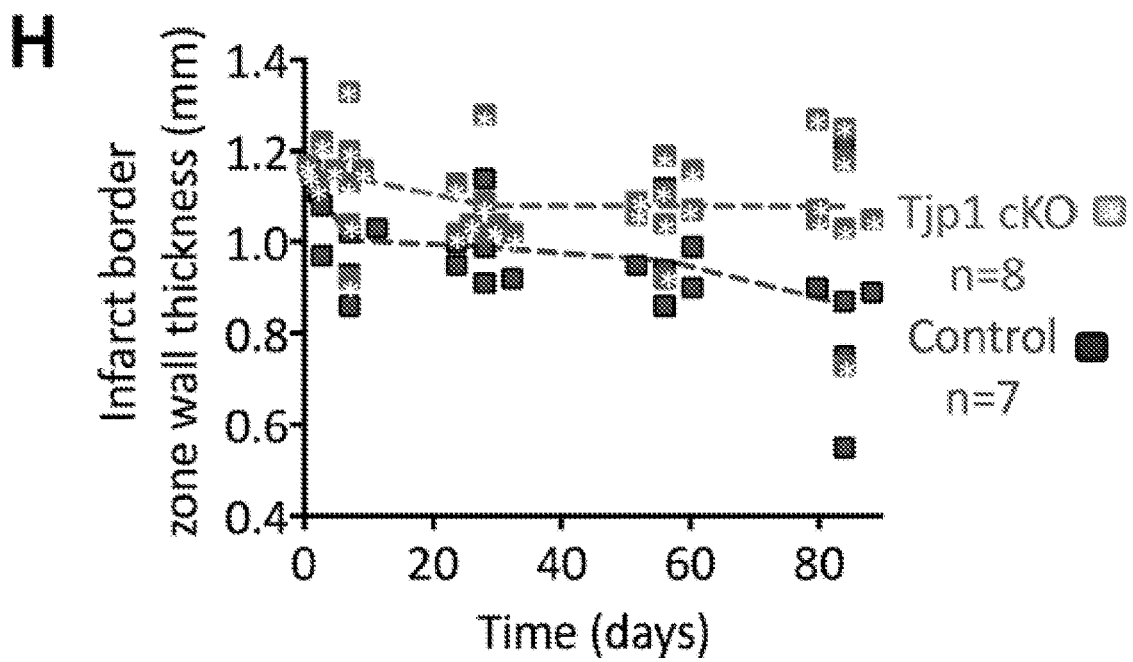
Figure 6:
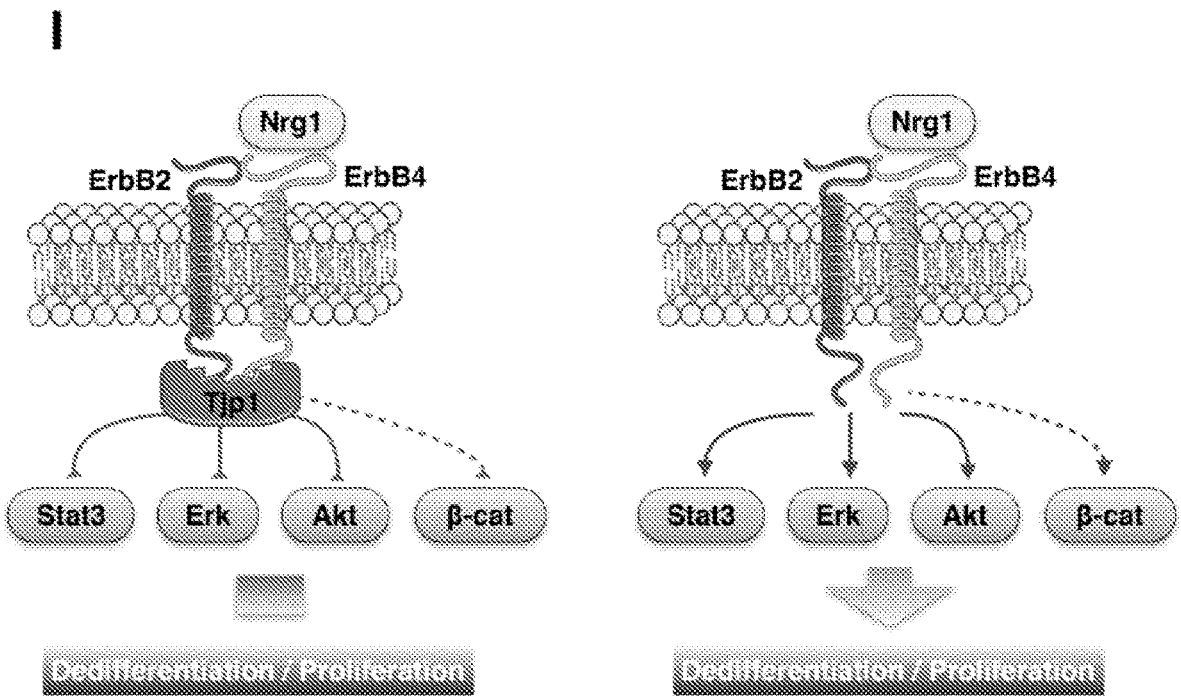

The effect of Tjp1 deletion on heart regeneration and function after MI was investigated next. One day after surgery for permanent ligation of the left anterior descending artery, mice were injected with tamoxifen for 5 days to delete Tjp1. After injection with Edu for 3 days, mice were sacrificed 1 week or 1 month later. Masson's Trichrome staining indicated scar formation in the infarct area of the left ventricle (LV) of both the control and Tjp1 cKO heart (FIG. 6A). Significantly more Edu- and MHC-positive CMs were found in the infarct border area in the Tjp1 cKO heart (FIGS. 6B and C). Interestingly, twice as many proliferating cells were MHC-positive CMs in the infarct border region as compared to non-injured heart tissue (FIG. 6D), suggesting a synergistic effect of the infarct niche and the absence of Tjp1 on CM proliferation.

Echocardiography was used to assess heart function. Initial infarct size was similar in control and Tjp1 cKO mice 7 days post-MI (43.7% versus 43.1%; p=0.0573; FIG. 6E). After MI, left ventricular end diastolic volume (EDV) increased initially for both the control and Tjp1 cKO LVs (FIG. 6F), as expected for similar infarct size. With time, however, EDV continued to increase to a significantly larger extent in controls compared to Tjp1 cKO hearts, consistent with less adverse remodeling in the latter. LV ejection fraction (EF) declined in both the control and Tjp1 cKO heart to ~30%, consistent with a comparable initial infarct size. However, while LVEF continued to decline in controls, it was preserved in the absence of Tjp1 (p=0.033 at week 8 and p=0.006 at week 12; GLM for repeated measurements, p=0.024 between genotypes; FIG. 6G), showing that heart dysfunction post-MI was attenuated by Tjp1 deficiency. The infarct border zone wall, estimated by echocardiography, was significantly thicker at week 1 in the Tjp1 cKO heart (1.00±0.04 mm for control versus 1.15±0.04 mm for Tjp1 cKO; p=0.029; FIG. 6H), likely reflecting the proliferation of both CMs and non-CMs. This difference became less at week 12 post-MI (0.86±0.09 mm for WT versus 1.08±0.06 mm for KO; p=0.081), possibly due to the loss of non-CMs and less adverse LV remodeling, as shown by the reduced LV dilation indicated by EDV. Taken together, deletion of Tjp1 after MI leads to enhanced CM proliferation, in particular in the scar border region, limiting adverse remodeling and preserving heart function for at least 12 weeks.

Discussion

Overcoming the lack of regenerative capacity in terminally differentiated adult mammalian CMs has been of great interest for decades. The limited ability of adult CMs to dedifferentiate and proliferate hampers recovery of function following acute cardiac injury and cell loss, leading to HF. To date, drug therapies for HF, while effective, still leave patients with dismal prognoses. Identifying the cellular mechanisms underlying adult cardiac regeneration offers the potential to target key pathways for optimization of cardiac adaptive response to injury, thus preventing or reversing HF. The Nrg1/ErbB4 axis has emerged as a promising therapeutic target, with Nrg1 based therapies in human clinical trials. The first evidence that the structural protein Tjp1 acts as a suppressor of Nrg1/ErbB4 signaling and CM proliferation in the adult mouse heart was provided. After experimental MI, depleting Tjp1 enhances CM regeneration particularly in the infarct border zone, preserving cardiac function.

New CMs can be generated from either cardiac precursors or preexisting CMs following dedifferentiation. The immediate response to the loss of Tjp1 from the N-cadherin complex of the intercalated disc may be a partial and transient uncoupling and dedifferentiation of CMs, as shown by changes in sarcomere structure and expression of early cardiac lineage markers (e.g. Nkx2.5, Gata4, Dab-2). Pharmacological inhibitors that suppressed cell proliferation also reduced Dab-2 protein levels, suggesting that dedifferentiation and proliferation are interlinked. CM dedifferentiation and proliferation were also observed after expression of a constitutively active ErbB2. Since most murine CMs are bi- or multinucleated, the presence of similar numbers of mono- and bi-nucleated Edu-positive CMs in the Tjp1 cKO heart further supports their origin from preexisting CMs. Newly generated CMs persisted in the heart, but Edu-positive non-CM cells declined over time (from ~20% to 5% within 5 months). While it is not clear how excess fibroblasts are removed, it likely explains the moderate and transient increase in heart size, and the absence of fibrosis. Nevertheless, cells in the Tjp1 cKO heart remain receptive to proliferative stimuli, such as Nrg1 administration.

Tjp1 was recently shown to bind and suppress the activity of EGFR, another member of the ErbB receptor family. Depletion of Tjp1 in CMs and MCF-7 cells results in ErbB4 receptor activation, possibly by sensitizing to lower ligand concentrations and/or sustaining activation state. The latter could include effects of Tjp1 on ErbB4 receptor trafficking or processing, given that EGFR and ErbB4 protein levels in the heart and MCF-7 cells were increased after Tjp1 depletion. Nrg1/ErbB4 and ErbB2, which also binds Tjp1, stimulate adult cardiomyocyte proliferation via activation of Erk, Stat3, Akt and Wnt signaling. These effectors and pathways are also activated in the Tjp1 cKO heart and, as shown using specific pharmacological inhibitors, required for cell proliferation. Intriguingly, deletion of Tjp1 in CMs not only stimulated proliferation of CMs, but also other cells in the heart. Paracrine/autocrine mechanisms, whereby growth factors secreted by Tjp1 deficient CMs stimulate proliferation of the non-CM cells, were hypothesized. These, or additional factors secreted by activated non-CMs, could further act in an autocrine or paracrine fashion, respectively, on CMs. Endothelial cells, for example, secrete a variety of cardio-active factors, including Nrg1.

In a mouse model of acute MI, removing Tjp1 after infarction improved the overall outcome, as assessed by clinically relevant parameters. Tjp1 deletion resulted in a dramatic increase of proliferating CMs in the scar border region. Twice as many proliferating CMs were detected in the infarct border as compared to non-injured Tjp1 cKO heart tissue. Following MI infarct, growth factors and cytokines are released by the injured heart and infiltrating immune cells, which may stimulate proliferation of CMs lacking Tjp1. Presumably enhanced CM proliferation in the infarct border area limits adverse remodeling, resulting in the observed preservation of heart function from 8 weeks onwards, as measured by EDV and LVEF. This shows that proliferation of CMs via deletion of Tjp1 partly restores the loss of CMs after injury, thereby protecting the mouse heart against adverse LV remodeling and loss of cardiac function.

In summary, Tjp1 suppresses ErbB4 signaling and its removal sensitizes ErbB4 to its ligand Nrg1 and sustains receptor activation. This triggers the downstream effectors Mek-Erk, Stat3, Akt and Wnt signaling to induce CM proliferation. Deletion of Tjp1 post-MI preserves cardiac function, thus providing a novel target to control adverse remodeling and subsequent HF through regeneration of CMs. CM-specific silencing of Tjp1 could circumvent possible oncogenic risks associated with systemic and prolonged administration of Nrg1. Alternatively, cardiac-specific inactivation of Tjp1 could be considered to enhance the efficacy of Nrg1, or in combination with other ErbB receptor ligands.

REFERENCES

Arslan, F., D. P. de Kleijn, and G. Pasterkamp, *Innate immune signaling in cardiac ischemia* Nat Rev Cardiol, 2011. 8(5): p. 292-300.

Arslan, F., et al., *Treatment with OPN-305, a humanized anti-Toll-Like receptor-2 antibody, reduces myocardial ischemia/reperfusion injury in pigs*. Circ Cardiovasc Interv, 2012. 5(2): p. 279-87.

Barker, R. J., Price, R. L., and Gourdie, R. G. (2002). Increased association of ZO-1 with connexin43 during remodeling of cardiac gap junctions. Circ Res 90, 317-324.

Barrott, J. J., Cash, G. M., Smith, A. P., Barrow, J. R., and Murtaugh, L. C. (2011). Deletion of mouse Porcn blocks Wnt ligand secretion and reveals an ectodermal etiology of human focal dermal hypoplasia/Goltz syndrome. Proc Natl Acad Sci USA 108, 12752-12757.

Bersell, K., et al., *Neuregulin1/ErbB4 signaling induces cardiomyocyte proliferation and repair of heart injury*. Cell, 2009. 138(2): p. 257-70.

Bisping, E., Ikeda, S., Kong, S. W., Tarnayski, O., Bodyak, N., McMullen, J. R., Rajagopal, S., Son, J. K., Ma, Q., Springer, Z., et al. (2006). Gata4 is required for maintenance of postnatal cardiac function and protection from pressure overload-induced heart failure. Proceedings of the National Academy of Sciences 103, 14471-14476.

Bruce, A. F., Rothery, S., Dupont, E., and Severs, N. J. (2008). Gap junction remodelling in human heart failure is associated with increased interaction of connexin43 with ZO-1. Cardiovasc Res 77, 757-765.

Cheng, R. K., Asai, T., Tang, H., Dashoush, N. H., Kara, R. J., Costa, K. D., Naka, Y., Wu, E. X., Wolgemuth, D. J., and Chaudhry, H. W. (2007). Cyclin A2 Induces Cardiac Regeneration After Myocardial Infarction and Prevents Heart Failure. Circulation Research 100, 1741-1748.

D'Uva, G., Aharonov, A., Lauriola, M., Kain, D., Yahalom-Ronen, Y., Carvalho, S., Weisinger, K., Bassat, E., Rajchman, D., Yifa, O., et al. (2015). ERBB2 triggers mammalian heart regeneration by promoting cardiomyocyte dedifferentiation and proliferation. Nat Cell Biol 17, 627-638.

D'Uva, G., Aharonov, A., Lauriola, M., Kain, D., Yahalom-Ronen, Y., Carvalho, S., Weisinger, K., Bassat, E., Rajchman, D., Yifa, O., et al. (2015). ERBB2 triggers mammalian heart regeneration by promoting cardiomyocyte dedifferentiation and proliferation. Nature Cell Biology 17, 627-638.

DeBosch, B. (2006). Akt1 Is Required for Physiological Cardiac Growth. Circulation 113, 2097-2104.

Eulalio, A., Mano, M., Ferro, M. D., Zentilin, L., Sinagra, G., Zacchigna, S., and Giacca, M. (2012). Functional screening identifies miRNAs inducing cardiac regeneration. Nature 492, 376-381.

Fang, Y., Gupta, V., Karra, R., Holdway, J. E., Kikuchi, K., and Poss, K. D. (2013). Translational profiling of cardiomyocytes identifies an early Jak1/Stat3 injury response required for zebrafish heart regeneration. Proceedings of the National Academy of Sciences 110, 13416-13421.

Fu, Y., et al., *Direct reprogramming of mouse fibroblasts into cardiomyocytes with chemical cocktails*. Cell Res, 2015. 25(9): p. 1013-24.

Gemberling, M., Karra, R., Dickson, A. L., and Poss, K. D. (2015). Nrg1 is an injury-induced cardiomyocyte mitogen for the endogenous heart regeneration program in zebrafish. eLife 4.

Giepmans, B. N., and Moolenaar, W. H. (1998). The gap junction protein connexin43 interacts with the second PDZ domain of the zona occludens-1 protein. Curr Biol 8, 931-934.

Heallen, T., Zhang, M., Wang, J., Bonilla-Claudio, M., Klysik, E., Johnson, R. L., and Martin, J. F. (2011). Hippo pathway inhibits Wnt signaling to restrain cardiomyocyte proliferation and heart size. Science 332, 458-461.

Hsieh, P. C., Segers, V. F., Davis, M. E., MacGillivray, C., Gannon, J., Molkentin, J. D., Robbins, J., and Lee, R. T. (2007). Evidence from a genetic fate-mapping study that stem cells refresh adult mammalian cardiomyocytes after injury. Nat Med 13, 970-974.

Hu, T., and Li, C. (2010). Convergence between Wnt-beta-catenin and EGFR signaling in cancer. Mol Cancer 9, 236.

Hunter, A. W., Barker, R. J., Zhu, C., and Gourdie, R. G. (2005). Zonula occludens-1 alters connexin43 gap junction size and organization by influencing channel accretion. Mol Biol Cell 16, 5686-5698.

Ieda, M., et al., *Direct reprogramming of fibroblasts into functional cardiomyocytes by defined factors*. Cell, 2010. 142(3): p. 375-86.

Ikenishi, A., Okayama, H., Iwamoto, N., Yoshitome, S., Tane, S., Nakamura, K., Obayashi, T., Hayashi, T., and Takeuchi, T. (2012). Cell cycle regulation in mouse heart during embryonic and postnatal stages. Dev Growth Differ 54, 731-738.

Inagaki, K., et al., *Robust systemic transduction with AAV9 vectors in mice: efficient global cardiac gene transfer superior to that of AAV8*. Mol Ther, 2006. 14(1): p. 45-53.

Inagawa, K., et al., *Induction of cardiomyocyte-like cells in infarct hearts by gene transfer of Gata4, Mef2c, and Tbx5*. Circ Res, 2012. 111(9): p. 1147-56.

Itoh, M., Nakadate, K., Horibata, Y., Matsusaka, T., Xu, J., Hunziker, W., and Sugimoto, H. (2014). The structural and functional organization of the podocyte filtration slits is regulated by Tjp1/ZO-1. PLoS One 9, e106621.

Jopling, C., Sleep, E., Raya, M., Marti, M., Raya, A., and Belmonte, J. C. I. (2010). Zebrafish heart regeneration occurs by cardiomyocyte dedifferentiation and proliferation. Nature 464, 606-609.

Jayawardena, T. M., et al., *MicroRNA-mediated in vitro and in vivo direct reprogramming of cardiac fibroblasts to cardiomyocytes*. Circ Res, 2012. 110(11): p. 1465-73.

Katsuno, T., Umeda, K., Matsui, T., Hata, M., Tamura, A., Itoh, M., Takeuchi, K., Fujimori, T., Nabeshima, Y. i., Noda, T., et al. (2008). Deficiency of Zonula Occludens-1 Causes Embryonic Lethal Phenotype Associated with Defected Yolk Sac Angiogenesis and Apoptosis of Embryonic Cells. Molecular Biology of the Cell 19, 2465-2475.

Kerkela, R., Kockeritz, L., MacAulay, K., Zhou, J., Doble, B. W., Beahm, C., Greytak, S., Woulfe, K., Trivedi, C. M., Woodgett, J. R., et al. (2008). Deletion of GSK-3β in mice leads to hypertrophic cardiomyopathy secondary to cardiomyoblast hyperproliferation. Journal of Clinical Investigation 118, 3609-3618.

Kostin, S. (2007). Zonula occludens-1 and connexin 43 expression in the failing human heart. J Cell Mol Med 11, 892-895.

Kubin, T., Poling, J., Kostin, S., Gajawada, P., Hein, S., Rees, W., Wietelmann, A., Tanaka, M., Lorchner, H., Schimanski, S., et al. (2011). Oncostatin M is a major mediator of cardiomyocyte dedifferentiation and remodeling. Cell Stem Cell 9, 420-432.

Laing, J. G., Saffitz, J. E., Steinberg, T. H., and Yamada, K. A. (2007). Diminished zonula occludens-1 expression in the failing human heart. Cardiovasc Pathol 16, 159-164.

Lee, S. H., Hu, L.-L., Gonzalez-Navajas, J., Seo, G. S., Shen, C., Brick, J., Herdman, S., Varki, N., Corr, M., Lee, J., et al. (2010). ERK activation drives intestinal tumorigenesis in Apcmin/+ mice. Nature Medicine 16, 665-670.

Liang, Q., De Windt, L. J., Witt, S. A., Kimball, T. R., Markham, B. E., and Molkentin, J. D. (2001). The Transcription Factors GATA4 and GATA6 Regulate Cardiomyocyte Hypertrophy in Vitro and in Vivo. Journal of Biological Chemistry 276, 30245-30253.

Liang, Q., and Molkentin, J. D. (2003). Redefining the roles of p38 and JNK signaling in cardiac hypertrophy: dichotomy between cultured myocytes and animal models. J Mol Cell Cardiol 35, 1385-1394.

Liebmann, C. (2001). Regulation of MAP kinase activity by peptide receptor signalling pathway: paradigms of multiplicity. Cell Signal 13, 777-785.

Liu, J., Pan, S., Hsieh, M. H., Ng, N., Sun, F., Wang, T., Kasibhatla, S., Schuller, A. G., Li, A. G., Cheng, D., et al. (2013). Targeting Wnt-driven cancer through the inhibition of Porcupine by LGK974. Proceedings of the National Academy of Sciences 110, 20224-20229.

Lopez-Malpartida, A. V., Ludena, M. D., Varela, G., and Garcia Pichel, J. (2009). Differential ErbB receptor expression and intracellular signaling activity in lung adenocarcinomas and squamous cell carcinomas. Lung Cancer 65, 25-33.

Maiers, J. L., Peng, X., Fanning, A. S., and DeMali, K. A. (2013). ZO-1 recruitment to alpha-catenin—a novel mechanism for coupling the assembly of tight junctions to adherens junctions. J Cell Sci 126, 3904-3915.

Mattoon, D. R., Lamothe, B., Lax, I., and Schlessinger, J. (2004). The docking protein Gab 1 is the primary mediator of EGF-stimulated activation of the PI-3K/Akt cell survival pathway. BMC Biol 2, 24.

Muraoka, N., et al., *MiR-133 promotes cardiac reprogramming by directly repressing Snail and silencing fibroblast signatures*. EMBO J, 2014. 33(14): p. 1565-81.

OECD, *In-hospital mortality following acute myocardial infarction", in in Health at a Glance 2011: OECD Indicators*. 2011.

Murphy S L, Kochanek K D, Xu J Q, and E., A. (2015). Mortality in the United States, 2014. In NCHS data brief, no 229 (Hyattsville, Md.: National Center for Health Statistics), pp. 807.

Oka, T. (2006). Cardiac-Specific Deletion of Gata4 Reveals Its Requirement for Hypertrophy, Compensation, and Myocyte Viability. Circulation Research 98, 837-845.

Palatinus, J. A., O'Quinn, M. P., Barker, R. J., Harris, B. S., Jourdan, J., and Gourdie, R. G. (2011). ZO-1 determines adherens and gap junction localization at intercalated disks. Am J Physiol Heart Circ Physiol 300, H583-594.

Pashmforoush, M., Lu, J. T., Chen, H., Amand, T. S., Kondo, R., Pradervand, S., Evans, S. M., Clark, B., Feramisco, J. R., Giles, W., et al. (2004). Nkx2-5 Pathways and Congenital Heart Disease. Cell 117, 373-386.

Polakis, P. (2012). Wnt signaling in cancer. Cold Spring Harb Perspect Biol 4, a008052.

Porrello, E. R., Mahmoud, A. I., Simpson, E., Hill, J. A., Richardson, J. A., Olson, E. N., and Sadek, H. A. (2011). Transient Regenerative Potential of the Neonatal Mouse Heart. Science 331, 1078-1080.

Poss, K. D. (2002). Heart Regeneration in Zebrafish. Science 298, 2188-2190.

Qian, L., et al., *In vivo reprogramming of murine cardiac fibroblasts into induced cardiomyocytes*. Nature, 2012. 485(7400): p. 593-8.

Sepulveda, J. L. (2002). Combinatorial Expression of GATA4, Nkx2-5, and Serum Response Factor Directs Early Cardiac Gene Activity. Journal of Biological Chemistry 277, 25775-25782.

Shapiro, S. D., Ranjan, A. K., Kawase, Y., Cheng, R. K., Kara, R. J., Bhattacharya, R., Guzman-Martinez, G., Sanz, J., Garcia, M. J., and Chaudhry, H. W. (2014). Cyclin A2 Induces Cardiac Regeneration After Myocardial Infarction Through Cytokinesis of Adult Cardiomyocytes. Science Translational Medicine 6, 224ra227-224ra227.

Siddiquee, K., Zhang, S., Guida, W. C., Blaskovich, M. A., Greedy, B., Lawrence, H. R., Yip, M. L. R., Jove, R., McLaughlin, M. M., Lawrence, N. J., et al. (2007). Selective chemical probe inhibitor of Stat3, identified through structure-based virtual screening, induces antitumor activity. Proceedings of the National Academy of Sciences 104, 7391-7396.

Sohal, D. S., Nghiem, M., Crackower, M. A., Witt, S. A., Kimball, T. R., Tymitz, K. M., Penninger, J. M., and Molkentin, J. D. (2001). Temporally regulated and tissue-specific gene manipulations in the adult and embryonic heart using a tamoxifen-inducible Cre protein. Circ Res 89, 20-25.

Song, K., et al., *Heart repair by reprogramming non-myocytes with cardiac transcription factors*. Nature, 2012. 485(7400): p. 599-604.

Soriano, P. (1999). Generalized lacZ expression with the ROSA26 Cre reporter strain. Nat Genet 21, 70-71.

Sy, J. C., et al., *Sustained release of a p38 inhibitor from non-inflammatory microspheres inhibits cardiac dysfunction*. Nat Mater, 2008. 7(11): p. 863-8.

Timmers, L., Sluijter, J. P., van Keulen, J. K., Hoefer, I. E., Nederhoff, M. G., Goumans, M. J., Doevendans, P. A., van Echteld, C. J., Joles, J. A., Quax, P. H., et al. (2008). Toll-like receptor 4 mediates maladaptive left ventricular remodeling and impairs cardiac function after myocardial infarction. Circ Res 102, 257-264.

Toyofuku, T., Yabuki, M., Otsu, K., Kuzuya, T., Hori, M., and Tada, M. (1998). Direct Association of the Gap Junction Protein Connexin-43 with ZO-1 in Cardiac Myocytes. Journal of Biological Chemistry 273, 12725-12731.

Uygur, A., and Lee, R. T. (2016). Mechanisms of Cardiac Regeneration. Dev Cell 36, 362-374.

Wada, R., et al., *Induction of human cardiomyocyte-like cells from fibroblasts by defined factors.* Proc Natl Acad Sci USA, 2013. 110(31): p. 12667-72.

Wang, H., et al., *Small molecules enable cardiac reprogramming of mouse fibroblasts with a single factor, Oct4.* Cell Rep, 2014. 6(5): p. 951-60.

Wang, Y. (2007). Mitogen-activated protein kinases in heart development and diseases. Circulation 116, 1413-1423.

Wei, K., et al., *Epicardial FSTL1 reconstitution regenerates the adult mammalian heart. Nature,* 2015. 525(7570): p. 479-485.

Woulfe, K. C., Gao, E., Lal, H., Harris, D., Fan, Q., Vagnozzi, R., DeCaul, M., Shang, X., Patel, S., Woodgett, J. R., et al. (2010). Glycogen Synthase Kinase-3 Regulates Post-Myocardial Infarction Remodeling and Stress-Induced Cardiomyocyte Proliferation In Vivo. Circulation Research 106, 1635-1645.

Wu, R., Hu, T. C., Rehemtulla, A., Fearon, E. R., and Cho, K. R. (2011). Preclinical Testing of PI3K/AKT/mTOR Signaling Inhibitors in a Mouse Model of Ovarian Endometrioid Adenocarcinoma. Clinical Cancer Research 17, 7359-7372.

Xie, H., Lin, L., Tong, L., Jiang, Y., Zheng, M., Chen, Z., Jiang, X., Zhang, X., Ren, X., Qu, W., et al. (2011). AST1306, A Novel Irreversible Inhibitor of the Epidermal Growth Factor Receptor 1 and 2, Exhibits Antitumor Activity Both In Vitro and In Vivo. PLoS ONE 6, e21487.

Xin, M., Olson, E. N., and Bassel-Duby, R. (2013). Mending broken hearts: cardiac development as a basis for adult heart regeneration and repair. Nature Reviews Molecular Cell Biology 14, 529-541.

Xu, J., Kausalya, P. J., Phua, D. C., Ali, S. M., Hossain, Z., and Hunziker, W. (2008). Early embryonic lethality of mice lacking ZO-2, but Not ZO-3, reveals critical and nonredundant roles for individual zonula occludens proteins in mammalian development. Mol Cell Biol 28, 1669-1678.

Xu, J., et al., *ZO-1 regulates Erk, Smad1/5/8, Smad2, and RhoA activities to modulate self-renewal and differentiation of mouse embryonic stem cells.* Stem Cells, 2012. 30(9): p. 1885-900.

Yahalom-Ronen, Y., Rajchman, D., Sarig, R., Geiger, B., and Tzahor, E. (2015). Reduced matrix rigidity promotes neonatal cardiomyocyte dedifferentiation, proliferation and clonal expansion. Elife 4.

Yamakawa, H., et al., *Fibroblast Growth Factors and Vascular Endothelial Growth Factor Promote Cardiac Reprogramming under Defined Conditions.* Stem Cell Reports, 2015. 5(6): p. 1128-42.

Yoshioka, J., Prince, R. N., Huang, H., Perkins, S. B., Cruz, F. U., MacGillivray, C., Lauffenburger, D. A., and Lee, R. T. (2005). Cardiomyocyte hypertrophy and degradation of connexin43 through spatially restricted autocrine/paracrine heparin-binding EGF. Proc Natl Acad Sci USA 102, 10622-10627.

Zeisberg, E. M., Ma, Q., Juraszek, A. L., Moses, K., Schwartz, R. J., Izumo, S., and Pu, W. T. (2005). Morphogenesis of the right ventricle requires myocardial expression of Gata4. J Clin Invest 115, 1522-1531.

Zhang, X.-D., Baladandayuthapani, V., Lin, H., Mulligan, G., Li, B., Esseltine, D.-L., Qi, L., Xu, J., Hunziker, W., Barlogie, B., et al. (2016). Tight junction protein 1 modulates proteasome capacity and proteasome inhibitor sensitivity in multiple myeloma via EGFR/JAK1/STAT3 signaling. Cancer Cell In press.

Zhao, Y., et al., *High-efficiency reprogramming of fibroblasts into cardiomyocytes requires suppression of pro-fibrotic signalling.* Nat Commun, 2015. 6: p. 8243.

Zhong, Z., Wen, Z., and Darnell, J. E., Jr. (1994). Stat3: a STAT family member activated by tyrosine phosphorylation in response to epidermal growth factor and interleukin-6. Science 264, 95-98.

Zhou, H., et al., *Akt1/protein kinase B enhances transcriptional reprogramming of fibroblasts to functional cardiomyocytes.* Proc Natl Acad Sci USA, 2015. 112(38): p. 11864-9.

Zhou, Q., Li, L., Zhao, B., and Guan, K. L. (2015). The hippo pathway in heart development, regeneration, and diseases. Circ Res 116, 1431-1447.

Zhou, Y., et al., *Bmi1 Is a Key Epigenetic Barrier to Direct Cardiac Reprogramming.* Cell Stem Cell, 2016. 18(3): p. 382-95.

What is claimed is:

1. A method for treating a heart disease in a subject comprising administering to the subject a therapeutically effective amount of Tjp1 inhibitor, wherein the heart disease is a myocardial infarction, wherein the Tjp1 inhibitor is a nucleic acid, and
wherein the nucleic acid is an shRNA, and wherein the shRNA binds to an mRNA encoding Tjp1; and
wherein the nucleic acid encoding the inhibitor has at least 70% identity to a sequence selected from the group consisting of:

(a)
SEQ ID NO: 1
(CCGGGCCTGCATACAATAAAGCAAACTCGAGTTTGCTTTATTGTATGCA

GGCTTTTTG);

(b)
SEQ ID NO: 2
(CCGGGGAACCACTCTATCAAGTATTCTCGAGAATACTTGATAGAGTGGT

TCCTTTTTG);

(c)
SEQ ID NO: 3
(CCGGCGTGGATTGAACTTACTAAATCTCGAGATTTAGTAAGTTCAATCC

ACGTTTTTG);
and (d)
SEQ ID NO: 4
(CCGGCCGCGAAGTTATGAGCAAGTTCTCGAGAACTTGCTCATAACTTCG

CGGTTTTTG).

2. The method of claim 1, wherein the nucleic acid forms a nucleic acid-mRNA complex with the mRNA encoding Tjp1.

3. The method of claim 1, wherein the method further comprises administering an additional factor selected from the group consisting of a polypeptide and a nucleic acid together or separately with the Tjp1 inhibitor.

4. The method of claim 3, wherein the nucleic acid is encoding Cyclin A2.

5. The method of claim 3, wherein the polypeptide binds to ErbB4 receptors.

6. The method of claim 5, wherein the polypeptide binding ErbB4 receptors is selected from the group consisting of Neuregulin-1, Neuregulin-2 (NRG2), Neuregulin-3 (NRG3), Betacellulin (BTC), Epiregulin (EPR), Heparin Binding EGF-like Growth Factor (HB-EGF), Epidermal Growth Factor (EGF), β-Cellulin, Transforming Growth Factor Alpha (TGFα), and Amphiregulin (AR).

7. The method of claim 6, wherein the polypeptide binding ErbB4 receptors is Neuregulin-1 (NRG1).

8. The method of claim 3, wherein the polypeptide activates Wnt signaling.

9. The method of claim 8, wherein the polypeptide activating Wnt signaling is selected from the group consisting of Wnts, Norrin, and R-spondin.

10. The method of claim 3, wherein the polypeptide is a growth factor or a secreted factor.

11. The method of claim 10, wherein the growth factor is Fibroblast Growth Factor (FGF) or Vascular Endothelial Growth Factor (VEGF).

12. The method of claim 10, wherein the secreted factor is Follistatin-like 1 (Fstl 1).

13. The method of claim 1, wherein when the inhibitor is a nucleic acid inhibitor, the method comprises a virus-mediated delivery system.

14. The method of claim 13, wherein the virus is selected from the group consisting of a retrovirus, an adenovirus, an adeno-associated virus, and a herpes simplex virus.

15. The method of claim 14, wherein the virus is an adeno-associated virus.

16. The method of claim 15, wherein the adeno-associated virus is AAV serotype 9.

17. The method of claim 1, wherein the nucleic acid encoding the inhibitor has at least 90% identity to a sequence selected from the group consisting of:

(a)
SEQ ID NO: 1
(CCGGGCCTGCATACAATAAAGCAAACTCGAGTTTGCTTTATTGTATGCA

GGCTTTTTG);

(b)
SEQ ID NO: 2
(CCGGGGAACCACTCTATCAAGTATTCTCGAGAATACTTGATAGAGTGGT

TCCTTTTTG);

(c)

SEQ ID NO: 3
(CCGGCGTGGATTGAACTTACTAAATCTCGAGATTTAGTAAGTTCAATCC

ACGTTTTTG);
and (d)

SEQ ID NO: 4
(CCGGCCGCGAAGTTATGAGCAAGTTCTCGAGAACTTGCTCATAACTTCG

CGGTTTTTG).

18. The method of claim 1, wherein the nucleic acid encoding the inhibitor has a sequence selected from the group consisting of:

(a)

SEQ ID NO: 1
(CCGGGCCTGCATACAATAAAGCAAACTCGAGTTTGCTTTATTGTATGCA

GGCTTTTTG);

(b)

SEQ ID NO: 2
(CCGGGGAACCACTCTATCAAGTATTCTCGAGAATACTTGATAGAGTGGT

TCCTTTTTG);

(c)

SEQ ID NO: 3
(CCGGCGTGGATTGAACTTACTAAATCTCGAGATTTAGTAAGTTCAATCC

ACGTTTTTG);
and (d)

SEQ ID NO: 4
(CCGGCCGCGAAGTTATGAGCAAGTTCTCGAGAACTTGCTCATAACTTCG

CGGTTTTTG).

* * * * *